US009267127B2

(12) United States Patent
Liu et al.

(10) Patent No.: US 9,267,127 B2
(45) Date of Patent: Feb. 23, 2016

(54) EVOLUTION OF BOND-FORMING ENZYMES

(71) Applicant: President and Fellows of Harvard College, Cambridge, MA (US)

(72) Inventors: David R. Liu, Lexington, MA (US); Irwin Chen, San Francisco, CA (US); Brent M. Dorr, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/922,812

(22) Filed: Jun. 20, 2013

(65) Prior Publication Data
US 2014/0057317 A1 Feb. 27, 2014

Related U.S. Application Data

(60) Provisional application No. 61/662,606, filed on Jun. 21, 2012.

(51) Int. Cl.
*C12N 9/52* (2006.01)
*C12P 21/02* (2006.01)
*C12N 9/64* (2006.01)

(52) U.S. Cl.
CPC .............. *C12N 9/52* (2013.01); *C12N 9/6472* (2013.01); *C12P 21/02* (2013.01); *C12Y 304/2207* (2013.01)

(58) Field of Classification Search
None
See application file for complete search history.

(56) References Cited

U.S. PATENT DOCUMENTS

| 6,773,706 B2 | 8/2004 | Mazmanian et al. | |
| 2003/0022178 A1* | 1/2003 | Schneewind et al. | 435/6 |
| 2003/0153020 A1* | 8/2003 | Schneewind et al. | 435/7.32 |
| 2004/0146984 A1* | 7/2004 | Lee et al. | 435/69.3 |
| 2005/0069984 A1* | 3/2005 | Schneewind et al. | 435/69.1 |
| 2011/0321183 A1 | 12/2011 | Ploegh et al. | |

FOREIGN PATENT DOCUMENTS

| WO | WO 02/077183 A2 | 10/2002 |
| WO | WO 2010/087994 A2 | 8/2010 |
| WO | WO 2011/133704 A2 | 10/2011 |
| WO | WO 2013/003555 A1 | 1/2013 |
| WO | WO2014070865 A1 * | 5/2014 |

OTHER PUBLICATIONS

GenBank Accession No. EGA98301.1, published Feb. 15, 2011.*
GenBank Accession No. EGG96311.1, published Apr. 26, 2011.*
GenBank Accession No. EHJ08151.1, published Nov. 16, 2011.*
GenBank Accession No. EFV88450.1, published Jan. 15, 2011.*
GenBank Accession No. EFS19891.1, published Dec. 6, 2010.*

(Continued)

*Primary Examiner* — Robert Mondesi
*Assistant Examiner* — Richard Ekstrom
(74) *Attorney, Agent, or Firm* — Wolf, Greenfield & Sacks, P.C.

(57) ABSTRACT

Strategies, systems, methods, reagents, and kits for the directed evolution of bond-forming enzymes are provided herein. Evolution products, for example, evolved sortases exhibiting enhanced reaction kinetics and/or altered substrate preferences are also provided herein, as are methods for using such evolved bond-forming enzymes. Kits comprising materials, reagents, and cells for carrying out the directed evolution methods described herein are also provided.

32 Claims, 15 Drawing Sheets

(56) References Cited

OTHER PUBLICATIONS

International Search Report and Written Opinion for PCT/US2013/067461, mailed Mar. 19, 2014.
Clyman et al., Integrin receptors on aortic smooth muscle cells mediate adhesion to fibronectin, laminin, and collagen. Circ Res. Jul. 1990;67(1):175-86.
Gianfaldoni et al., Sortase a confers protection against *Streptococcus pneumoniae* in mice. Infect Immun. Jul. 2009;77(7):2957-61. doi: 10.1128/IAI.01516-08. Epub May 11, 2009.
GENBANK Submission: NIH/NCBI, Accession No. NP_647265, Voyich et al.; Aug. 26, 2013.
Agresti et al., Ultrahigh-throughput screening in drop-based microfluidics for directed evolution. Proc Natl Acad Sci USA. Mar. 2, 2010;107(9):4004-9. doi: 10.1073/pnas.0910781107. Epub Feb. 8, 2010.
Antipov et al., Highly L and D enantioselective variants of horseradish peroxidase discovered by an ultrahigh-throughput selection method. Proc Natl Acad Sci U S A. Nov. 18, 2008;105(46):176949. doi:10.1073/pnas.0809851105. Epub Nov. 12, 2008.
Bentley et al., Mutagenesis studies of substrate recognition and catalysis in the sortase a transpeptidase from *Staphylococcus aureus*. J Biol Chem. May 23, 2008;283(21):14762-71. doi: 10.1074/jbc. M800974200. Epub Mar. 28, 2008.
Bershtein et al., Advances in laboratory evolution of enzymes. Curr Opin Chem Biol. Apr. 2008;12(2):151-8. doi: 10.1016/j.cbpa.2008. 01.027. Epub Mar. 7, 2008.
Bloom et al., Evolving strategies for enzyme engineering. Curr Opin Struct Biol. Aug. 2005;15(4):447-52.
Boder et al., Yeast surface display for screening combinatorial polypeptide libraries. Nat Biotechnol. Jun. 1997;15(6):553-7.
Chapman-Smith et al., The C-terminal domain of biotin protein ligase from *E. coli* is required for catalytic activity. Protein Sci. Dec. 2001;10(12):2608-17.
Chen et al., A general strategy for the evolution of bond-forming enzymes using yeast display. Proc Natl Acad Sci U S A. Jul. 12, 2011;108(28):11399-404. doi: 10.1073/pnas.1101046108. Epub Jun. 22, 2011.
Cherry et al., Directed evolution of industrial enzymes: an update. Curr Opin Biotechnol. Aug. 2003;14(4):438-43.
Comfort et al., A comparative genome analysis identifies distinct sorting pathways in gram-positive bacteria. Infect Immun. May 2004;72(5):2710-22.
Dramsi et al., Sorting sortases: a nomenclature proposal for the various sortases of Gram-positive bacteria. Res Microbiol. Apr. 2005;156(3):289-97. Epub Jan. 28, 2005.
Frankel et al., Mutational analysis of active site residues in the *Staphylococcus aureus* transpeptidase SrtA. Biochemistry. Jun. 19, 2007;46(24):7269-78. Epub May 23, 2007.
Gai et al., Yeast surface display for protein engineering and characterization. Curr Opin Struct Biol. Aug. 2007;17(4):467-73. Epub Sep. 17, 2007.
Herman et al., Incorporating Synthetic Oligonucleotides via Gene Reassembly (ISOR): a versatile tool for generating targeted libraries. Protein Eng Des Sel. May 2007;20(5):219-26. Epub May 5, 2007.
Ilangovan et al., Structure of sortase, the transpeptidase that anchors proteins to the cell wall of *Staphylococcus aureus*. Proc Natl Acad Sci U S A. May 22, 2001;98(11):6056-61.
Jiang et al., De novo computational design of retro-aldol enzymes. Science. Mar 7, 2008;319(5868):1387-91. doi: 10.1126/science. 1152692.
Kapust et al., Tobacco etch virus protease: mechanism of autolysis and rational design of stable mutants with wild-type catalytic proficiency. Protein Eng. Dec. 2001;14(12):993-1000.
Kelly et al., Miniaturizing chemistry and biology in microdroplets. Chem Commun (Camb). May 14, 2007;(18):1773-88. Epub Feb. 23, 2007.

Kim et al , Inhibition of the bacterial surface protein anchoring transpeptidase sortase by isoquinoline alkaloids. Biosci Biotechnol Biochem. Feb. 2004;68(2):421-4.
Kolb et al., Click Chemistry: Diverse Chemical Function from a Few Good Reactions. Angew Chem Int Ed Engl. Jun. 1, 2001;40(11):2004-2021.
Kruger et al., Analysis of the substrate specificity of the *Staphylococcus aureus* sortase transpeptidase SrtA. Biochemistry. Feb. 17, 2004;43(6):1541-51.
Kruger et al., Development of a high-performance liquid chromatography assay and revision of kinetic parameters for the *Staphylococcus aureus* sortase transpeptidase SrtA. Anal Biochem. Mar. 1, 2004;326(1):42-8.
Maresso et al., Activation of inhibitors by sortase triggers irreversible modification of the active site. J Biol Chem. Aug. 10, 2007;282(32):23129-39. Epub Jun. 1, 2007.
Mofid et al., Structure-based mutational analysis of the 4'-phosphopantetheinyl transferases Sfp from Bacillus subtilis: carrier protein recognition and reaction mechanism. Biochemistry. Apr. 13, 2004;43(14):4128-36.
Müller et al., Nucleotide exchange and excision technology (NExT) DNA shuffling: a robust method for DNA fragmentation and directed evolution. Nucleic Acids Res. Aug. 1, 2005;33(13):e117.
Neuenschwander et al., A simple selection strategy for evolving highly efficient enzymes. Nat Biotechnol. Oct. 2007;25(10):1145-7. Epub Sep. 16, 2007.
Olsen et al., Function-based isolation of novel enzymes from a large library. Nat Biotechnol. Oct. 2000;18(10):1071-4.
Pallen et al., An embarrassment of sortases—a richness of substrates? Trends Microbiol. Mar. 2001;9(3):97-101.
Popp et al., Sortagging: A versatile method for protein labeling. Nat Chem Biol. Nov. 2007;3(11):707-8. Epub Sep. 23, 2007.
Qu et al., Immobilization of actively thromboresistant assemblies on sterile blood-contacting surfaces. Adv Healthc Mater. Jan. 2014;3(1):30-5. doi: 10.1002/adhm.201300110. Epub Jun. 21, 2013.
Röthlisberger et al., Kemp elimination catalysts by computational enzyme design. Nature. May 8, 2008;453(7192):190-5. doi: 10.1038/nature06879. Epub Mar. 19, 2008.
Seelig et al., Selection and evolution of enzymes from a partially randomized non-catalytic scaffold. Nature. Aug. 16, 2007;448(7155):828-31.
Siegel et al., Computational design of an enzyme catalyst for a stereoselective bimolecular Diels-Alder reaction. Science. Jul. 16, 2010;329(5989):309-13. doi: 10.1126/science.1190239.
Sunbul et al., Catalytic turnover-based phage selection for engineering the substrate specificity of Sfp phosphopantetheinyltransferase. J Mol Biol. Apr. 10, 2009;387(4):883-98.
Suree et al., The structure of the *Staphylococcus aureus* sortase-substrate complex reveals how the universally conserved LPXTG sorting signal is recognized. J Biol Chem. Sep. 4, 2009;284(36):24465-77. doi: 10.1074/jbc.M109.022624. Epub Jul. 10, 2009.
Tsukiji et al., Sortase-mediated ligation: a gift from Gram-positive bacteria to protein engineering. Chembiochem. Mar. 23, 2009;10(5):787-98. doi: 10.1002/cbic.200800724.
Turner, Directed evolution of enzymes for applied biocatalysis. Trends Biotechnol. Nov. 2003;21(11):474-8.
Uttamapinant et al., A fluorophore ligase for site-specific protein labeling inside living cells. Proc Natl Acad Sci U S A. Jun. 15, 2010;107(24):10914-9. doi: 10.1073/pnas.0914067107. Epub Jun. 7, 2010.
Van Sint Fiet et al., Selection of biocatalysts for chemical synthesis. Proc Natl Acad Sci U S A. Feb. 7, 2006;103(6):1693-8. Epub Jan. 30, 2006.
Varadarajan et al., Highly active and selective endopeptidases with programmed substrate specificities. Nat Chem Biol. May 2008;4(5):290-4. doi: 10.1038/nchembio.80.

(56) References Cited

OTHER PUBLICATIONS

Vellard, The enzyme as drug: application of enzymes as pharmaceuticals. Curr Opin Biotechnol. Aug. 2003;14(4):444-50.
Walsh, Biopharmaceutical benchmarks 2006. Nat Biotechnol. Jul. 2006;24(7):769-76.
Yang et al., Ultrahigh-throughput FACS-based screening for directed enzyme evolution. Chembiochem. Nov. 23, 2009;10(17):2704-15. doi:10.1002/cbic.200900384.
Zaccolo et al., An approach to random mutagenesis of DNA using mixtures of triphosphate derivatives of nucleoside analogues. J Mol Biol. Feb. 2, 1996; 255(4):589-603.
Zhou et al., Genetically encoded short peptide tags for orthogonal protein labeling by Sfb and AcpS phosphopantetheinyl transferases. ACS Chem Biol. May 22, 2007;2(5):337-46. Epub Apr. 27, 2007.
International Search Report and Written Opinion for PCT/US2014/056550, mailed Jan. 29, 2015.

* cited by examiner

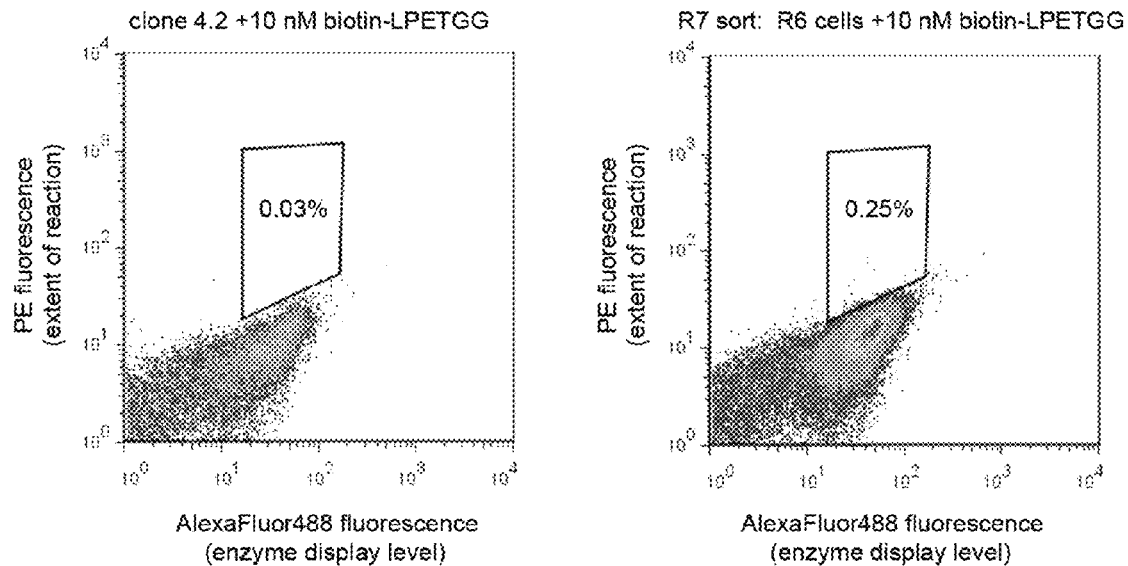

FIGURE 10

| | substrate A-CoA | biotin-substrate B, concentration | reaction time | cells sorted | cells recovered |
|---|---|---|---|---|---|
| R0 (diversity: 7.8x10$^7$) | | | | | |
| R1 | GGGK-CoA | Biotin-LPETGS, 100 µM | 60 min | 6.0x10$^6$ | 8.5x10$^6$ |
| R2 | GGGK-CoA | Biotin-LPETGG, 10 µM | 60 min | 1.2x10$^8$ | 1.2x10$^6$ |
| R3 | GGGK-CoA | Biotin-LPETGS, 1 µM | 60 min | 2.5x10$^7$ | 1.3x10$^5$ |
| R4 | GGGK-CoA | Biotin-LPETGG, 100 nM | 15 min | 1.3x10$^7$ | 2.0x10$^4$ |
| R4Shuf (diversity: 6.9x10$^7$) | | | | | |
| R5 | GGGK-CoA | Biotin-LPETGG, 100 nM | 45 min | 4.0x10$^8$ | 6.0x10$^6$ |
| R6 | GGGK-CoA | Biotin-LPETGS, 100 nM | 30 min | 1.2x10$^8$ | 4.7x10$^5$ |
| R7 | GGGK-CoA | Biotin-LPETGG, 10 nM | 15 min | 2.5x10$^7$ | 6.9x10$^5$ |
| R8 | GGGK-CoA | Biotin-LPETGG, 10 nM | 5 min | 1.0x10$^7$ | 2.0x10$^4$ |
| R9 | CoA-LPETGG | GGGYK-biotin, 100 nM | 5 min | 7.5x10$^6$ | 6.0x10$^3$ |
| | | | | | |
| R8mut (diversity: 5x10$^7$) | | | | | |
| R9mut | CoA-LPETGG | GGGYK-biotin, 1 µM | 15 min | 6.7x10$^7$ | 9.7x10$^4$ |
| R10mut | CoA-LPETGG | GGGYK-biotin, 100 nM | 10 min | 1.25x10$^7$ | 2.8x10$^4$ |

| amino acid (wild-type) | 10m.1 | 10m.2 | 10m.3 | 10m.4 | 10m.5 | 10m.6 | 10m.7 | 10m.8 | 10m.9 | 10m.10 |
|---|---|---|---|---|---|---|---|---|---|---|
| A61 |  | T |  |  |  |  |  |  |  |  |
| I65 |  |  |  | V |  |  |  |  |  |  |
| K84 |  |  |  |  |  |  |  |  | R |  |
| P94 | R | S | S | S | R | S | R | S | S |  |
| E95 |  |  |  |  |  |  | G |  |  |  |
| A104 |  |  |  |  |  |  | V |  |  |  |
| N107 | D |  |  | D |  |  |  |  | S |  |
| A118 |  |  | V |  |  |  |  |  |  |  |
| Q129 |  |  |  | R |  |  |  |  |  |  |
| K137 |  |  |  |  |  |  |  |  |  |  |
| K138 |  |  |  |  | E |  |  |  |  |  |
| M141 |  | V |  |  |  |  |  |  |  |  |
| F144 |  |  | L |  | Y |  |  |  |  |  |
| E149 |  |  |  |  |  |  |  |  | G |  |
| T150 |  |  |  |  |  | A |  |  |  |  |
| S157 |  | G |  |  |  |  |  |  |  |  |
| D160 | N | N | N | N |  | N | N | N | N |  |
| V161 |  |  |  |  |  |  |  | A |  |  |
| T164 |  |  |  |  |  | A |  |  |  |  |
| D165 | A | A | A | A | A | A | A | A | A |  |
| V166 | A |  |  |  |  |  | A |  |  |  |
| V168 |  |  |  |  |  |  |  | A |  |  |
| E171 |  |  |  |  |  |  |  |  | G |  |
| G174 |  |  |  |  |  | S |  |  |  |  |
| K175 |  |  |  |  | R |  |  |  |  |  |
| D176 | G |  |  |  |  |  |  |  |  |  |
| K177 | R | R |  |  |  |  |  |  |  |  |
| Q178 |  |  |  |  |  | R |  |  |  |  |
| I182 |  |  |  |  |  |  |  | V |  |  |
| N188 |  |  |  |  |  | D |  |  |  |  |
| E189 |  | G |  |  |  |  |  |  |  |  |
| K190 |  |  | E | E | E |  | E |  | E |  |
| T191 |  |  |  |  |  |  | A |  |  |  |
| E195 |  |  |  |  |  | G |  |  | G |  |
| K196 | T | T | T | T | T | T | T | T | T |  |
| K198 | R |  |  |  |  |  |  |  |  |  |
| V205 |  |  |  | A |  |  |  |  |  |  |

FIGURE 13 (continued)

LPESG Reprogramming: FACS Selections Round 3

LPESG Reprogramming: FACS Selections Round 4

SEQUENCE LISTING

<160> NUMBER OF SEQ ID NOS: 53

<210> SEQ ID NO 1
<211> LENGTH: 206
<212> TYPE: PRT
<213> ORGANISM: Artificial Sequence
<220> FEATURE:
<223> OTHER INFORMATION: Synthetic polypeptide

<400> SEQUENCE: 1

```
Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Lys Gln Gln Ala Lys Pro Gln
    50                  55                  60

Ile Pro Lys Asp Lys Ser Lys Val Ala Gly Tyr Ile Glu Ile Pro Asp
65              70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Glu Asn Glu Ser Leu Asp Asp
            100                 105                 110

Gln Asn Ile Ser Ile Ala Gly His Thr Phe Ile Asp Arg Pro Asn Tyr
        115                 120                 125

Gln Phe Thr Asn Leu Lys Ala Ala Lys Lys Gly Ser Met Val Tyr Phe
    130                 135                 140

Lys Val Gly Asn Glu Thr Arg Lys Tyr Lys Met Thr Ser Ile Arg Asp
145                 150                 155                 160

Val Lys Pro Thr Asp Val Glu Val Leu Asp Glu Gln Lys Gly Lys Asp
                165                 170                 175

Lys Gln Leu Thr Leu Ile Thr Cys Asp Asp Tyr Asn Glu Lys Thr Gly
            180                 185                 190

Val Trp Glu Lys Arg Lys Ile Phe Val Ala Thr Glu Val Lys
        195                 200                 205
```

<210> SEQ ID NO 2
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2
tccagactat gcaggatctg agaacttgta ctttcaaggt gctagccaag ctaaacctca    60

<210> SEQ ID NO 3
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 3
cagaaataag cttttgttcg gatcctttga cttctgtagc tacaaag    47

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
cccataaaca cacagtatgt t    21

```
<210> SEQ ID NO 5
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 5
accttgaaag tacaagttct cagatcctgc atagtctgga acgtcgt              47

<210> SEQ ID NO 6
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 6
aaagataaac aattaacatt aattactgct gatgattaca atgaa                45

<210> SEQ ID NO 7
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 7
atctcgagct attacaagtc ctcttcagaa ataagctttt gttcgga              47

<210> SEQ ID NO 8
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 8
gtggaggagg ctctggtgga ggcggtagcg gaggcggagg gt                   42

<210> SEQ ID NO 9
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 9
agtaattaat gttaattgtt tatcttt                                    27

<210> SEQ ID NO 10
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 10
tgggaattcc atatgcaagc taaacctcaa attccg                          36

<210> SEQ ID NO 11
<211> LENGTH: 34
<212> TYPE: DNA
<213> ORGANISM: Artificial Sequence
<220> FEATURE:
<223> OTHER INFORMATION: Synthetic oligonucleotide
```

<400> SEQUENCE: 11 tttttctcg agtttgactt ctgtagctac aaag        34

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 12
aattgaaata tggcaggcag c        21

<210> SEQ ID NO 13
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 13
ccaggaccag caacaagyga acaattaaat aga        33

<210> SEQ ID NO 14
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 14
atgacaagta taagaaaygt taagccaaca gckgtagaag ttctagat        48

<210> SEQ ID NO 15
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 15
ttaattactt gtgatggkta caatgaaaag aca        33

<210> SEQ ID NO 16
<211> LENGTH: 291
<212> TYPE: PRT
<213> ORGANISM: Artificial Sequence
<220> FEATURE:
<223> OTHER INFORMATION: Synthetic polypeptide

<400> SEQUENCE: 16

Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
    50                  55                  60

Val Ser Asn Cys Gly Ser His Pro Ser Thr Thr Ser Lys Gly Ser Pro
65                  70                  75                  80

Ile Asn Thr Gln Tyr Val Phe Lys Asp Asn Ser Ser Thr Leu Gln Ala
                85                  90                  95

Ser Gly Gly Gly Gly Ser Gly Gly Gly Ser Gly Gly Gly Ser
            100                 105                 110

Tyr Pro Tyr Asp Val Pro Asp Tyr Ala Gly Ser Glu Asn Leu Tyr Phe
            115                 120                 125

Gln Gly Ala Ser Gln Ala Lys Pro Gln Ile Pro Lys Asp Lys Ser Lys
        130                 135                 140

Val Ala Gly Tyr Ile Glu Ile Pro Asp Ala Asp Ile Lys Glu Pro Val
145                 150                 155                 160

Tyr Pro Gly Pro Ala Thr Pro Glu Gln Leu Asn Arg Gly Val Ser Phe
                165                 170                 175

Ala Glu Glu Asn Glu Ser Leu Asp Asp Gln Asn Ile Ser Ile Ala Gly
            180                 185                 190

His Thr Phe Ile Asp Arg Pro Asn Tyr Gln Phe Thr Asn Leu Lys Ala
            195                 200                 205

Ala Lys Lys Gly Ser Met Val Tyr Phe Lys Val Gly Asn Glu Thr Arg
        210                 215                 220

Lys Tyr Lys Met Thr Ser Ile Arg Asp Val Lys Pro Thr Asp Val Glu
225                 230                 235                 240

Val Leu Asp Glu Gln Lys Ser Lys Asp Lys Gln Leu Thr Leu Ile Thr
                245                 250                 255

Ala Asp Asp Tyr Asn Glu Lys Thr Gly Val Trp Glu Lys Arg Lys Ile
            260                 265                 270

Phe Val Ala Thr Glu Val Lys Gly Ser Glu Gln Lys Leu Ile Ser Glu
        275                 280                 285

Glu Asp Leu
    290

<210> SEQ ID NO 17
<211> LENGTH: 291
<212> TYPE: PRT
<213> ORGANISM: Artificial Sequence
<220> FEATURE:
<223> OTHER INFORMATION: Synthetic polypeptide

<400> SEQUENCE: 17

Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
    50                  55                  60

Val Ser Asn Cys Gly Ser His Pro Ser Thr Thr Ser Lys Gly Ser Pro
65                  70                  75                  80

Ile Asn Thr Gln Tyr Val Phe Lys Asp Asn Ser Ser Thr Leu Gln Ala
                85                  90                  95

Ser Gly Gly Gly Gly Ser Gly Gly Gly Ser Gly Gly Gly Gly Ser
            100                 105                 110

Tyr Pro Tyr Asp Val Pro Asp Tyr Ala Gly Ser Glu Asn Leu Tyr Phe
            115                 120                 125

Gln Gly Ala Ser Gln Ala Lys Pro Gln Ile Pro Lys Asp Lys Ser Lys
        130                 135                 140

Val Ala Gly Tyr Ile Glu Ile Pro Asp Ala Asp Ile Lys Glu Pro Val
145                 150                 155                 160

```
Tyr Pro Gly Pro Ala Thr Ser Glu Gln Leu Asn Arg Gly Val Ser Phe
            165                 170                 175

Ala Glu Glu Asn Glu Ser Leu Asp Asp Gln Asn Ile Ser Ile Ala Gly
        180                 185                 190

His Thr Phe Ile Asp Arg Pro Asn Tyr Gln Phe Thr Asn Leu Lys Ala
    195                 200                 205

Ala Lys Lys Gly Ser Met Val Tyr Phe Lys Val Gly Asn Glu Thr Arg
210                 215                 220

Lys Tyr Lys Met Thr Ser Ile Arg Asn Val Lys Pro Thr Ala Val Glu
225                 230                 235                 240

Val Leu Asp Glu Gln Lys Ser Lys Asp Lys Gln Leu Thr Leu Ile Thr
            245                 250                 255

Cys Asp Asp Tyr Asn Glu Lys Thr Gly Val Trp Glu Thr Arg Lys Ile
        260                 265                 270

Phe Val Ala Thr Glu Val Lys Gly Ser Glu Gln Lys Leu Ile Ser Glu
    275                 280                 285

Glu Asp Leu
    290

<210> SEQ ID NO 18
<211> LENGTH: 291
<212> TYPE: PRT
<213> ORGANISM: Artificial Sequence
<220> FEATURE:
<223> OTHER INFORMATION: Synthetic polypeptide

<400> SEQUENCE: 18

Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
50                  55                  60

Val Ser Asn Cys Gly Ser His Pro Ser Thr Thr Ser Lys Gly Ser Pro
65                  70                  75                  80

Ile Asn Thr Gln Tyr Val Phe Lys Asp Asn Ser Ser Thr Leu Gln Ala
            85                  90                  95

Ser Gly Gly Gly Ser Gly Gly Gly Ser Gly Gly Gly Ser
        100                 105                 110

Tyr Pro Tyr Asp Val Pro Asp Tyr Ala Gly Ser Glu Asn Leu Tyr Phe
        115                 120                 125

Gln Gly Ala Ser Gln Ala Lys Pro Gln Ile Pro Lys Asp Lys Ser Lys
130                 135                 140

Val Ala Gly Tyr Ile Glu Ile Pro Asp Ala Asp Ile Lys Glu Pro Val
145                 150                 155                 160

Tyr Pro Gly Pro Ala Thr Ser Glu Gln Leu Asn Arg Gly Val Ser Phe
            165                 170                 175

Ala Glu Glu Asn Glu Ser Leu Asp Asp Gln Asn Ile Ser Ile Ala Gly
        180                 185                 190

His Thr Phe Ile Asp Arg Pro Asn Tyr Gln Phe Thr Asn Leu Lys Ala
    195                 200                 205

Ala Lys Lys Gly Ser Met Val Tyr Phe Lys Val Gly Asn Glu Thr Arg
210                 215                 220
```

```
Lys Tyr Lys Met Thr Ser Ile Arg Asn Val Lys Pro Thr Ala Val Glu
225                 230                 235                 240

Val Leu Asp Glu Gln Lys Ser Lys Asp Lys Gln Leu Thr Leu Ile Thr
                245                 250                 255

Cys Asp Asp Tyr Asn Glu Glu Thr Gly Val Trp Glu Thr Arg Lys Ile
            260                 265                 270

Phe Val Ala Thr Glu Val Lys Gly Ser Glu Gln Lys Leu Ile Ser Glu
        275                 280                 285

Glu Asp Leu
    290

<210> SEQ ID NO 19
<211> LENGTH: 291
<212> TYPE: PRT
<213> ORGANISM: Artificial Sequence
<220> FEATURE:
<223> OTHER INFORMATION: Synthetic polypeptide

<400> SEQUENCE: 19

Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
    50                  55                  60

Val Ser Asn Cys Gly Ser His Pro Ser Thr Thr Ser Lys Gly Ser Pro
65                  70                  75                  80

Ile Asn Thr Gln Tyr Val Phe Lys Asp Asn Ser Ser Thr Leu Gln Ala
                85                  90                  95

Ser Gly Gly Gly Gly Ser Gly Gly Gly Gly Ser Gly Gly Gly Gly Ser
            100                 105                 110

Tyr Pro Tyr Asp Val Pro Asp Tyr Ala Gly Ser Glu Asn Leu Tyr Phe
        115                 120                 125

Gln Gly Ala Ser Gln Ala Lys Pro Gln Ile Pro Lys Asp Lys Ser Lys
    130                 135                 140

Val Ala Gly Tyr Ile Glu Ile Pro Asp Ala Asp Ile Lys Glu Pro Val
145                 150                 155                 160

Tyr Pro Gly Pro Ala Thr Ser Glu Gln Leu Asn Arg Gly Val Ser Phe
                165                 170                 175

Ala Glu Glu Asn Glu Ser Leu Asp Asp Gln Asn Ile Ser Ile Ala Gly
            180                 185                 190

His Thr Phe Ile Asp Arg Pro Asn Tyr Gln Phe Thr Asn Leu Lys Ala
        195                 200                 205

Ala Lys Lys Gly Ser Met Val Tyr Phe Lys Val Gly Asn Glu Thr Arg
    210                 215                 220

Lys Tyr Arg Met Thr Ser Ile Arg Asn Val Lys Pro Thr Ala Val Glu
225                 230                 235                 240

Val Leu Asp Glu Gln Lys Ser Lys Asp Lys Gln Leu Thr Leu Ile Thr
                245                 250                 255

Cys Asp Asp Tyr Asn Glu Lys Thr Gly Val Trp Glu Thr Arg Lys Ile
            260                 265                 270
```

```
Phe Val Ala Thr Glu Val Lys Gly Ser Glu Gln Lys Leu Ile Ser Glu
        275                 280                 285

Glu Asp Leu
    290

<210> SEQ ID NO 20
<211> LENGTH: 291
<212> TYPE: PRT
<213> ORGANISM: Artificial Sequence
<220> FEATURE:
<223> OTHER INFORMATION: Synthetic polypeptide

<400> SEQUENCE: 20

Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
    50                  55                  60

Val Ser Asn Cys Gly Ser His Pro Ser Thr Thr Ser Lys Gly Ser Pro
65                  70                  75                  80

Ile Asn Thr Gln Tyr Val Phe Lys Asp Asn Ser Ser Thr Leu Gln Ala
                85                  90                  95

Ser Gly Gly Gly Gly Ser Gly Gly Gly Ser Gly Gly Gly Gly Gly Ser
            100                 105                 110

Tyr Pro Tyr Asp Val Pro Asp Tyr Ala Gly Ser Glu Asn Leu Tyr Phe
        115                 120                 125

Gln Gly Ala Ser Gln Ala Lys Pro Gln Ile Pro Lys Asp Lys Ser Lys
    130                 135                 140

Val Ala Gly Tyr Ile Glu Ile Pro Asp Ala Asp Ile Lys Glu Pro Val
145                 150                 155                 160

Tyr Pro Gly Pro Ala Thr Ser Glu Gln Leu Asn Arg Gly Val Ser Phe
                165                 170                 175

Ala Glu Gly Asn Glu Ser Leu Asp Asp Gln Asn Ile Ser Ile Ala Gly
            180                 185                 190

His Thr Tyr Ile Asp Arg Pro Asn Tyr Gln Phe Thr Asn Leu Lys Ala
        195                 200                 205

Ala Lys Lys Gly Ser Met Val Tyr Phe Lys Val Gly Asn Glu Thr Arg
    210                 215                 220

Lys Tyr Lys Met Thr Ser Ile Arg Asn Val Lys Pro Thr Ala Val Glu
225                 230                 235                 240

Val Leu Asp Glu Gln Lys Ser Lys Asp Lys Gln Leu Thr Leu Ile Thr
                245                 250                 255

Cys Asp Asp Tyr Asn Glu Lys Thr Gly Val Trp Glu Thr Arg Lys Ile
            260                 265                 270

Phe Val Ala Thr Glu Val Lys Gly Ser Glu Gln Lys Leu Ile Ser Glu
        275                 280                 285

Glu Asp Leu
    290

<210> SEQ ID NO 21
<211> LENGTH: 156
<212> TYPE: PRT
<213> ORGANISM: Artificial Sequence
```

```
<220> FEATURE:
<223> OTHER INFORMATION: Synthetic polypeptide

<400> SEQUENCE: 21

Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
            20                  25                  30

Pro Ala Thr Pro Glu Gln Leu Asn Arg Gly Val Ser Phe Ala Glu Glu
        35                  40                  45

Asn Glu Ser Leu Asp Asp Gln Asn Ile Ser Ile Ala Gly His Thr Phe
    50                  55                  60

Ile Asp Arg Pro Asn Tyr Gln Phe Thr Asn Leu Lys Ala Ala Lys Lys
65                  70                  75                  80

Gly Ser Met Val Tyr Phe Lys Val Gly Asn Glu Thr Arg Lys Tyr Lys
                85                  90                  95

Met Thr Ser Ile Arg Asp Val Lys Pro Thr Asp Val Glu Val Leu Asp
            100                 105                 110

Glu Gln Lys Gly Lys Asp Lys Gln Leu Thr Leu Ile Thr Cys Asp Asp
        115                 120                 125

Tyr Asn Glu Lys Thr Gly Val Trp Glu Lys Arg Lys Ile Phe Val Ala
    130                 135                 140

Thr Glu Val Lys Leu Glu His His His His His
145                 150                 155

<210> SEQ ID NO 22
<211> LENGTH: 156
<212> TYPE: PRT
<213> ORGANISM: Artificial Sequence
<220> FEATURE:
<223> OTHER INFORMATION: Synthetic polypeptide

<400> SEQUENCE: 22

Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
            20                  25                  30

Pro Ala Thr Ser Glu Gln Leu Asn Arg Gly Val Ser Phe Ala Glu Glu
        35                  40                  45

Asn Glu Ser Leu Asp Asp Gln Asn Ile Ser Ile Ala Gly His Thr Phe
    50                  55                  60

Ile Asp Arg Pro Asn Tyr Gln Phe Thr Asn Leu Lys Ala Ala Lys Lys
65                  70                  75                  80

Gly Ser Met Val Tyr Phe Lys Val Gly Asn Glu Thr Arg Lys Tyr Lys
                85                  90                  95

Met Thr Ser Ile Arg Asp Val Lys Pro Thr Asp Val Glu Val Leu Asp
            100                 105                 110

Glu Gln Lys Gly Lys Asp Lys Gln Leu Thr Leu Ile Thr Cys Asp Asp
        115                 120                 125

Tyr Asn Glu Lys Thr Gly Val Trp Glu Lys Arg Lys Ile Phe Val Ala
    130                 135                 140

Thr Glu Val Lys Leu Glu His His His His His
145                 150                 155
```

<210> SEQ ID NO 23
<211> LENGTH: 156
<212> TYPE: PRT
<213> ORGANISM: Artificial Sequence
<220> FEATURE:
<223> OTHER INFORMATION: Synthetic polypeptide

<400> SEQUENCE: 23

```
Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
                20                  25                  30

Pro Ala Thr Pro Glu Gln Leu Asn Arg Gly Val Ser Phe Ala Glu Glu
            35                  40                  45

Asn Glu Ser Leu Asp Asp Gln Asn Ile Ser Ile Ala Gly His Thr Phe
    50                  55                  60

Ile Asp Arg Pro Asn Tyr Gln Phe Thr Asn Leu Lys Ala Ala Lys Lys
65                  70                  75                  80

Gly Ser Met Val Tyr Phe Lys Val Gly Asn Glu Thr Arg Lys Tyr Lys
                85                  90                  95

Met Thr Ser Ile Arg Asn Val Lys Pro Thr Asp Val Glu Val Leu Asp
                100                 105                 110

Glu Gln Lys Gly Lys Asp Lys Gln Leu Thr Leu Ile Thr Cys Asp Asp
            115                 120                 125

Tyr Asn Glu Lys Thr Gly Val Trp Glu Lys Arg Lys Ile Phe Val Ala
    130                 135                 140

Thr Glu Val Lys Leu Glu His His His His His His
145                 150                 155
```

<210> SEQ ID NO 24
<211> LENGTH: 156
<212> TYPE: PRT
<213> ORGANISM: Artificial Sequence
<220> FEATURE:
<223> OTHER INFORMATION: Synthetic polypeptide

<400> SEQUENCE: 24

```
Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
                20                  25                  30

Pro Ala Thr Pro Glu Gln Leu Asn Arg Gly Val Ser Phe Ala Glu Glu
            35                  40                  45

Asn Glu Ser Leu Asp Asp Gln Asn Ile Ser Ile Ala Gly His Thr Phe
    50                  55                  60

Ile Asp Arg Pro Asn Tyr Gln Phe Thr Asn Leu Lys Ala Ala Lys Lys
65                  70                  75                  80

Gly Ser Met Val Tyr Phe Lys Val Gly Asn Glu Thr Arg Lys Tyr Lys
                85                  90                  95

Met Thr Ser Ile Arg Asp Val Lys Pro Thr Ala Val Glu Val Leu Asp
                100                 105                 110

Glu Gln Lys Gly Lys Asp Lys Gln Leu Thr Leu Ile Thr Cys Asp Asp
            115                 120                 125

Tyr Asn Glu Lys Thr Gly Val Trp Glu Lys Arg Lys Ile Phe Val Ala
    130                 135                 140

Thr Glu Val Lys Leu Glu His His His His His
145                 150                 155
```

```
<210> SEQ ID NO 25
<211> LENGTH: 156
<212> TYPE: PRT
<213> ORGANISM: Artificial Sequence
<220> FEATURE:
<223> OTHER INFORMATION: Synthetic polypeptide

<400> SEQUENCE: 25

Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
                20                  25                  30

Pro Ala Thr Pro Glu Gln Leu Asn Arg Gly Val Ser Phe Ala Glu Glu
            35                  40                  45

Asn Glu Ser Leu Asp Asp Gln Asn Ile Ser Ile Ala Gly His Thr Phe
        50                  55                  60

Ile Asp Arg Pro Asn Tyr Gln Phe Thr Asn Leu Lys Ala Ala Lys Lys
65                  70                  75                  80

Gly Ser Met Val Tyr Phe Lys Val Gly Asn Glu Thr Arg Lys Tyr Lys
                85                  90                  95

Met Thr Ser Ile Arg Asp Val Lys Pro Thr Asp Val Glu Val Leu Asp
                100                 105                 110

Glu Gln Lys Gly Lys Asp Lys Gln Leu Thr Leu Ile Thr Cys Asp Asp
            115                 120                 125

Tyr Asn Glu Lys Thr Gly Val Trp Glu Thr Arg Lys Ile Phe Val Ala
        130                 135                 140

Thr Glu Val Lys Leu Glu His His His His His His
145                 150                 155

<210> SEQ ID NO 26
<211> LENGTH: 156
<212> TYPE: PRT
<213> ORGANISM: Artificial Sequence
<220> FEATURE:
<223> OTHER INFORMATION: Synthetic polypeptide

<400> SEQUENCE: 26

Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
                20                  25                  30

Pro Ala Thr Pro Glu Gln Leu Asn Arg Gly Val Ser Phe Ala Glu Glu
            35                  40                  45

Asn Glu Ser Leu Asp Asp Gln Asn Ile Ser Ile Ala Gly His Thr Phe
        50                  55                  60

Ile Asp Arg Pro Asn Tyr Gln Phe Thr Asn Leu Lys Ala Ala Lys Lys
65                  70                  75                  80

Gly Ser Met Val Tyr Phe Lys Val Gly Asn Glu Thr Arg Lys Tyr Lys
                85                  90                  95

Met Thr Ser Ile Arg Asn Val Lys Pro Thr Asp Val Glu Val Leu Asp
                100                 105                 110

Glu Gln Lys Gly Lys Asp Lys Gln Leu Thr Leu Ile Thr Cys Asp Asp
            115                 120                 125

Tyr Asn Glu Glu Thr Gly Val Trp Glu Thr Arg Lys Ile Phe Val Ala
        130                 135                 140

Thr Glu Val Lys Leu Glu His His His His His
145                 150                 155
```

```
<210> SEQ ID NO 27
<211> LENGTH: 156
<212> TYPE: PRT
<213> ORGANISM: Artificial Sequence
<220> FEATURE:
<223> OTHER INFORMATION: Synthetic polypeptide

<400> SEQUENCE: 27

Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
                20                  25                  30

Pro Ala Thr Ser Glu Gln Leu Asn Arg Gly Val Ser Phe Ala Glu Glu
            35                  40                  45

Asn Glu Ser Leu Asp Asp Gln Asn Ile Ser Ile Ala Gly His Thr Phe
    50                  55                  60

Ile Asp Arg Pro Asn Tyr Gln Phe Thr Asn Leu Lys Ala Ala Lys Lys
65                  70                  75                  80

Gly Ser Met Val Tyr Phe Lys Val Gly Asn Glu Thr Arg Lys Tyr Lys
                85                  90                  95

Met Thr Ser Ile Arg Asp Val Lys Pro Thr Ala Val Glu Val Leu Asp
                100                 105                 110

Glu Gln Lys Gly Lys Asp Lys Gln Leu Thr Leu Ile Thr Cys Asp Asp
            115                 120                 125

Tyr Asn Glu Lys Thr Gly Val Trp Glu Lys Arg Lys Ile Phe Val Ala
    130                 135                 140

Thr Glu Val Lys Leu Glu His His His His His His
145                 150                 155

<210> SEQ ID NO 28
<211> LENGTH: 156
<212> TYPE: PRT
<213> ORGANISM: Artificial Sequence
<220> FEATURE:
<223> OTHER INFORMATION: Synthetic polypeptide

<400> SEQUENCE: 28

Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
                20                  25                  30

Pro Ala Thr Ser Glu Gln Leu Asn Arg Gly Val Ser Phe Ala Glu Glu
            35                  40                  45

Asn Glu Ser Leu Asp Asp Gln Asn Ile Ser Ile Ala Gly His Thr Phe
    50                  55                  60

Ile Asp Arg Pro Asn Tyr Gln Phe Thr Asn Leu Lys Ala Ala Lys Lys
65                  70                  75                  80

Gly Ser Met Val Tyr Phe Lys Val Gly Asn Glu Thr Arg Lys Tyr Lys
                85                  90                  95

Met Thr Ser Ile Arg Asn Val Lys Pro Thr Ala Val Glu Val Leu Asp
                100                 105                 110

Glu Gln Lys Gly Lys Asp Lys Gln Leu Thr Leu Ile Thr Cys Asp Asp
            115                 120                 125

Tyr Asn Glu Lys Thr Gly Val Trp Glu Thr Arg Lys Ile Phe Val Ala
    130                 135                 140

Thr Glu Val Lys Leu Glu His His His His His
145                 150                 155
```

```
<210> SEQ ID NO 29
<211> LENGTH: 156
<212> TYPE: PRT
<213> ORGANISM: Artificial Sequence
<220> FEATURE:
<223> OTHER INFORMATION: Synthetic polypeptide

<400> SEQUENCE: 29

Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
                20                  25                  30

Pro Ala Thr Ser Glu Gln Leu Asn Arg Gly Val Ser Phe Ala Glu Glu
            35                  40                  45

Asn Glu Ser Leu Asp Asp Gln Asn Ile Ser Ile Ala Gly His Thr Phe
        50                  55                  60

Ile Asp Arg Pro Asn Tyr Gln Phe Thr Asn Leu Lys Ala Ala Lys Lys
65                  70                  75                  80

Gly Ser Met Val Tyr Phe Lys Val Gly Asn Glu Thr Arg Lys Tyr Lys
                85                  90                  95

Met Thr Ser Ile Arg Asn Val Lys Pro Thr Asp Val Glu Val Leu Asp
                100                 105                 110

Glu Gln Lys Gly Lys Asp Lys Gln Leu Thr Leu Ile Thr Cys Asp Asp
            115                 120                 125

Tyr Asn Glu Lys Thr Gly Val Trp Glu Thr Arg Lys Ile Phe Val Ala
        130                 135                 140

Thr Glu Val Lys Leu Glu His His His His His His
145                 150                 155

<210> SEQ ID NO 30
<211> LENGTH: 156
<212> TYPE: PRT
<213> ORGANISM: Artificial Sequence
<220> FEATURE:
<223> OTHER INFORMATION: Synthetic polypeptide

<400> SEQUENCE: 30

Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
                20                  25                  30

Pro Ala Thr Ser Glu Gln Leu Asn Arg Gly Val Ser Phe Ala Glu Glu
            35                  40                  45

Asn Glu Ser Leu Asp Asp Gln Asn Ile Ser Ile Ala Gly His Thr Phe
        50                  55                  60

Ile Asp Arg Pro Asn Tyr Gln Phe Thr Asn Leu Lys Ala Ala Lys Lys
65                  70                  75                  80

Gly Ser Met Val Tyr Phe Lys Val Gly Asn Glu Thr Arg Lys Tyr Lys
                85                  90                  95

Met Thr Ser Ile Arg Asn Val Lys Pro Thr Ala Val Glu Val Leu Asp
                100                 105                 110

Glu Gln Lys Gly Lys Asp Lys Gln Leu Thr Leu Ile Thr Cys Asp Asp
            115                 120                 125

Tyr Asn Glu Lys Thr Gly Val Trp Glu Lys Arg Lys Ile Phe Val Ala
        130                 135                 140

Thr Glu Val Lys Leu Glu His His His His His His
145                 150                 155
```

```
<210> SEQ ID NO 31
<211> LENGTH: 156
<212> TYPE: PRT
<213> ORGANISM: Artificial Sequence
<220> FEATURE:
<223> OTHER INFORMATION: Synthetic polypeptide

<400> SEQUENCE: 31

Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
            20                  25                  30

Pro Ala Thr Arg Glu Gln Leu Asn Arg Gly Val Ser Phe Ala Glu Glu
        35                  40                  45

Asn Glu Ser Leu Asp Asp Gln Asn Ile Ser Ile Ala Gly His Thr Phe
    50                  55                  60

Ile Asp Arg Pro Asn Tyr Gln Phe Thr Asn Leu Lys Ala Ala Lys Lys
65                  70                  75                  80

Gly Ser Met Val Tyr Phe Lys Val Gly Asn Glu Thr Arg Lys Tyr Lys
                85                  90                  95

Met Thr Ser Ile Arg Asn Val Lys Pro Thr Ala Val Glu Val Leu Asp
            100                 105                 110

Glu Gln Lys Gly Lys Asp Lys Gln Leu Thr Leu Ile Thr Cys Asp Asp
        115                 120                 125

Tyr Asn Glu Glu Thr Gly Val Trp Glu Thr Arg Lys Ile Phe Val Ala
    130                 135                 140

Thr Glu Val Lys Leu Glu His His His His His His
145                 150                 155

<210> SEQ ID NO 32
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 32

Leu Pro Glu Thr Gly
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 33

Leu Pro Glu Thr Gly Gly
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 34

Leu Pro Glu Thr Gly Gly Gly
1               5
```

```
<210> SEQ ID NO 35
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 35

Gly Gly Gly Lys
1

<210> SEQ ID NO 36
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 36

Leu Pro Glu Thr Gly Ser
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 37

Gly Gly Gly Tyr Lys
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 38

Leu Pro Glu Ser Gly
1               5

<210> SEQ ID NO 39
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 39

Leu Pro Ala Thr
1

<210> SEQ ID NO 40
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any amino acid
```

```
<400> SEQUENCE: 40

Leu Pro Xaa Thr Ala
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any amino acid

<400> SEQUENCE: 41

Leu Ala Xaa Thr Gly
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any amino acid

<400> SEQUENCE: 42

Met Pro Xaa Thr Gly
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any amino acid

<400> SEQUENCE: 43

Leu Ala Xaa Ser Gly
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any amino acid

<400> SEQUENCE: 44

Asn Pro Xaa Thr Gly
1               5

<210> SEQ ID NO 45
<211> LENGTH: 5
<212> TYPE: PRT
<213> ORGANISM: Artificial Sequence
```

```
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any amino acid

<400> SEQUENCE: 45

Asn Ala Xaa Thr Gly
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any amino acid

<400> SEQUENCE: 46

Asn Ala Xaa Ser Gly
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any amino acid

<400> SEQUENCE: 47

Leu Pro Xaa Pro Gly
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 48

Leu Pro Glu Thr Gly Lys
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 49

Leu Glu Leu Pro Glu Thr Gly Gly
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic polypeptide
```

```
<400> SEQUENCE: 50

Tyr Leu Glu Leu Pro Glu Thr Gly Gly
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any amino acid

<400> SEQUENCE: 51

Leu Pro Xaa Thr Gly
1               5

<210> SEQ ID NO 52
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 52

Leu Cys Tyr Gly Leu Pro Glu Thr Gly Ser
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 53

Gly Asp Ser Leu Ser Trp Leu Leu Arg Leu Leu Leu Asn
1               5                   10
```

EVOLUTION OF BOND-FORMING ENZYMES

RELATED APPLICATIONS

The present application claims priority under 35 U.S.C. §119(e) to U.S. provisional application, U.S. Ser. No. 61/662,606, filed Jun. 21, 2012, the entire contents of which are incorporated herein by reference.

GOVERNMENT SUPPORT

This invention was made with U.S. Government support under grant R01 GM065400 awarded by the National Institutes of Health and under grant HR0011-08-0085 awarded by United States Department of Defense and the Defense Advanced Research Projects Agency (DARPA). The U.S. Government has certain rights in the invention.

BACKGROUND OF THE INVENTION

The ability to routinely generate efficient enzymes that catalyze bond-forming reactions chosen by researchers, rather than nature, is a long-standing goal of the molecular life sciences. Such catalysts can be used to form bonds between molecules, e.g., proteins, nucleic acids, carbohydrates, or small molecules, under physiological conditions, thus allowing in vivo and in vitro modification of molecules in or on living cells and other biological structures while maintaining their structural integrity. The spectrum of bond-forming reactions catalyzed by naturally occurring enzymes, e.g., naturally occurring sortases, ligases, polymerases, and kinases, is limited and typically restricted to specific substrates. For example, sortases catalyze a transpeptidation reaction that results in the conjugation of a peptide comprising a C-terminal sortase recognition motif with a peptide comprising an N-terminal sortase recognition motif. Naturally occurring sortases are typically selective for specific C-terminal and N-terminal recognition motifs, e.g., LPXTG (SEQ ID NO: 51) (where X represents any amino acid) and GGG, respectively. The spectrum of peptides and proteins that can be conjugated via sortases is, therefore, limited. While target proteins not comprising a sortase recognition sequence may be engineered to add such a sequence, such engineering is often cumbersome or impractical, e.g., in situations where the addition of an exogenous sortase recognition motif would disturb the structure and/or the function of the native protein. Another obstacle to a broader application of bond-forming enzymes to biological systems is that naturally occurring bond-forming enzymes typically exhibit low reaction efficiencies. The generation of bond-forming enzymes that efficiently catalyze bond-forming reactions and/or utilize a desired target substrate, e.g., a desired sortase recognition sequence, would allow for a broader application of bond-forming reactions to conjugate biomolecules.

SUMMARY OF THE INVENTION

Provided herein are strategies, systems, methods, and reagents for evolving enzymes that catalyze any bond-forming reaction. The technology provided herein integrates yeast display, enzyme-mediated bioconjugation, and fluorescence-activated cell sorting to isolate cells expressing proteins that catalyze the coupling of two target substrates. The strategies provided herein can be used to evolve bond-forming enzymes with improved catalytic activity and/or altered substrate preference. For example, as described herein, several variants of S. aureus sortase A were evolved that exhibited up to a 140-fold increase in transpeptidation activity compared to the starting wild type enzyme. One advantage of the evolution strategies provided herein is that they do not rely on any particular screenable or selectable property of the substrates or reaction products. Accordingly, the evolution strategies provided herein are broadly applicable to evolve bond-forming enzymes utilizing any substrate and catalyzing any bond-forming reaction.

Some embodiments of this invention provide evolved sortases. In some embodiments, a sortase is provided that comprises an amino acid sequence that is at least 90% homologous to the amino acid sequence of S. aureus Sortase A as provided as SEQ ID NO: 1, or a fragment thereof. In some embodiments, the amino acid sequence of the sortase comprises one or more mutations selected from the group consisting of P94S, P94R, E106G, F122Y, F154R, D160N, D165A, G174S, K190E, and K196T. In some embodiments, the sortase comprises an amino acid sequence that is at least 95%, at least 98%, or at least 99% homologous to SEQ ID NO: 1, or a fragment thereof. In some embodiments, the amino acid sequence of the sortase comprises at least one mutation, at least two mutations, at least three mutations, or at least four mutations as compared to the amino acid sequence of S. aureus Sortase A provided as SEQ ID NO: 1, or a fragment thereof. In some embodiments, wherein the sortase comprises a P94S or P94R mutation, a D160N mutation, a D165A mutation, a K190E mutation, and a K196T mutation. In some embodiments, the sortase comprises a P94S or P94R mutation, a D160N mutation, and a K196T mutation. In some embodiments, the sortase comprises a P94S or P94R mutation, a D160N mutation, and a D165A mutation. In some embodiments, the sortase comprises a P94S or P94R mutation, a D160N mutation, a D165A mutation, and a K196T mutation. In some embodiments, the sortase exhibits a $k_{cat}$ that is at least 1.5-fold, at least 2-fold, or at least 3-fold greater than the $k_{cat}$ of the corresponding wild type S. aureus Sortase A. In some embodiments, the sortase exhibits a $K_M$ for a substrate comprising the amino acid sequence LPETG (SEQ ID NO: 32) that is at least 2-fold, at least 5-fold, or at least 10-fold less than the $K_M$ of the corresponding wild type sortase A. In some embodiments, the sortase exhibits a $K_M$ for a substrate comprising the amino acid sequence GGG that is not more than 2-fold, not more than 5-fold, not more than 10-fold, or not more than 20-fold greater than the $K_M$ of the corresponding wild type sortase A amino acid sequence. In some embodiments, the sortase exhibits a ratio of $K_{cat}/k_4$ for a substrate comprising the amino acid sequence LPETG (SEQ ID NO: 32) that is least 2-fold, at least 5-fold, at least 10-fold, at least 20-fold, at least 50-fold, at least 100-fold, or at least 120-fold greater than the $K_{cat}/K_M$ ratio of the corresponding wild type sortase A.

Certain embodiments of this invention provide evolved sortases catalyzing transpeptidation reactions that utilize a substrate comprising a C-terminal sortase recognition sequence other than LPETG (SEQ ID NO: 32). In some embodiments, the sortase comprising an amino acid sequence that is at least 90%, at least 95%, at least 98%, at least 99%, or at least 99.5% homologous to the amino acid sequence of S. aureus Sortase A as provided as SEQ ID NO: 1 or a fragment thereof. In some embodiments, the amino acid sequence comprises one or more mutations selected from the group consisting of P86L, N98S, A104T, A118T, F122S, D124G, N127S, K134R, K173E, K177E and I182V. In some embodiments, the substrate of the evolved sortase comprises the amino acid sequence LPXSX, wherein each X represents independently any amino acid residue, for example, the amino acid sequence LPESG (SEQ ID NO: 38).

In certain embodiments, this invention provides methods for transpeptidation using an evolved sortase as described herein. In some embodiments, the method comprises contacting a sortase as described herein with a substrate comprising a C-terminal LPETG (SEQ ID NO: 32) sequence and with a substrate comprising an N-terminal GGG sequence under conditions suitable for sortase-mediated transpeptidation. In some embodiments, the LPETG (SEQ ID NO: 32) substrate and/or the GGG substrate are on the surface of a cell. In some embodiments, the cell expresses a surface marker protein that is C-terminally fused to an LPETG (SEQ ID NO: 32) sequence. In some embodiments, the cell expresses a surface marker protein that is N-terminally fused to a GGG sequence. In some embodiments, the LPETG (SEQ ID NO: 32) substrate and/or the GGG substrate are polypeptides or proteins, and the method results in the generation of a protein fusion. In some embodiments, the LPETG (SEQ ID NO: 32) substrate or the GGG substrate comprises a non-protein structure. In some embodiments, the LPETG (SEQ ID NO: 32) substrate or the GGG substrate comprises a detectable label, a small molecule, a nucleic acid, or a polysaccharide.

This invention also provides methods for directed evolution of bond-forming enzymes. In some embodiments, the method comprises (a) providing a cell population in which (i) a first cell surface protein or a cell in the cell population is conjugated to a candidate bond-forming enzyme, wherein different cells within the population of cells comprise different candidate bond-forming enzymes conjugated to the cell surface protein and (ii) a second cell surface protein is conjugated to a substrate A; (b) contacting the cell population with a substrate B conjugated to a detectable label under conditions suitable for the bond-forming enzyme to form a bond between substrate A and substrate B; and (c) identifying and/or isolating a cell that is conjugated to substrate B. In some embodiments, the method comprises (a) providing a yeast cell population in which (i) a library of candidate bond-forming enzymes is expressed as a fusion to an Aga2p cell surface mating factor, wherein different cells within the cell population express different candidate bond-forming enzymes; (ii) an Aga1p cell surface mating factor is covalently bound to the Aga2p cell surface mating factor, wherein the Aga2p cell surface mating factor is conjugated to a substrate A; (b) contacting the cell population with a substrate B conjugated to a detectable label under conditions suitable for the bond-forming enzyme to form a bond between substrate A and substrate B; and (c) identifying and/or isolating a cell that is conjugated to substrate B. In some embodiments, the method further comprises (d) identifying and/or isolating the bond-forming enzyme(s) expressed in the cells isolated in step (c). In some embodiments, the method further comprises (e) subjecting the bond-forming enzyme(s) expressed in the cells isolated in step (c) to a diversification procedure, thus creating a diversified library of candidate bond-forming enzymes, expressing the diversified candidate bond-forming enzyme library as a fusion to an Aga2p cell surface mating factor in a population of yeast cells, and repeating steps (a)-(c). In some embodiments, the diversification procedure comprises random mutagenesis and/or recombination. In some embodiments, substrate A is conjugated to the cell surface protein or the Agap2 cell surface mating factor via a reactive handle. In some embodiments, the candidate enzyme is fused to the cell surface protein or the Agap1 cell surface mating factor via a cleavable linker. In some embodiments, the cleavable linker comprises a protease cleavage site. In some embodiments, the method comprises multiple rounds of performing steps (a)-(d) and a final round of performing steps (a)-(c). In some embodiments, the method comprises decreasing the concentration of substrate B in subsequent rounds of performing steps (a)-(d) or steps (a)-(c). In some embodiments, the method comprises using a modified substrate A or a modified substrate B in subsequent rounds of performing steps (a)-(d) or steps (a)-(c). In some embodiments, the method further comprises comparing the bond-forming properties of at least one enzyme identified or isolated in step (c) with the corresponding wild type enzyme, wherein if the enzyme isolated in step (c) exhibits an improved bond-forming characteristic, it is identified as an enhanced, evolved bond-forming enzyme. In some embodiments, the bond-forming enzymes are transpeptidases. In some embodiments, the transpeptidases are sortases. In some embodiments, the bond-forming enzymes are ligases (e.g., biotin ligases, ubiquitin ligases, peptide ligases, subtiligases), polymerases, kinases, aldolases, diels alderases, transferases (e.g., biotinyl transferases, farnesyl transferases, or phosphopantathienyl transferases).

Other advantages, features, and uses of the invention will be apparent from the Detailed Description of Certain Embodiments, the Drawings, the Examples, and the Claims.

BRIEF DESCRIPTION OF THE DRAWINGS

FIG. 10. FACS enables precise definition of sort gates using parallel control samples. In this example, yeast cells displaying clone 4.2 were subjected to identical reaction conditions and FACS analysis protocols as the cells recovered after R6, enabling the creation of a sort gate (black polygon) that isolates mutants with higher specific activity than clone 4.2 in the R7 sort. The percentage of cells residing within the sort gate is shown.

FIG. 11. Reaction conditions and sorting parameters used to evolve sortases with improved catalytic activity. Also shown are the sequences of SEQ ID NOs: 33, 35, 36 and 37.

FIG. 13. Sequences of clones isolated after (A) R7, (B) R8, (C) R9, and (D) R10mut.

DEFINITIONS

Figure 1:
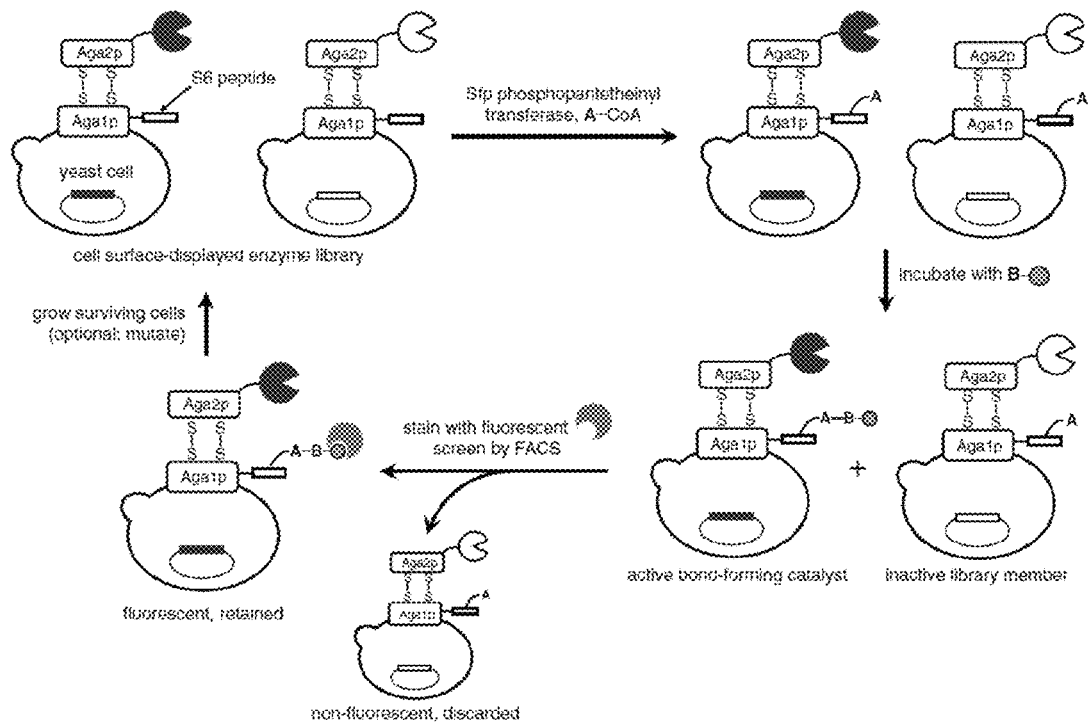
FIG. 1. A general strategy for the evolution of bond-forming catalysts using yeast display.

The term "agent," as used herein, refers to any molecule, entity, or moiety. For example, an agent may be a protein, an amino acid, a peptide, a polynucleotide, a carbohydrate, a lipid, a detectable label, a binding agent, a tag, a metal atom, a contrast agent, a catalyst, a non-polypeptide polymer, a synthetic polymer, a recognition element, a linker, or chemical compound, such as a small molecule. In some embodiments, the agent is a binding agent, for example, a ligand, a ligand-binding molecule, an antibody, or an antibody fragment. Additional agents suitable for use in embodiments of the present invention will be apparent to the skilled artisan. The invention is not limited in this respect.

The term "amino acid," as used herein, includes any naturally occurring and non-naturally occurring amino acid. Suitable natural and non-natural amino acids will be apparent to the skilled artisan, and include, but are not limited to, those described in S. Hunt, The Non-Protein Amino Acids: In *Chemistry and Biochemistry of the Amino Acids*, edited by G. C. Barrett, Chapman and Hall, 1985. Some non-limiting examples of non-natural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with —C(=O)C$_6$H$_5$; —CF$_3$; —CN; -halo; —NO$_2$; —CH$_3$), disubstituted phenylalanines, substituted tyrosines (e.g., further substituted with —C(=O)C$_6$H$_5$; —CF$_3$; —CN; -halo; —NO$_2$; —CH$_3$), and statine. In the context of amino acid sequences, "X" or "Xaa" represents any amino acid residue, e.g., any naturally occurring and/or any non-naturally occurring amino acid residue.

The term "antibody," as used herein, refers to a protein belonging to the immunoglobulin superfamily. The terms antibody and immunoglobulin are used interchangeably. Antibodies from any mammalian species (e.g., human, mouse, rat, goat, pig, horse, cattle, camel) and from non-mammalian species (e.g., from non-mammalian vertebrates, birds, reptiles, amphibia) are within the scope of the term. Suitable antibodies and antibody fragments for use in the context of some embodiments of the present invention include, for example, human antibodies, humanized antibodies, domain antibodies, F(ab'), F(ab')2, Fab, Fv, Fc, and Fd fragments, antibodies in which the Fc and/or FR and/or CDR1 and/or CDR2 and/or light chain CDR3 regions have been replaced by homologous human or non-human sequences; antibodies in which the FR and/or CDR1 and/or CDR2 and/or light chain CDR3 regions have been replaced by homologous human or non-human sequences; antibodies in which the FR and/or CDR1 and/or CDR2 and/or light chain CDR3 regions have been replaced by homologous human or non-human sequences; and antibodies in which the FR and/or CDR1 and/or CDR2 regions have been replaced by homologous human or non-human sequences. In some embodiments, so-called single chain antibodies (e.g., ScFv), (single) domain antibodies, and other intracellular antibodies may be used in the context of the present invention. Domain antibodies, camelid and camelized antibodies and fragments thereof, for example, VHH domains, or nanobodies, such as those described in patents and published patent applications of Ablynx NV and Domantis are also encompassed in the term antibody. Further, chimeric antibodies, e.g., antibodies comprising two antigen-binding domains that bind to different antigens, are also suitable for use in the context of some embodiments of the present invention.

The term "binding agent," as used herein refers to any molecule that binds another molecule. In some embodiments, a binding agent binds another molecule with high affinity. In some embodiments, a binding agent binds another molecule with high specificity. Examples for binding agents include, without limitation, antibodies, antibody fragments, receptors, ligands, aptamers, and adnectins.

The term "bond-forming enzyme," as used herein, refers to any enzyme that catalyzes a reaction resulting in the formation of a covalent bond. In some embodiments, the bond-forming enzyme is a sortase. In some embodiments, the bond-forming enzyme is a ligase, a polymerase, a kinase, an aldolase, a diels alderase, or a transferase (e.g., a biotinyl transferase or a phosphopantathienyl transferase).

The term "conjugated" or "conjugation" refers to an association of two entities, for example, of two molecules such as two proteins, or a protein and a reactive handle, or a protein and an agent, e.g., a detectable label. The association can be, for example, via a direct or indirect (e.g., via a linker) covalent linkage or via non-covalent interactions. In some embodiments, the association is covalent. In some embodiments, two molecules are conjugated via a linker connecting both molecules. For example, in some embodiments where two proteins are conjugated to each other to form a protein fusion, the two proteins may be conjugated via a polypeptide linker, e.g., an amino acid sequence connecting the C-terminus of one protein to the N-terminus of the other protein. In some embodiments, conjugation of a protein to a protein or peptide is achieved by transpeptidation using a sortase. See, e.g., Ploegh et al., International PCT Patent Application, PCT/US2010/000274, filed Feb. 1, 2010, published as WO/2010/087994 on Aug. 5, 2010, and Ploegh et al., International Patent Application PCT/US2011/033303, filed Apr. 20, 2011, published as WO/2011/133704 on Oct. 27, 2011, the entire contents of each of which are incorporated herein by reference, for exemplary sortases, proteins, recognition motifs, reagents, and methods for sortase-mediated transpeptidation.

The term "detectable label" refers to a moiety that has at least one element, isotope, or functional group incorporated into the moiety which enables detection of the molecule, e.g., a protein or peptide, or other entity, to which the label is attached. Labels can be directly attached or can be attached via a linker. It will be appreciated that the label may be attached to or incorporated into a molecule, for example, a protein, polypeptide, or other entity, at any position. In general, a detectable label can fall into any one (or more) of five classes: I) a label which contains isotopic moieties, which may be radioactive or heavy isotopes, including, but not limited to, $^{2}H$, $^{3}H$, $^{13}C$, $^{14}C$, $^{15}N$, $^{18}F$, $^{31}P$, $^{32}P$, $^{35}S$, $^{67}Ga$, $^{76}Br$, $^{99m}Tc$ (Tc-99m), $^{111}In$, $^{123}I$, $^{125}I$, $^{131}I$, $^{153}Gd$, $^{169}Yb$, and $^{186}Re$; II) a label which contains an immune moiety, which may be antibodies or antigens, which may be bound to enzymes (e.g., such as horseradish peroxidase); III) a label which is a colored, luminescent, phosphorescent, or fluorescent moieties (e.g., such as the fluorescent label fluorescein-isothiocyanate (FITC); IV) a label which has one or more photo affinity moieties; and V) a label which is a ligand for one or more known binding partners (e.g., biotin-streptavidin, FK506-FKBP). In certain embodiments, a label comprises a radioactive isotope, preferably an isotope which emits detectable particles, such as β particles. In certain embodiments, the label comprises a fluorescent moiety. In certain embodiments, the label is the fluorescent label fluorescein-isothiocyanate (FITC). In certain embodiments, the label comprises a ligand moiety with one or more known binding partners. In certain embodiments, the label comprises biotin. In some embodiments, a label is a fluorescent polypeptide (e.g., GFP or a derivative thereof such as enhanced GFP (EGFP)) or a luciferase (e.g., a firefly, *Renilla*, or Gaussia luciferase). It will be appreciated that, in certain embodiments, a label may react with a suitable substrate (e.g., a luciferin) to generate a detectable signal. Non-limiting examples of fluorescent proteins include GFP and derivatives thereof, proteins comprising fluorophores that emit light of different colors such as red, yellow, and cyan fluorescent proteins. Exemplary fluorescent proteins include, e.g., Sirius, Azurite, EBFP2, TagBFP, mTurquoise, ECFP, Cerulean, TagCFP, mTFP1, mUkG1, mAG1, AcGFP1, TagGFP2, EGFP, mWasabi, EmGFP, TagYPF, EYFP, Topaz, SYFP2, Venus, Citrine, mKO, mKO2, mOrange, mOrange2, TagRFP, TagRFP-T, mStrawberry, mRuby, mCherry, mRaspberry, mKate2, mPlum, mNeptune, T-Sapphire, mAmetrine, mKeima. See, e.g., Chalfie, M. and Kain, S R (eds.) Green fluorescent protein: properties, applications, and protocols Methods of biochemical analysis, v. 47 Wiley-Interscience, Hoboken, N.J., 2006; and Chudakov, D M, et al., Physiol Rev. 90(3):1103-63, 2010, for discussion of GFP and numerous other fluorescent or luminescent proteins. In some embodiments, a label comprises a dark quencher, e.g., a substance that absorbs excitation energy from a fluorophore and dissipates the energy as heat.

The term "homologous", as used herein is an art-understood term that refers to nucleic acids or polypeptides that are highly related at the level of nucleotide or amino acid sequence. Nucleic acids or polypeptides that are homologous to each other are termed "homologues." Homology between two sequences can be determined by sequence alignment methods known to those of skill in the art. In accordance with the invention, two sequences are considered to be homologous if they are at least about 50-60% identical, e.g., share identical residues (e.g., amino acid residues) in at least about 50-60% of all residues comprised in one or the other sequence, at least about 70% identical, at least about 80% identical, at least about 90% identical, at least about 95% identical, at least about 98% identical, at least about 99% identical, at least about 99.5% identical, or at least about 99.9% identical, for at least one stretch of at least 20, at least 30, at least 40, at least 50, at least 60, at least 70, at least 80, at least 90, at least 100, at least 120, at least 150, or at least 200 amino acids.

The term "$k_{cat}$" refers to the turnover rate of an enzyme, e.g., the number of substrate molecules that the respective enzyme converts to product per time unit. Typically, $k_{cat}$ designates the turnover of an enzyme working at maximum efficiency.

The term "$K_M$" is used herein interchangeably with the term "$K_m$" and refers to the Michaelis constant of an enzyme, an art-recognized measure designating the substrate concentration at ½ the maximum reaction velocity of a reaction catalyzed by the respective enzyme.

The term "linker," as used herein, refers to a chemical group or molecule covalently linked to a molecule, for example, a protein, and a chemical group or moiety, for example, a click chemistry handle. In some embodiments, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer (e.g., PEG), or chemical moiety.

The term "mutation," as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. For example, the term "P94S" in the context of describing a mutation in the *S. aureus* sortase A protein describes a mutation in which the P (proline) residue at position 94 in the sortase A sequence has been replaced by an S (serine) residue, the term "P94R" describes a mutation in which the P (proline) residue at position 94 in the sortase A sequence has been replaced by an R (arginine) residue, the term "E106G" describes a mutation in which the E (glutamate) residue at position 106 in the sortase A sequence has been replaced by a G (glycine) residue, and so forth. See, e.g., SEQ ID NO: 1 for reference of the respective amino acid residue positions in the wild type *S. aureus* sortase A protein.

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof.

The term "reactive handle," as used herein, refers to a reactive moiety that can partake in a bond-forming reaction under physiological conditions. Reactive handles can be used to conjugate entities comprising reactive handles that can react with each other to each other. Examples of suitable reactive handles are, for example, chemical moieties that can partake in a click chemistry reaction (see, e.g., H. C. Kolb, M. G. Finn and K. B. Sharpless (2001). Click Chemistry: Diverse Chemical Function from a Few Good Reactions. *Angewandte Chemie International Edition* 40 (11): 2004-2021). Some suitable reactive handles are described herein and additional suitable reactive handles will be apparent to those of skill in this art, as the present invention is not limited in this respect.

The term "small molecule" is used herein to refer to molecules, whether naturally-occurring or artificially created (e.g., via chemical synthesis) that have a relatively low molecular weight. Typically, a small molecule is an organic compound (i.e., it contains carbon). A small molecule may contain multiple carbon-carbon bonds, stereocenters, and other functional groups (e.g., amines, hydroxyl, carbonyls, or heterocyclic rings). In some embodiments, small molecules are monomeric and have a molecular weight of less than about 1500 g/mol. In certain embodiments, the molecular weight of the small molecule is less than about 1000 g/mol or less than about 500 g/mol. In certain embodiments, the small molecule is a drug, for example, a drug that has already been deemed safe and effective for use in humans or animals by the appropriate governmental agency or regulatory body.

The term "sortase," as used herein, refers to a protein having sortase activity, i.e., an enzyme able to carry out a transpeptidation reaction conjugating the C-terminus of a protein to the N-terminus of a protein via transamidation. The term includes full-length sortase proteins, e.g., full-length naturally occurring sortase proteins, fragments of such sortase proteins that have sortase activity, modified (e.g., mutated) variants or derivatives of such sortase proteins or fragments thereof, as well as proteins that are not derived from a naturally occurring sortase protein, but exhibit sortase activity. Those of skill in the art will readily be able to determine whether or not a given protein or protein fragment exhibits sortase activity, e.g., by contacting the protein or protein fragment in question with a suitable sortase substrate under conditions allowing transpeptidation and determining whether the respective transpeptidation reaction product is formed. In some embodiments, a sortase is a protein comprising at least 20 amino acid residues, at least 30 amino acid C, and sortase D type sortases. Suitable sortases are described, for example, in Dramsi S, Trieu-Cuot P, Bierne H, Sorting sortases: a nomenclature proposal for the various sortases of Gram-positive bacteria. *Res Microbiol.* 156(3): 289-97, 2005; Comfort D, Clubb R T. A comparative genome analysis identifies distinct sorting pathways in gram-positive bacteria. *Infect Immun.*, 72(5):2710-22, 2004; Chen I, Dorr B M, and Liu D R., A general strategy for the evolution of bond-forming enzymes using yeast display. *Proc Natl Acad Sci USA.* 2011 Jul. 12; 108(28):11399; and Pallen, M. J.; Lam, A. C.; Antonio, M.; Dunbar, K. TRENDS in Microbiology, 2001, 9(3), 97-101; the entire contents of each of which are incorporated herein by reference). Any known sortase can be used as a starting enzyme in an evolution strategy provided herein, and the invention is not limited in this respect. For example, the present invention encompasses embodiments relating to a sortase A from any bacterial species or strain. The invention encompasses embodiments relating to a sortase B from any bacterial species or strain. The invention encompasses embodiments relating to a class C sortase from any bacterial species or strain. The invention also encompasses embodiments relating to a class D sortase from any bacterial species or strain. Amino acid sequences of sortases and the nucleotide sequences that encode them are known to those of skill in the art and are disclosed in a number of references cited herein, the entire contents of all of which are incorporated herein by reference. Those of skill in the art will appreciate that any sortase and any sortase recognition motif can be used in some embodiments of this invention, including, but not limited to, the sortases and sortase recognition motifs described in Ploegh et al., International PCT Patent Application, PCT/US2010/000274, filed Feb. 1, 2010, published as WO/2010/087994 on Aug. 5, 2010; and Ploegh et al., International Patent Application PCT/US2011/033303, filed Apr. 20, 2011, published as WO/2011/133704 on Oct. 27, 2011; the entire contents of each of which are incorporated herein by reference. The invention is not limited in this respect.

In some embodiments, the sortase is sortase A of *S. aureus*. For example, in some embodiments, wild type sortase A from *S. aureus* serves as the starting sortase, or parent sortase, for evolving an enhanced sortase according to strategies and methods disclosed herein. The amino acid sequence of wild type sortase A of *S. aureus* is known to those of skill in the art, and a representative sequence (gi|21284177|ref|NP_647265.1) is provided below:

```
                                                    (SEQ ID NO: 1)
MKKWTNRLMTIAGVVLILVAAYLFAKPHIDNYLHDKDKDEKIEQYDKNVKEQASKDK

KQQAKPQIPKDKSKVAGYIEIPDADIKEPVYPGPATPEQLNRGVSFAEENESLDDQNISIA

GHTFIDRPNYQFTNLKAAKKGSMVYFKVGNETRKYKMTSIRDVKPTDVEVLDEQKGK

DKQLTLITCDDYNEKTGVWEKRKIFVATEVK.
``` residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues. In some embodiments, a sortase is a protein comprising less than 100 amino acid residues, less than 125 amino acid residues, less than 150 amino acid residues, less than 175 amino acid residues, less than 200 amino acid residues, or less than 250 amino acid residues.

Suitable sortases will be apparent to those of skill in the art and include, but are not limited to sortase A, sortase B, sortase Additional *S. aureus* sortase A sequences will be apparent to those of skill in the art and the invention is not limited in this respect. In some embodiments, the sortase is a sortase A of another organism, for example, from another bacterial strain, such as *S. pyogenes*. In some embodiments, the sortase is a sortase B, a sortase C, or a sortase D. Suitable sortases from other bacterial strains will be apparent to those of skill in the art, and the invention is not limited in this respect.

The term "sortase substrate," as used herein refers to a molecule or entity that can be utilized in a sortase-mediated transpeptidation reaction. Typically, a sortase utilizes two substrates—a substrate comprising a C-terminal sortase recognition motif, and a second substrate comprising an N-terminal sortase recognition motif and the transpeptidation reaction results in a conjugation of both substrates via a covalent bond. In some embodiments the C-terminal and N-terminal recognition motif are comprised in the same protein, e.g., in the same amino acid sequence. Sortase-mediated conjugation of the substrates in such cases results in the formation of an intramolecular bond, e.g., a circularization of a single amino acid sequence, or, if multiple polypeptides of a protein complex are involved, the formation of an intra-complex bond. In some embodiments, the C-terminal and N-terminal recognition motifs are comprised in different amino acid sequences, for example, in separate proteins. Some sortase recognition motifs are described herein and additional suitable sortase recognition motifs are well known to those of skill in the art. For example, sortase A of S. aureus recognizes and utilizes a C-terminal LPXT motif and an N-terminal GGG motif in transpeptidation reactions. Additional sortase recognition motifs will be apparent to those of skill in the art, and the invention is not limited in this respect. A sortase substrate may comprise additional moieties or entities apart from the peptidic sortase recognition motif. For example, a sortase substrate may comprise an LPXT motif, the N-terminus of which is conjugated to any agent, e.g., a peptide or protein, a small molecule, a binding agent, a lipid, a carbohydrate, or a detectable label. Similarly, a sortase substrate may comprise a GGG motif, the C-terminus of which is conjugated to any agent, e.g., a peptide or protein, a small molecule, a binding agent, a lipid, a carbohydrate, or a detectable label. Accordingly, sortase substrates are not limited to proteins or peptides but include any moiety or entity conjugated to a sortase recognition motif.

The term "target protein," as used herein refers to a protein that comprises a sortase recognition motif. A target protein may be a wild type protein, or may be an engineered protein, e.g., a recombinant protein.

DETAILED DESCRIPTION OF CERTAIN EMBODIMENTS OF THE INVENTION

Despite the many attractive features of enzymes as catalysts for organic synthesis (1), as research tools (2-4), and as an important class of human therapeutics (5, 6), the extent and diversity of their applications remain limited by the difficulty of finding in nature or creating in the laboratory highly active proteins that catalyze chemical reactions of interest. A significant fraction of protein catalysts currently used for research and industrial applications was obtained through the directed evolution of natural enzymes (7). Current methods for the directed evolution of enzymes have resulted in some remarkable successes (8, 9) but generally suffer from limitations in reaction scope. For example, screening enzyme libraries in a multiwell format has proven to be effective for enzymes that process chromogenic or fluorogenic substrates and is typically limited to library sizes of approximately $10^2$-$10^6$ members, depending on the nature of the screen and on available infrastructure (10). Selections of cell-based libraries that couple product formation with auxotrophy complementation (11) or transcription of a reporter gene (12) enable larger library sizes to be processed but also suffer from limited generality because they rely on specific properties of the substrate or product. Likewise, in vitro compartmentalization is a powerful genotype-phenotype co-localization platform that has been used to evolve protein enzymes with improved turnover but also requires corresponding screening or selection methods that thus far have been substrate- or product-specific (13).

Directed evolution strategies that are general for any bond-forming reaction would complement current methods that rely on screenable reactions or selectable properties of the substrate or product. In principle, chemical complementation using an adapted yeast three-hybrid assay is reaction-independent (14) but requires membrane-permeable substrates and offers limited control over reaction conditions because the bond-forming event must take place intracellularly. Phage-display and mRNA-display systems that are general for any bond-forming reaction have been used to evolve enzymes including DNA polymerases (15) and RNA ligases (16). These approaches also offer advantages of larger library sizes and significant control over reaction conditions because the enzymes are displayed extracellularly or expressed in the absence of a host cell.

Some aspects of this invention relate to the recognition that cell surface display (17-20) is an attractive alternative to phage and mRNA display. In contrast to other display methods, the use of bacterial or yeast cells enables up to 100,000 copies of a library member to be linked to one copy of the gene, increasing sensitivity during screening or selection steps. In addition, cell surface-displayed libraries are compatible with powerful fluorescence-activated cell sorting (FACS) that enable very large libraries to be screened efficiently (e.g., at rates of $>10^7$ cells per hour) with precise, quantitative control over screening stringency. The multicolor capabilities of FACS also enable normalization for enzyme display level during screening and simultaneous positive and negative screens, capabilities that are difficult to implement in phage and mRNA display.

Some aspects of this invention provide a technology that is based on an integration of cell display (e.g., yeast display), enzyme-catalyzed small molecule-protein conjugation, and FACS into a general strategy for the evolution of proteins that catalyze bond-forming reactions. The technology was applied to evolve the bacterial transpeptidase sortase A for improved catalytic activity, resulting in sortase variants with an improvement in activity of up to 140-fold. In contrast with wild type (WT) sortase, an evolved sortase enabled highly efficient cell-surface labeling of recombinant human CD 154 expressed on the surface of live HeLa cells with a biotinylated peptide. The technology provided herein can also be used to evolve other bond-forming enzymes, e.g., ligases, polymerases, kinases, transferases, aldolases, diels alderases, and transferases (e.g., biotinyl transferases or phosphopantathienyl transferases), and additional bond-forming enzymes that can be evolved using the methods, reagents, and strategies disclosed herein will be apparent to those of skill in the art based on the instant disclosure.

Evolved Sortases with Enhanced Reaction Kinetics

Some aspects of this invention provide evolved sortases. In some embodiments, the evolved sortase exhibits an enhanced reaction kinetics, for example, in that it catalyzes a transpeptidation reaction at a greater speed or turnover rate than the respective wilt type sortase. In some embodiments, the evolved sortase exhibits a modified substrate preference, for example, in that is utilizes a different substrate (e.g., a polypeptide comprising an altered sortase recognition motif) or binds a given substrate with higher or lower affinity, or with higher or lower specificity than the respective wild type sortase. In some embodiments, the sortase recognizes a sortase recognition motif that the respective wild type sortase does not recognize or bind.

For example, some embodiments provide a sortase comprising an amino acid sequence that is homologous to the amino acid sequence of a wild type sortase (e.g., to the amino acid sequence of S. aureus Sortase A as provided as SEQ ID NO: 1), or a fragment thereof. In some embodiments, the amino acid sequence of the provided sortase comprises one or more mutations as compared to the wild type sequence of the respective sortase. For example, the evolved sortase sequence provided may comprise 1, 2, 3, 4, 5, 6, 7, 8, 9, 10, 11, 12, 13, 14, 15, 16, 17, 18, 19, 20, 25, or more mutations. In some embodiments, the sequence of the provided sortase is at least 90% identical, at least 95% identical, at least 98% identical, at least 99% identical, or at least 99.5% identical to a wild type sortase sequence.

In some embodiments, an evolved *S. aureus* sortase A is provided. In some embodiments, the evolved sortase A comprises a mutation described herein, for example, a P94S, P94R, E106G, F122Y, F154R, D160N, D165A, G174S, K190E, or K196T mutation, or a combination of any of these mutations. In some embodiments, an evolved sortase is provided herein that comprises 1, 2, 3, 4, 5, 6, 7, 8, or all 9 of these mutations. In some embodiments, an evolved sortase A is provided that comprises a mutation that is homologous to the described mutations. For example, in some embodiments, an evolved sortase is provided that comprises a P94S or P94R mutation, a D160N mutation, a D165A mutation, a K190E mutation, and a K196T mutation. In some embodiments, an evolved sortase is provided that comprises a P94S or P94R mutation, a D160N mutation, and a K196T mutation. In some embodiments, an evolved sortase is provided that comprises a P94S or P94R mutation, a D160N mutation, and a D165A mutation. In some embodiments, an evolved sortase is provided that comprises a P94S or P94R mutation, a D160N mutation, a D165A mutation, and a K196T mutation.

Some evolved sortases provided herein exhibit enhanced reaction kinetics, for example, in that they can achieve a greater maximum turnover per time unit ($k_{cat}$) or a greater turnover per time at physiological conditions. For example, in some embodiments, an evolved sortase is provided herein that exhibits a $k_{cat}$ that is at least 1.5-fold, at least 2-fold, at least 2.5-fold, at least 3-fold, at least 3.5-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, or at least 100-fold greater than the $k_{cat}$ of the corresponding wild type sortase.

Some evolved sortases provided herein exhibit enhanced reaction specificities, e.g., in that they bind a substrate with higher affinity or with higher selectivity, or in that they bind a substrate that is not bound or not efficiently bound by the respective wild type sortase. For example, some sortases provided herein exhibit a $K_M$ for a substrate bound by the corresponding wild type sortase that is at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, or at least 50-fold less than the $K_M$ of the corresponding wild type sortase for that substrate. Some evolved sortase A proteins provided herein, for example, exhibit a $K_M$ for a substrate comprising a C-terminal sortase recognition sequence of LPXT that is 2-fold, at least 3-fold, at least 4-fold, at least 5-fold, at least 6-fold, at least 7-fold, at least 8-fold, at least 9-fold, at least 10-fold less than the $K_M$ of the corresponding wild type sortase A for a substrate comprising a C-terminal sortase recognition sequence of LPXT.

In some embodiments, evolved sortases are provided that bind one of their substrates (e.g., a substrate with a C-terminal sortase recognition motif) with a decreased $K_M$ while exhibiting no or only a slight decrease in the $K_M$ for another substrate (e.g., a substrate with an N-terminal sortase recognition motif). For example, some evolved sortases provided herein exhibit a $K_M$ for a substrate comprising a C-terminal sortase recognition motif (e.g., LPXT) that is at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, or at least 50-fold less than the $K_M$ of the corresponding wild type sortase for that substrate, and also exhibit a $K_M$ for a substrate comprising an N-terminal sortase recognition motif (e.g., GGG) that is not more than 2-fold, not more than 5-fold, not more than 10-fold, or not more than 20-fold greater than the $K_M$ of the corresponding wild type sortase (e.g., wt *S. aureus* sortase A).

In some embodiments, evolved sortases are provided herein that exhibit a ratio of $K_{cat}/K_M$ for a substrate bound by the parent wild type sortase that is least 2-fold, at least 5-fold, at least 10-fold, at least 20-fold, at least 50-fold, at least 100-fold, or at least 120-fold greater than the $K_{cat}/K_M$ ratio of the corresponding wild type sortase.

Evolved Sortases with Altered Substrate Preferences

Some aspects of this invention provide evolved sortases that efficiently use substrates not bound by the respective parent wild type sortase. For example, in some embodiments, an evolved sortase is provided that is derived from a wild type *S. aureus* sortase A as the parent sortase A, which utilizes substrates comprising a C-terminal LPXT sortase recognition motif and substrates comprising an N-terminal GGG sortase recognition motif in a transpeptidation reaction. In some embodiments, the evolved sortases utilize a substrate different from those used by the parent sortase, e.g., substrates comprising a C-terminal LPXS, LAXT, LAXTG (SEQ ID NO: 41), MPXT, MPXTG (SEQ ID NO: 42), LAXS, LAXSG (SEQ ID NO: 43), NPXT, NPXTG (SEQ ID NO: 44), NAXT, NAXTG (SEQ ID NO: 45), NAXS, NAXSG (SEQ ID NO: 46), LPXP, LPXPG (SEQ ID NO: 47), or LPXTA (SEQ ID NO: 40) motif. In some embodiments, the evolved sortase comprises an *S. aureus* sortase A amino acid sequence, or a fragment thereof, with one or more of the following mutations: P86L, N98S, A104T, A118T, F122S, D124G, N127S, K134R, K173E, K177E and I182V.

Those of skill in the art will understand that the evolution technology provided herein allows for the generation of evolved sortases recognizing any desired recognition motif. For example, a desired recognition motif may be longer or shorter than the corresponding wild type recognition motif, may comprise one or more amino acid substitutions, insertions, or deletions as compared to the corresponding wild type sortase recognition motif, or may be designed de novo, e.g., not based on any naturally occurring sortase recognition motif. The invention is not limited in this respect.

Methods for Carrying Out Bond-Forming Reactions

Some aspects of this invention provide methods for carrying out bond-forming reactions, for example, sortase-mediated transpeptidation reactions using the evolved sortases described herein. In some embodiments, such methods comprise contacting an evolved sortase provided herein, or a sortase obtained by any of the evolution methods described herein, with a suitable substrate, e.g., a substrate comprising a suitable C-terminal sortase recognition motif and a substrate comprising a suitable N-terminal sortase recognition motif under conditions suitable for sortase-mediated transpeptidation. In some embodiments, the evolved sortase is a sortase A, for example, an evolved *S. aureus* sortase A carrying one or more of the mutations described herein. In some embodiments, the C-terminal sortase recognition motif is LPXT, e.g., LPETG (SEQ ID NO: 32), and/or the N-terminal recognition motif is GGG.

In some embodiments, at least one of the substrates is conjugated to a solid support. In some embodiments, at least one of the substrates is conjugated to the surface of a cell or other biological entity. For example, in some embodiments, at least one of the sortase substrates is expressed as s fusion protein on the surface of a cell, e.g., a cell that expresses a surface marker protein that is C-terminally fused to an amino acid sequence comprising a C-terminal sortase recognition motif (e.g., LPXT), or that is N-terminally fused to an N-terminal sortase recognition motif (e.g., GGG).

The transpeptidation reactions provided herein typically result in the creation of a protein fusion comprising the C-terminal sortase recognition motif and the N-terminal sortase recognition motif. In some embodiments, one of the substrates (e.g., the substrate comprising the C-terminal sortase recognition motif) comprises a non-protein structure, e.g., a detectable label, a small molecule, a nucleic acid, a polymer, or a polysaccharide. It will be apparent to those of skill in the art that the transpeptidation methods provided herein can be applied to conjugate any moieties that can be conjugated by any known sortase or sortase-mediated transpeptidation reaction, including, but not limited to, the reactions and moieties disclosed in Ploegh et al., International PCT Patent Application, PCT/US2010/000274, filed Feb. 1, 2010, published as WO/2010/087994 on Aug. 5, 2010; and Ploegh et al., International Patent Application PCT/US2011/033303, filed Apr. 20, 2011, published as WO/2011/133704 on Oct. 27, 2011; the entire contents of each of which are incorporated herein by reference, for exemplary sortases, proteins, recognition motifs, reagents, moieties, and methods for sortase-mediated transpeptidation. The invention is not limited in this respect.

Strategies for Directed Evolution of Bond-Forming Enzymes

Some aspects of this invention provide methods for the directed evolution of bond-forming enzymes. The evolution methods provided herein are particularly suitable for the evolution of sortases, but, as will be apparent to the skilled artisan, they are not so limited. Any bond-forming enzyme can be evolved according to the strategies and methods described herein. The methods described herein can be used, inter alia, to evolve bond-forming enzymes that exhibit enhanced reaction kinetics and/or altered substrate affinities or specificities as compared to the corresponding wild type enzyme.

In some embodiments, methods for the directed evolution of bond-forming enzymes are provided that involve providing a cell population in which a first cell surface protein of a cell in the cell population is conjugated to a candidate bond-forming enzyme in a manner in which different cells within the population of cells comprise different candidate bond-forming enzymes conjugated to the cell surface protein. In some embodiments, the cells of the cell population also express a second cell surface protein which is conjugated to a target substrate (substrate A). In some embodiments, the method comprises contacting the cell population with a second substrate (substrate B) conjugated to a detectable label under conditions suitable for the bond-forming enzyme to form a bond between the two substrates (A and B). Once the cells have been incubated for a period of time sufficient for a bond-forming enzyme to conjugate the substrates, any unconjugated substrate B can be washed away, and cells expressing a bond-forming enzyme able to catalyze the desired transpeptidation between A and B will retain the detectable label. These cells can be identified and/or isolated, and the identity of the expressed bond-forming enzyme can be determined.

The methods for evolving bond-forming enzymes provided herein can be used to evolve any enzyme, for example, sortases, ligases, polymerases, kinases, diels alderases, and transferases (e.g., biotinyl transferases or phosphopantathienyl transferases), and additional bond-forming enzymes that can be evolved using the methods, reagents, and strategies disclosed herein will be apparent to those of skill in the art based on the instant disclosure. It will be apparent to those of skill in the art that the choice of substrate A and/or B, of the detectable label, and of identifying and/or isolating the cells retaining the detectable label will depend on the enzyme to be evolved. For example, a sortase substrate will be used for the evolution of sortases, a ligase substrate for the evolution of ligases, and so on. Reactions of enzymes that can directly add a detectable label to a substrate, e.g., a transpeptidation reaction that adds a biotinylated peptide or a fluorescent protein to a target substrate, or a ligation reaction, polymerase reaction, or transferase reaction achieving similar additions of a detectable label to a target substrate, can all be read out directly based on the respective cells retaining the detectable label. The evolution of enzymes that do not catalyze a reaction that can directly add a detectable label to a target substrate, for example, of kinases, which merely add a phosphate moiety to a substrate, may require an alteration in the detection strategy. Rather than directly detecting product formation through the inclusion of a detectable label, e.g., a biotinylated tag, the reaction product can be detected indirectly in such embodiments, for example, using an antibody raised against the reaction product (e.g., in the case of a kinase, the phosphorylated product could be detected via an anti-phospho antibody). Direct and indirect labeling strategies are both suitable for downstream detection methods described herein or otherwise known in the art. For example, a directly added biotin moiety can be detected via FACS after streptavidin-PE (phycoerythrin) staining, as described in more detail in the Example section, while an indirectly detected reaction product may be detected by an antibody that is conjugated to a detectable label, e.g., PE, biotin, or a fluorescent moiety.

In some embodiments, the evolution is based on cell display of the candidate bond-forming enzyme in proximity to the target substrate. In some embodiments, the cell display is bacterial display (using, e.g., E. coli or any other suitable bacterial strain). In some embodiments, the cell display is yeast display. For example, in some embodiments, the method includes providing a yeast cell population in which a library of candidate bond-forming enzymes is expressed as a fusion to a surface protein, e.g., an Aga2p cell surface mating factor. Preferably, different cells within the cell population express different candidate bond-forming enzymes. In some embodiments, a target substrate (substrate A) is also conjugated to a cell surface protein, e.g., an Aga1p cell surface mating factor that is covalently bound to the Aga2p cell surface mating factor. In some embodiments, the substrate is a peptide, and the peptide is fused to the surface protein, e.g., to the N-terminus of Agap1. The cell population displaying both the candidate bond-forming enzymes and the target substrate are then contacted with a second substrate (substrate B) that is conjugated to a detectable label. After incubation under conditions suitable for the bond-forming enzyme to form a bond between substrate A and substrate B, unbound substrate B can be washed away, while cells expressing a candidate bond-forming enzyme able to conjugate substrate A and B will retain the detectable label. In some embodiments, labeled cells are detected and/or isolated. In some embodiments, the candidate bond-forming enzyme expressed in a cell that retained the label is identified. Additional suitable display methods and strategies will be apparent to those of skill in the art, and the invention is not limited in this respect.

Some evolution methods provided herein include multiple rounds of screening a library of candidate bond-forming enzymes. In some embodiments, each round of screening is more stringent than the previous round for a desired characteristic of a bond-forming enzyme to be evolved. For example, in some embodiments, subsequent rounds of evolution comprise decreasing concentrations of substrate B to select for bond-forming enzymes that can efficiently conjugate substrate A and B under conditions of low substrate B concentration. In some embodiments, bond-forming enzymes expressed in the cells isolated based on the retention of the detectable label are subjected to a diversification procedure, for example, a random mutagenesis procedure or a DNA shuffling procedure (e.g., using staggered extension PCR (StEP), NeXT uracil excision recombination, or any other suitable method), thus creating a diversified library of candidate bond-forming enzymes, which can then be screened in a new round of selection for conjugation properties.

Methods and protocols for library diversification are well known to those of skill in the art. In some embodiments, diversification may include random mutation or recombination of isolated nucleic acid sequences encoding a parent bond-forming enzyme, and then expressing the diversified library as a fusion to a surface protein in a cell population. In some embodiments, an evolution method provided herein includes 1, 2, 3, 4, 5, 6, 7, 8, 9, 10, 12, 15, 20, 25, 30, or more than 30 cycles of library diversification and selection. In some embodiments, subsequent cycles may comprise a more stringent selection for a single parameter (e.g., increased $k_{cat}$), or subsequent selections for different parameters (e.g., select for altered substrate specificity first, and then for increased $k_{cat}$ for the desired substrate). The skilled artisan will understand that there is no limit to the number of cycles of selection and library diversification, and that the methods provided herein can be used to achieve complex evolution processes with multiple mutations affecting multiple enzyme characteristics. The invention is not limited in this respect.

The simultaneous display of bond-forming enzyme and target substrate increases the effective concentration of these reaction partners, and, thus boosts screening efficiency. Conjugation of candidate bond-forming enzymes to surface proteins can be achieved by recombinant technologies well known to those of skill in the art, e.g., expression of the candidate enzyme as a fusion with a cell surface protein of the respective host cell, and expression of the target substrate as a fusion with a second cell surface protein of the same host cell. Alternatively, either or both the candidate enzyme and the target substrate may be conjugated to a cell surface protein post-translationally, e.g., via a reactive handle. Either or both the candidate enzyme and the target substrate may be conjugated to the respective cell surface protein via a linker, and in some embodiments the linker may be cleavable, e.g., via enzymatic or physical (e.g., UV light) cleavage.

Kits

Some aspects of this invention provide kits that comprise components useful for performing a method for the directed evolution of a bond-forming enzyme as described herein. In some embodiments, the kit comprises an expression vector into which a library of candidate bond-forming enzymes can be cloned to be expressed as a fusion with a cell surface protein, e.g., an Agap2 mating factor. In some embodiments, the kit also comprises reagents useful for screening a library of bond-forming enzymes, e.g., a substrate conjugated to a detectable label. In some embodiments, cells for expression and/or screening of the library of candidate bond-forming enzymes are also included.

Some aspects of this invention provide kits comprising an evolved, enhanced bond-forming enzyme (e.g., an evolved sortase as described herein), and reagents useful for carrying out a bond-forming reaction using the evolved enzyme. For example, in some embodiments, the kit may comprise a nucleic acid encoding an amino acid sequence recognized by the bond-forming enzyme, e.g., a C-terminal or N-terminal sortase recognition motif, that can be used to generate protein fusions in which a protein of interest carries a desired recognition motif. In some embodiments, an enzyme substrate conjugated to a detectable label is included.

The function and advantage of these and other embodiments of the present invention will be more fully understood from the Examples below. The following Examples are intended to illustrate the benefits of the present invention and to describe particular embodiments, but are not intended to exemplify the full scope of the invention. Accordingly, it will be understood that the Examples are not meant to limit the scope of the invention.

EXAMPLES

Materials and Methods

Sortase Evolution.

A library of $7.8 \times 10^7$ mutant sortase genes containing an average of 2.0 amino acid changes per gene was introduced into yeast cells using gap repair homologous recombination (see below for details on library construction). In Round 1, $6 \times 10^8$ sortase library-expressing cells were conjugated to GGGK-CoA (SEQ ID NO: 35), incubated with 100 μM biotin-LPETGS (SEQ ID NO: 36) for 60 minutes, and stained with streptavidin-PE and an AlexaFluor488-conjugated anti-HA antibody (Invitrogen). The top 1.4% of the PE/AlexaFluor488 double-positive population were isolated and grown to saturation. At least a tenfold excess of cells relative to the number of cells recovered from sorting were removed, pelleted, and induced to display enzymes at the cell surface with galactose before entering the subsequent round of sorting. See FIG. 11 for details on screening stringency. Following round 4, the surviving sortase genes were amplified by PCR and shuffled using the NeXT method (Muller K M, et al. (2005) Nucleotide exchange and excision technology (NExT) DNA shuffling: a robust method for DNA fragmentation and directed evolution. Nucleic Acids Res 33(13):e117). The diversified gene library was introduced into yeast to generate a library of $6.9 \times 10^7$ transformants. Four additional rounds of enrichment were performed with GGG immobilized on the surface and biotinylated LPETG (SEQ ID NO: 32) peptide provided exogenously. For rounds 9, 9mut, and 10mut, the cells from the previous round were modified with CoA-LPETGG (SEQ ID NO: 33) in TBS-B with 5 mM $MgCl_2$ and 5 mM $CaCl_2$ for 30 minutes to facilitate formation of the acyl-enzyme intermediate, before washing and initiating the reaction with 0.1-1.0 μM GGGYK-biotin (SEQ ID NO: 37).

Mammalian Cell Labeling.

HeLa cells were cultured at 37° C. in DMEM supplemented with 10% fetal bovine serum and 1% penicillin-streptomycin under an atmosphere containing 5% $CO_2$. The cells were transfected with a 9:1 ratio of plasmid pcDNA3-CD154-LPETG:cytoplasmic YFP expression plasmid (as a transfection marker) (SEQ ID NO: 32). After 24 hours, the transfected cells were trypsinized, re-plated onto glass coverslips, and incubated overnight at 37° C. Each coverslip was washed twice with Hank's balanced salt solution (HBSS) and immersed into HBSS supplemented with 1 mM GGGYK-biotin (SEQ ID NO: 37), 5 mM $CaCl_2$, and 100 μM enzyme. After 5 to 10 minutes, the coverslips were washed twice with PBS supplemented with 1% bovine serum albumin (BSA), 1 mM unmodified GGG, and 5 mM MgSO4 before immersion into a solution of streptavidin-AlexaFluor594 (1:200, Invitrogen) in PBS with 1% BSA and 5 mM MgSO4. For flow cytometry analysis, the coverslips were washed twice with PBS before incubation in PBS on ice for 30 minutes. Cells were resuspended and analyzed using a BD Fortessa flow cytometer. The AlexaFluor594 fluorescence of the top 16-25% most YFP-positive cells was recorded. For imaging, the coverslips were washed twice with PBS containing 5 mM MgSO4 before analysis on a Perkin Elmer spinning disk confocal microscope (Harvard Center for Biological Imaging). Images were recorded using the DIC, YFP, and Alexa channels.

Methods for Sortase Reactions on Yeast Cells and Model Screens

Sortase Reactions on Yeast with Biotinylated GGG Peptide.

Saccharomyces cerevisiae cells displaying Staphylococcus aureus sortase A and the S6 peptide (see below for details on induction of yeast display) were resuspended to a cell density of $2.5 \times 10^8$ cells/mL in Tris-buffered saline (pH 7.5) with 1 mg/mL bovine serum albumin (TBS-B) and 5 mM $MgCl_2$ and incubated with 6 µM Sfp and 5 µM CoA-LPETGG (SEQ ID NO: 33) (see below for synthesis details) for 15 minutes. Cells were pelleted and washed with TBS-B before resuspension to a cell density of $3 \times 10^6$ to $1 \times 10^7$ cells/mL in TBS-B with 5 mM $CaCl_2$ and 10 nM to 100 µM GGGYK-biotin peptide (SEQ ID NO: 37). After 15 to 60 minutes, the reactions were stopped by pelleting the cells and washing with ice-cold phosphate buffered saline with 1 mg/mL bovine serum albumin (PBS-B). The cells were washed with ice-cold PBS-B containing 500 µM AAEK2 (Astatech), an inhibitor of sortases (Maresso A W, et al. (2007) Activation of inhibitors by sortase triggers irreversible modification of the active site. J Biol Chem 282(32):23129-23139), and 100 µM unmodified GGG (Sigma) before incubation with streptavidin-phycoerythrin (streptavidin-PE) (Fluka) and AlexaFluor488-conjugated anti-hemagglutinin antibody (Invitrogen) to detect the extent of the sortase-catalyzed reaction and the enzyme display level, respectively. Cells were washed once more with PBS-B before flow cytometry analysis or FACS.

Sortase Reactions on Yeast with Biotinylated LPETG Peptide.

Yeast cells were conjugated to GGGK-CoA (SEQ ID NO: 35) (see below for synthesis details) and reacted with the biotinylated LPETG (SEQ ID NO: 32) peptide as described above. After stopping the reaction by centrifuging and washing, the cells were resuspended in TBS-B containing 5 µM TEV S219V protease (Kapust R B, et al. (2001) Tobacco etch virus protease: mechanism of autolysis and rational design of stable mutants with wild type catalytic proficiency. Protein Eng 14(12):993-1000) and incubated for 15-30 minutes to remove the background signal from the formation of any covalent acyl biotin-LPETG-enzyme (SEQ ID NO: 32) intermediate. After washing with cold PBS-B, the cells were stained with fluorophore-conjugated proteins as described above.

Model Screens.

Yeast displaying wild type sortase or the inactive C184A mutant were mixed in ratios of 1:1000 and 1:100 wt:C184A and treated as described above. After incubation with fluorophore conjugated proteins, $10^7$ cells from each mixture were sorted in a MoFlo cell sorter (DakoCytomation). The top 0.06% and top 0.7% of the PE/AlexaFluor488 double positive population for the 1:1000 and 1:100 experiments, respectively, were collected. Collected cells were cultured until saturation in growth media (see below) with 50 µg/mL carbenicillin, 25 µg/mL kanamycin, and 50 µg/mL streptomycin. Plasmid DNA was harvested using the Zymoprep kit (Zymo Research), and the recovered sortase genes were amplified using the primers 5'-CCCATAAACACACAGTATGTT (SEQ ID NO: 4) and 5'-AATTGAAATATGGCAGGCAGC (SEQ ID NO: 12) and digested with HindIII to determine the relative recovery of wild type and C184A genes.

Sortase Assay Methods

Flow Cytometry Activity Assay for Yeast Pools or Individual Yeast Clones.

A total of $1.25 \times 10^7$ yeast cells were resuspended in 50 µL of TBS-B containing 5 µM TEV S219V protease, 5 mM $MgCl_2$, and 5 mM $CaCl_2$. After incubation for 30 minutes at room temperature, the CoA-LPETGG (SEQ ID NO: 33) and GGGYK-biotin (SEQ ID NO: 37) peptides were added to the cell suspension to final concentrations of 5 µM and 25 µM, respectively. The cells were incubated at room temperature for an additional 30 minutes before Sfp was added to a final concentration of 6 µM. The cells were incubated at room temperature for 7 minutes, pelleted by centrifugation, and washed with ice-cold PBS-B. The cells were stained with fluorophore-conjugated proteins as described above, washed, and analyzed by flow cytometry.

In Vitro Sortase Kinetics Assays.

See below for details on sortase expression and purification, and on the synthesis of Abz-LPETGK(Dnp)-$CONH_2$ (SEQ ID NO: 48). Assays to determine $k_{cat}$ and $K_{m\ LPETG}$ were performed in 300 mM Tris pH 7.5, 150 mM NaCl, 5 mM $CaCl_2$, 5% v/v DMSO, and 9 mM Gly-Gly-Gly-COOH (GGG). The concentration of the LPETG (SEQ ID NO: 32) peptide substrate ranged from 12.5 µM to 10 mM, and enzyme concentrations ranged from 25 nM to 1000 nM. Assays for determination of $K_{m\ GGG}$ were performed under the same conditions, except the LPETG (SEQ ID NO: 32) peptide concentration was fixed at 1 mM, the enzyme concentration was fixed at 41.5 nM, and the concentration of GGG was varied from 33 µM to 30 mM, depending on the enzyme. Reactions were initiated with the addition of enzyme and incubated at 22.5° C. for 3 to 20 minutes before quenching with 0.5 volumes of 1 M HCl. Five to ten nmol of peptide from the quenched reactions were injected onto an analytical reverse-phase Eclipse XDB-C18 HPLC column (4.6×150 mm, 5 µm, Agilent Technologies) and chromatographed using a gradient of 10 to 65% acetonitrile with 0.1% TFA in 0.1% aqueous TFA over 13 minutes. Retention times under these conditions for the Abz-LPETGK(Dnp)-$CONH_2$ (SEQ ID NO: 48) substrate, the released GKDnp peptide, and the Abz-LPETGGG-COOH (SEQ ID NO: 34) product were 12.8, 10.4, and 9.1 min, respectively. To calculate the percent conversion, the ratio of the integrated areas of the Abz-LPETGGG-COOH (SEQ ID NO: 34) and Abz-LPETGK(Dnp)-$CONH_2$ (SEQ ID NO: 48) peptide Abs220 peaks was compared to a standard curve generated by mixing the product and starting peptide in known ratios. To determine $k_{cat}$ and $K_m$, reaction rates were fit to the Michaelis-Menten equation using OriginPro 7.0 software. All kinetics values reported represent the average of at least three measurements.

Substrate Synthesis Methods

Biotin-LC-LELPETGG-$CONH_2$ (SEQ ID NO: 49), Fmoc-GGGK-$CONH_2$ (SEQ ID NO: 35), and $NH_2$—YLEL-PETGG-$CONH_2$ (SEQ ID NO: 50) were purchased from Genscript and used without further purification. $NH_2$-GGGYK(biotin)-$CONH_2$ (SEQ ID NO: 37) was purchased from Genscript and purified using reverse-phase HPLC on a C18 column. Biotin-LCYGLPETGS-$CONH_2$ (SEQ ID NO: 52) was purchased from New England Peptide and used without further purification.

Synthesis of GGGK-CoA (SEQ ID NO: 35).

Fmoc-GGGK-CONH$_2$ (SEQ ID NO: 35) was dissolved in DMSO to a final concentration of 100 mM, and 1.5 equivalents of sulfo-SMCC (Thermo-Fisher) and 2 equivalents of DIPEA (Sigma) in DMSO were added. The reaction was incubated for 1 hr at room temperature, then added to 1.5 equivalents of coenzyme A trilithium hydrate (Sigma) in DMSO to a final peptide concentration of 25 mM and mixed at room temperature overnight. If appropriate, the Fmoc protecting group was removed with 20% vol/vol piperidine and incubation for 20 minutes. The reaction was quenched by the addition of 1 equivalent of TFA, and the product was purified on a preparative Kromasil 100-5-C18 column (21.2 ~250 mm, Peeke Scientific) by reverse phase HPLC (flow rate: 9.5 mL/min; gradient: 10% to 70% acetonitrile with 0.1% TFA in 0.1% aqueous TFA gradient over 30 minutes; retention time: 17.1 minutes). ESI-MS (found): [M-H]−m/z=1300.1. Calculated for C45H72N14O23P3S—: m/z=1301.4. The concentration of GGGK-CoA (SEQ ID NO: 35) peptide was determined from the measured A259 using the known molar extinction coefficient of coenzyme A, 15,000 M$^{-1}$ cm$^{-1}$ (Killenberg P G & Dukes D F (1976) Coenzyme A derivatives of bile acids-chemical synthesis, purification, and utilization in enzymic preparation of taurine conjugates. J Lipid Res 17(5): 451-455).

Synthesis of CoA-LPETGG (SEQ ID NO: 33) NH$_2$—YLELPETGG-CONH$_2$ (SEQ ID NO: 50) (0.0084 mmol) was incubated with sulfo-SMCC (0.021 mmol, 2.5 eq.) in 142 µL of DMSO and 3 µL DIPEA (0.017 mmol, 2.0 equivalents) for 2 hours at room temperature. The maleimide adduct was purified using reverse-phase HPLC on a preparative C18 column (flow rate: 9.5 mL/min; gradient: 10% to 60% acetonitrile with 0.1% TFA in 0.1% aqueous TFA over 30 minutes; retention time: 22.0 minutes). After lyophilization of the collected peak, the white solid was dissolved in 0.1 M phosphate buffer pH 7.0 with 45% acetonitrile. Coenzyme A trilithium hydrate (11.2 mg) was added, and the reaction was incubated at one hour at room temperature. The desired product was obtained after purification on a C18 column (flow rate: 9.5 mL/min flow rate; 0% to 50% acetonitrile in 0.1 M triethylammonium acetate over 30 minutes; retention time: 21.9 minutes). ESI-MS (found): [M-H]−m/z=1961.8. Calculated for C$_{77}$H$_{116}$N$_{18}$O$_{34}$P$_3$S—: m/z=1961.7. The concentration of CoA-LPETGG (SEQ ID NO: 33) peptide was determined as described above for GGGK-CoA (SEQ ID NO: 35).

Abz-LPETGK(Dnp)-CONH$_2$ Substrate for HPLC Assays (SEQ ID NO:48).

This compound was synthesized at 200 µmol scale using an Applied Biosystems 433A peptide synthesizer. 200 µmol-equivalents of NovaPEG Rink Amide resin (EMD biosciences) were loaded onto the machine and coupled using 5 equivalents of each Fmoc-protected amino acid building block with standard acid labile side-chain protecting groups (Thr(OtBu), Glu(OtBu)) and using Fmoc Lysine(Dnp) (Chem-Impex). Terminal coupling with Boc 2-Aminobenzoic Acid (Chem-Impex) yielded the fully protected peptide, which was cleaved by three 1-hour treatments with 20 mL of 95% TFA+2.5% water+2.5% triisopropylsilane (Sigma). The cleavage mixtures were pooled and concentrated by rotary evaporation, and the peptide was precipitated by the addition of 9 volumes of ice-cold diethyl ether. The samples were purified by reverse phase HPLC as described above for GGGK-CoA (SEQ ID NO: 35) (retention time: 28 minutes), pooled and concentrated by lyophilization. The concentration of the peptide was determined by the known molar extinction coefficient of the Dnp group, f$\overline{A}$355 nm=17,400 M-1 cm-1 (Carsten M E & Eisen H N (1953) The Interaction of Dinitrobenzene Derivatives with Bovine Serum Albumin. Journal of the American Chemical Society 75(18):4451-4456).

Cloning Methods Including Library Generation

Primers

| Primer | Sequence | SEQ ID |
|---|---|---|
| 1F | TCCAGACTATGCAGGATCTGAGAACTTGTACTTTCAAGGTGCTAGCCAAGCTAAACCTCA | 2 |
| 1R | CAGAAATAAGCTTTTGTTCGGATCCTTTGACTTCTGTAGCTACAAAG | 3 |
| 2F | CCCATAAACACACAGTATGTT | 4 |
| 2R | ACCTTGAAAGTACAAGTTCTCAGATCCTGCATAGTCTGGAACGTCGT | 5 |
| 3F | AAAGATAAACAATTAACATTAATTACTGCTGATGATTACAATGAA | 6 |
| 3R | ATCTCGAGCTATTACAAGTCCTCTTCAGAAATAAGCTTTTGTTCGGA | 7 |
| 4F | GTGGAGGAGGCTCTGGTGGAGGCGGTAGCGGAGGCGGAGGGT | 8 |
| 4R | AGTAATTAATGTTAATTGTTTATCTTT | 9 |
| 5F | TGGGAATTCCATATGCAAGCTAAACCTCAAATTCCG | 10 |
| 5R | TTTTTTCTCGAGTTTGACTTCTGTAGCTACAAAG | 11 |
| 6R | AATTGAAATATGGCAGGCAGC | 12 |
| 7F | CCAGGACCAGCAACAAGYGAACAATTAAATAGA | 13 |
| 8F | ATGACAAGTATAAGAAAYGTTAAGCCAACAGCKGTAGAAGTTCTAGAT | 14 |
| 9F | TTAATTACTTGTGATGGKTACAATGAAAAGACA | 15 |

Y = C, T; K = G, T; underlined nucleotides represent mixtures of 70% the indicated nucleotide and 10% each of the remaining three nucleotides YIPlac211-GPD-S6-Aga1p and Integration Into the Yeast Genome. The YIPlac211-GPD-Avitag-Aga1p plasmid, constructed by ligation of the Avitag-Aga1p gene into YIPlac211 (ATCC) at BamHI/SacI and ligation of the glyceraldehyde-3-phosphate dehydrogenase (GPD) promoter sequence at XbaI/BamHI, served as the starting point. The S6 peptide sequence was inserted after the signal sequence and before 11e30 of Aga1p by overlap extension PCR. The extended PCR product was digested with BamHI and BsiWI and ligated into similarly digested YIPlac211-GPD-Avitag-Aga1p plasmid, resulting in the yeast integrating plasmid YIPlac211-GPDS6-Aga1p.

To integrate the plasmid into the genome, YIPlac211-GPD-S6-Aga1p was linearized by digestion with BsiWI and transformed into S. cerevisiae strain BJ5465 with lithium acetate, selecting for transformants harboring the integrated plasmid on solid media lacking uracil. A yeast colony with the S6-Aga1p construct correctly inserted was designated ICY200 and displays the S6 peptide sequence constitutively on the cell surface as a fusion to the N-terminus of Aga1p.

pCTCon2CTEV-wt srtA and pCTCon2CTEV-srtA C184A (.HindIII).

The pCTCon2CTEV-wt srtA plasmid was constructed inside yeast through a three-part, gap repair homologous recombination process (Raymond C K, Pownder T A, & Sexson S L (1999) General method for plasmid construction using homologous recombination. BioTechniques 26(1):134-138, 140-131). The pCTCon2B-BirA plasmid, which was constructed from pCTCon2 and expresses the Aga2p-linker-HA-E. coli biotin ligase-myc construct, served as the starting point. S. aureus genomic DNA was amplified with primers 1F and 1R, and pCTCon2B-BirA with primers 2F and 2R. These two products were transformed together with PstI/BamHI-digested pCTCon2B-BirA into S. cerevisiae strain ICY200 to yield the pCTCon2CTEV-wt srtA plasmid. The cloned sortase A gene lacks the N-terminal 59 amino acids, which do not impact catalytic activity (Ilangovan U, Ton-That H, Iwahara J, Schneewind O, & Clubb R T (2001) Structure of sortase, the transpeptidase that anchors proteins to the cell wall of Staphylococcus aureus. Proc Natl Acad Sci USA 98(11):6056-606), but these amino acids are still included in the numbering for the mutations.

To introduce the C184A mutation, pCTCon2CTEV-wt srtA was separately amplified with primer pairs 3F/3R and 4F/4R, and the two gene fragments were transformed into ICY200 together with NheI/BamHI-digested pCTCon2CTEV-wt srtA. The HindIII site within the myc coding sequence was then removed using an analogous process, allowing the wt and C184A plasmids to be distinguished by a HindIII restriction digest.

pET29 Sortase Expression Plasmids

Sortase genes were subcloned into pET29 at NdeI and XhoI using the primers 5F and 5R. Plasmids encoding sortase single mutants were constructed using the Quikchange method. All expressed sortases lack the N-terminal 59 amino acids.

Sortase A Library R0.

The round zero (R0) sortase A library was cloned into S. cerevisiae ICY200 using gap repair homologous recombination. The wild type sortase A gene, lacking the N-terminal 59 amino acids, was mutagenized in PCR reactions containing 5 µM 8-oxo-2 fdeoxyguanosine (8-oxo-dGTP), 5 µM 6-(2-deoxy-b-D-ribofuranosyl)-3,4-dihydro-8H-pyrimido-[4,5-C][1,2]oxazin-7-one (dPTP), 200 µM each dNTP, and 0.4 µM each of primers 1F and 1R. Reactions were thermocycled ten times and the mutagenized genes were further amplified in PCR reactions without mutagenic dNTP analogs using primers 1F and 3R. Gel-purified genes and NheI/BamHI-digested pCTCon2CTEV-wt srtA were combined in a 1:3 mass ratio, concentrated by ethanol precipitation, and electroporated into competent ICY200 as described, resulting in a library of $7.8 \times 10^7$ transformants. A total of $\sim 10^9$ cells from the fully grown library culture were pelleted and induced as described below.

Recombined Sortase A Library (R4shuf).

In vitro recombination was performed using the NExT procedure (1). Sortase genes recovered after R4 were amplified with the primers 2F and 6R in PCR reactions containing 50 µM dUTP, 150 µM dTTP, and 200 µM each of dATP, dCTP, and dGTP. After purification by gel extraction, 17 µg of the PCR product was incubated with 7.5 units of uracil deglycosylase (NEB). Piperidine was added (10% vol/vol) and the reaction was heated at 90° C. for 3 min. The resulting gene fragments were purified using the QiaExII kit after neutralization of the piperidine with glacial acetic acid.

Fragments were assembled in PCR reactions containing 1 µg of fragments using the conditions reported by Tawfik (Herman A & Tawfik D S (2007) Incorporating Synthetic Oligonucleotides via Gene Reassembly (ISOR): a versatile tool for generating targeted libraries. Protein Eng Des Sel 20(5):219-226). In separate fragment assembly reactions, primers 7F, 8F, and 9F were each added to the assembly reaction at 0.5 µM and 1.5 µM to favor the inclusion of P94S, D160N, D165A, and D186G. mutations that appeared to improve catalytic efficiency based on activity assays of individual clones evolved in R3 and R4. Assembly reactions were purified using the Qiaquick kit, reamplified with the primers 1F and 1R, and purified by gel extraction. Eight µg of each assembled gene product (24 µg total) were mixed with 7 µg of NheI/BamHI-digested pCTCon2CTEV plasmid, concentrated by ethanol precipitation, and electroporated into competent ICY200 cells as described above, resulting in a library of $6.9 \times 10^7$ transformants. A total of $\sim 10^9$ cells from the fully grown library culture were pelleted and induced as described below.

Sortase Library R8mut.

Figure 13:
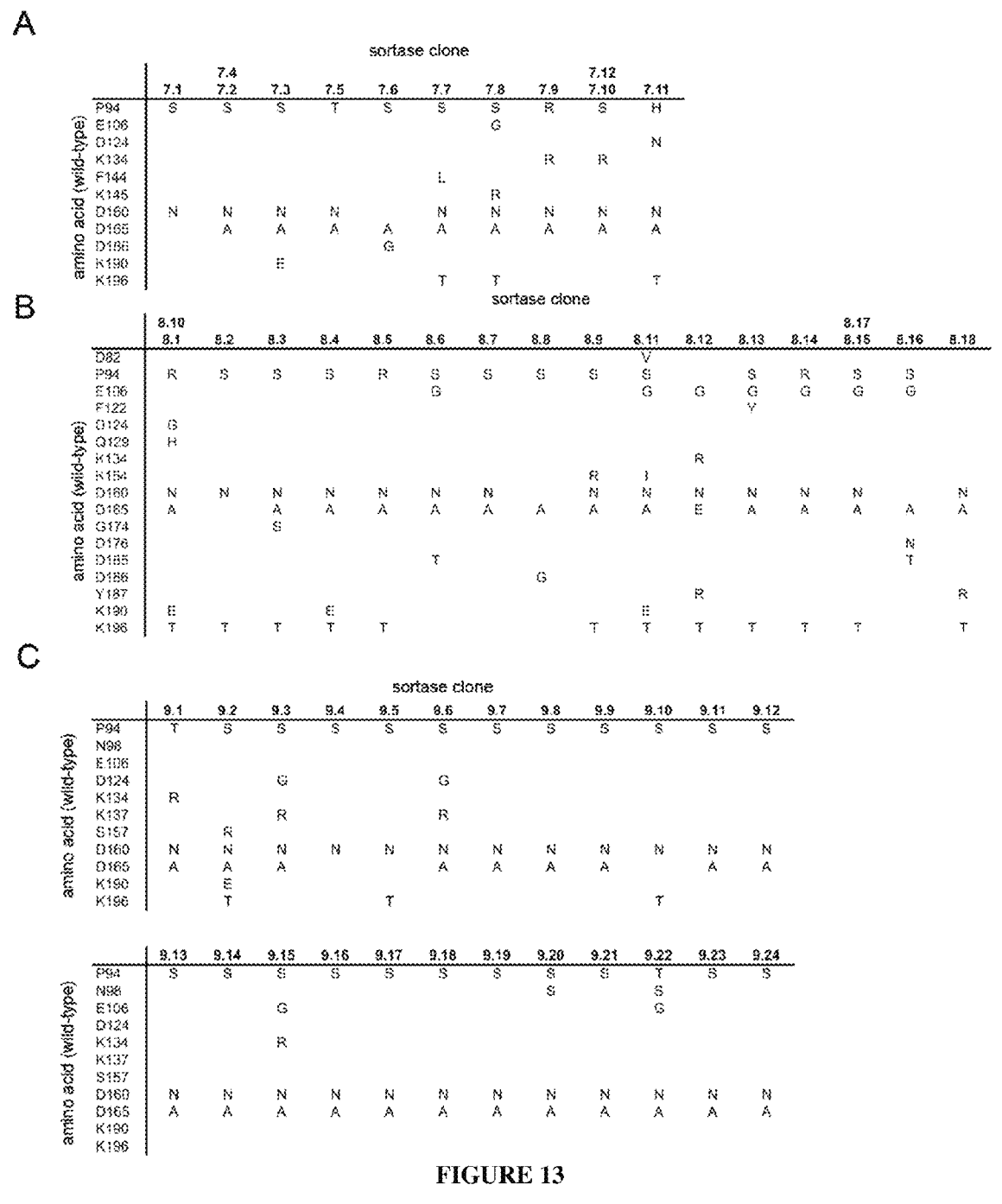

The R8mut library was cloned into yeast as described above for the R0 library, starting with an equimolar mixture of the genes encoding clones 8.3, 8.4, 8.5, and 8.9 (see FIG. 13). These clones were chosen because they possessed only one extraneous mutation in addition to the tetramutant motif (8.3, 8.4, 8.9), or because they possessed an altered tetramutant core (8.5). More heavily mutagenized library members (8.11, 8.13) were avoided in order to minimize deviation from the tetramutant core of mutations. The concentrations of dPTP and 8-oxo-dGTP were each 10 µM. Following electroporation into ICY200 as described above, a library of $5 \times 10^7$ transformants was obtained with a bulk mutagenesis rate of 1.5%, corresponding with an amino acid mutagenesis rate of 1.1%.

General Yeast Methods

Yeast cells were transformed with DNA using the lithium acetate method. Plasmid DNA from yeast cultures was harvested using the Zymoprep Yeast Plasmid Minipreparation Kit (Zymo Research) following the manufacturer's instructions. For sequencing, zymoprepped DNA was amplified by transformation into E. coli, or sortase genes were amplified by PCR using the primers 2F and 6R.

S. cerevisiae strain ICY200 was propagated in YPD or growth media consisting of 100 mM phosphate pH 6.6, 2% (w/v) dextrose, 0.67% yeast nitrogen base (Sigma), 100 µg/mL cysteine, 100 µg/mL proline, 30 µg/mL histidine, 30 µg/mL methionine, and complete supplement mixture lacking uracil (MP Biomedical). Growth media for ICY200 transformed with the pCTCon2CTEV yeast display plasmids was the same, except the complete supplement mixture lacked uracil and tryptophan. Induction media was the same as the growth media lacking uracil and tryptophan, except the carbon source consisted of 1.8% galactose and 0.2% dextrose. For induction of display of sortases on the cell surface, yeast cells from a fully grown culture were pelleted, resuspended in induction media at a density of $7\times10^6$ cells/mL, and incubated at 20° C. for 18-36 hours. Cells were pelleted and washed with TBS supplemented with 1 mg/mL BSA (TBS-B) before input into assays.

Protein Expression and Purification

Bacterial Expression of Sortases.

E. coli BL21(DE3) transformed with pET29 sortase expression plasmids were cultured at 37° C. in LB with 50 µg/mL kanamycin until OD600=0.5-0.8. IPTG was added to a final concentration of 0.4 mM and protein expression was induced for three hours at 30° C. The cells were harvested by centrifugation and resuspended in lysis buffer (50 mM Tris pH 8.0, 300 mM NaCl supplemented with 1 mM $MgCl_2$, 2 units/mL DNAseI (NEB), 260 nM aprotinin, 1.2 µM leupeptin, and 1 mM PMSF). Cells were lysed by sonication and the clarified supernatant was purified on Ni-NTA agarose following the manufacturer's instructions. Fractions that were >95% purity, as judged by SDS-PAGE, were consolidated and dialyzed against Tris-buffered saline (25 mM Tris pH 7.5, 150 mM NaCl). Enzyme concentration was calculated from the measured A280 using the published extinction coefficient of 17,420 M-1 cm-1 (Kruger R G, et al. (2004) Analysis of the substrate specificity of the Staphylococcus aureus sortase transpeptidase SrtA. Biochemistry 43(6):1541-1551).

Bacterial Expression of Sfp Phosphopantetheinyl Transferase.

E. coli BL21(DE3) harboring the pET29 expression plasmid for Sfp phosphopantetheinyl transferase (a gift from the Christopher T. Walsh lab) were cultured at 37° C. in LB with 50 µg/mL kanamycin until OD600 ~0.6. IPTG was added to a final concentration of 1 mM, and protein expression was induced at 37° C. for three hours. The cells were harvested by centrifugation and lysed by resuspension in B-PER (Novagen) containing 260 nM aprotinin, 1.2 µM leupeptin, 2 units/mL DNAseI, and 1 mM PMSF. The clarified supernatant was purified on Ni-NTA agarose, and fractions that were >95% pure were consolidated and dialyzed against 10 mM Tris pH 7.5+1 mM EDTA+5% glycerol. Enzyme concentration was calculated from the measured A280 using the published extinction coefficient of 27,220 $M^{-1}$ $cm^{-1}$ (Mofid M R, Finking R, Essen L O, & Marahiel M A (2004) Structure-based mutational analysis of the 4'-phosphopantetheinyl transferases Sfp from Bacillus subtilis: carrier protein recognition and reaction mechanism. Biochemistry 43(14):4128-4136).

Bacterial Expression of TEV S219V Protease.

E. coli BL21(DE3) harboring the pRK793 plasmid for TEV S219V expression and the pRIL plasmid (Addgene) were cultured in LB with 50 µg/mL carbenicillin and 30 µg/mL chloramphenicol until OD600 ~0.7. IPTG was added to a final concentration of 1 mM, and the cells were induced for three hours at 30° C. The cells were pelleted by centrifugation and lysed by sonication as described above for the sortases. The clarified lysate was purified on Ni-NTA agarose, and fractions that were >95% TEV S219V were consolidated and dialyzed against TBS. Enzyme concentration was calculated from the measured A280 using the reported extinction coefficient of 32,290 M-1 cm-1 (Tropea J E, Chemy S, & Waugh D S (2009) Expression and purification of soluble His(6)-tagged TEV protease. Methods Mol Biol 498:297-307).

Protein Sequences

Amino acid changes relative to wild type S. aureus sortase A are underlined. Some sequences are displayed with C-terminal 6×His tag. Sequences without the 6×His tag are also functional and are provided by the sequences below as well.

Figure 2:
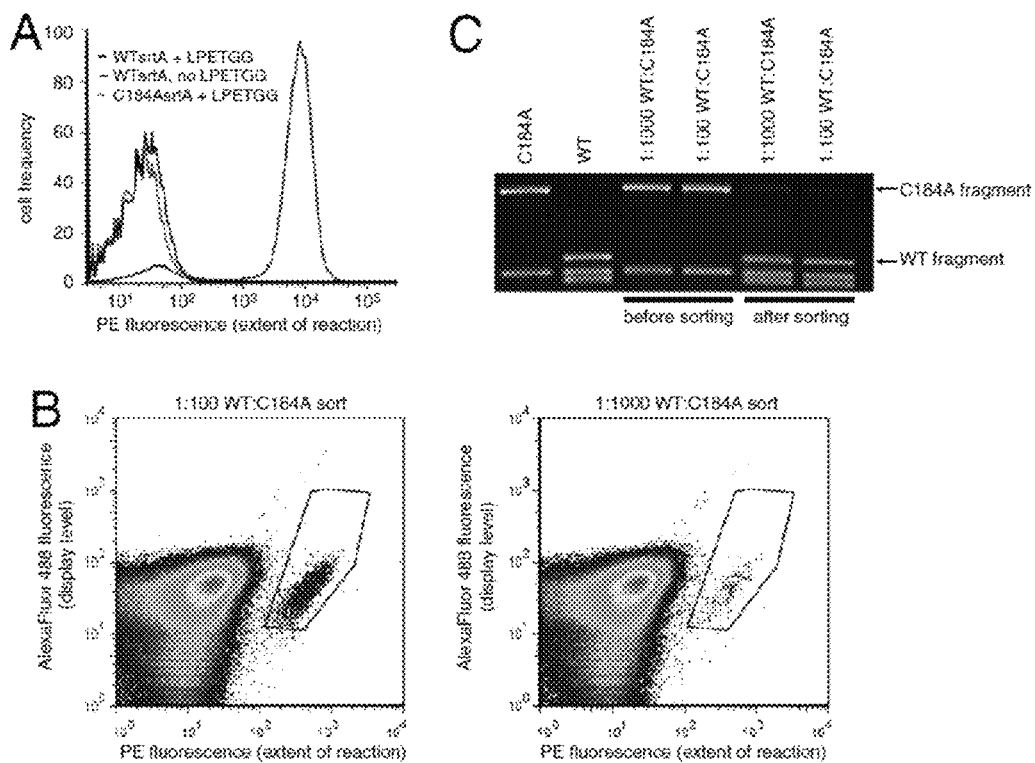
FIG. 2. Validation of the enzyme evolution strategy. (A) FACS histogram of the reaction between cell surface-conjugated LPETGG (SEQ ID NO: 33) and free GGGYK-biotin (SEQ ID NO: 37) catalyzed by yeast-displayed wild type *S. aureus* sortase A (wild type srtA). Cells were stained with streptavidin-PE and an AlexaFluor488-anti-HA antibody. Negative control reactions with either the inactive C184A srtA mutant or without LPETGG (SEQ ID NO: 33) are shown. (B) Dot plots comparing PE fluorescence (extent of reaction) vs. AlexaFluor488 fluorescence (display level) for two model screens. Mixtures of cells displaying either wild type srtA or the inactive C184A srtA (1:1;000 and 1:100 wild type:C184A) were processed as in A, then analyzed by FACS. Cells within the specified gate (black polygon) were collected. (C) Model screening results. Gene compositions before and after sorting were compared following HindIII digestion, revealing strong enrichment for active sortase.

```
Aga2p-srtA C1 84A (FIG. 2, FIG. 3B)
                                                  (SEQ ID NO: 16)
MQLLRCFSIFSVIASVLAQELTTICEQIPSPTLESTPYSLSTTTILANGKAMQGVFEYYKSV
TFVSNCGSHPSTTSKGSPINTQYVFKDNSSTLQASGGGGSGGGGSGGGGSYPYDVPDYA
GSENLYFQGASQAKPQIPKDKSKVAGYIEIPDADIKEPVYPGPATPEQLNRGVSFAEENE
SLDDQNISIAGHTFIDRPNYQFTNLKAAKKGSMVYFKVGNETRKYKMTSIRDVKPTDVE
VLDEQKSKDKQLTLITADDYNEKTGVWEKRKIFVATEVKGSEQKLISEEDL Aga2p-Clone 8.3 (FIG. 3B, FIG. 4A)
                                                  (SEQ ID NO: 17)
MQLLRCFSIFSVIASVLAQELTTICEQIPSPTLESTPYSLSTTTILANGKAMQGVFEYYKSV
TFVSNCGSHPSTTSKGSPINTQYVFKDNSSTLQASGGGGSGGGGSGGGGSYPYDVPDYA
GSENLYFQGASQAKPQIPKDKSKVAGYIEIPDADIKEPVYPGPATSEQLNRGVSFAEENE
SLDDQNISIAGHTFIDRPNYQFTNLKAAKKGSMVYFKVGNETRKYKMTSIRNVKPTAVE
VLDEQKSKDKQLTLITCDDYNEKTGVWETRKIFVATEVKGSEQKLISEEDL Aga2p-Clone 8.4 (FIG. 3B, FIG. 4A)
                                                  (SEQ ID NO: 18)
MQLLRCFSIFSVIASVLAQELTTICEQIPSPTLESTPYSLSTTTILANGKAMQGVFEYYKSV
TFVSNCGSHPSTTSKGSPINTQYVFKDNSSTLQASGGGGSGGGGSGGGGSYPYDVPDYA
GSENLYFQGASQAKPQIPKDKSKVAGYIEIPDADIKEPVYPGPATSEQLNRGVSFAEENE
SLDDQNISIAGHTFIDRPNYQFTNLKAAKKGSMVYFKVGNETRKYKMTSIRNVKPTAVE
VLDEQKSKDKQLTLITCDDYNEETGVWETRKIFVATEVKGSEQKLISEEDL Aga2p-Clone 8.9 (FIG. 3B, FIG. 4A)
                                                  (SEQ ID NO: 19)
MQLLRCFSIFSVIASVLAQELTTICEQIPSPTLESTPYSLSTTTILANGKAMQGVFEYYKSV
TFVSNCGSHPSTTSKGSPINTQYVFKDNSSTLQASGGGGSGGGGSGGGGSYPYDVPDYA
GSENLYFQGASQAKPQIPKDKSKVAGYIEIPDADIKEPVYPGPATSEQLNRGVSFAEENE
SLDDQNISIAGHTFIDRPNYQFTNLKAAKKGSMVYFKVGNETRKYRMTSIRNVKPTAVE
VLDEQKSKDKQLTLITCDDYNEKTGVWETRKIFVATEVKGSEQKLISEEDL
```

-continued

Aga2p-Clone 8.13 (FIG. 3B, FIG. 4A)
(SEQ ID NO: 20)
MQLLRCFSIFSVIASVLAQELTTICEQIPSPTLESTPYSLSTTTILANGKAMQGVFEYYKSV
TFVSNCGSHPSTTSKGSPINTQYVFKDNSSTLQASGGGGSGGGGSGGGGSYPYDVPDYA
GSENLYFQGASQAKPQIPKDKSKVAGYIEIPDADIKEPVYPGPATSEQLNRGVSFAEGNE
SLDDQNISIAGHTYIDRPNYQFTNLKAAKKGSMVYFKVGNETRKYKMTSIRNVKPTAVE
VLDEQKSKDKQLTLITCDDYNEKTGVWETRKIFVATEVKGSEQKLISEEDL wild type S. aureus sortase A (FIG. 3B, FIG. 4A, Table 1)
(SEQ ID NO: 21)
MQAKPQIPKDKSKVAGYIEIPDADIKEPVYPGPATPEQLNRGVSFAEENESLDDQNISIAG
HTFIDRPNYQFTNLKAAKKGSMVYFKVGNETRKYKMTSIRDVKPTDVEVLDEQKGKD
KQLTLITCDDYNEKTGVWEKRKIFVATEVKLEHHHHHH srtA P94S (Table 1)
(SEQ ID NO: 22)
MQAKPQIPKDKSKVAGYIEIPDADIKEPVYPGPATSEQLNRGVSFAEENESLDDQNISIAG
HTFIDRPNYQFTNLKAAKKGSMVYFKVGNETRKYKMTSIRDVKPTDVEVLDEQKGKD
KQLTLITCDDYNEKTGVWEKRKIFVATEVKLEHHHHHH srtA D160N (Table 1)
(SEQ ID NO: 23)
MQAKPQIPKDKSKVAGYIEIPDADIKEPVYPGPATPEQLNRGVSFAEENESLDDQNISIAG
HTFIDRPNYQFTNLKAAKKGSMVYFKVGNETRKYKMTSIRNVKPTDVEVLDEQKGKD
KQLTLITCDDYNEKTGVWEKRKIFVATEVKLEHHHHHH srtA D165A (Table 1)
(SEQ ID NO: 24)
MQAKPQIPKDKSKVAGYIEIPDADIKEPVYPGPATPEQLNRGVSFAEENESLDDQNISIAG
HTFIDRPNYQFTNLKAAKKGSMVYFKVGNETRKYKMTSIRDVKPTAVEVLDEQKGKD
KQLTLITCDDYNEKTGVWEKRKIFVATEVKLEHHHHHH srtA K196T (Table 1)
(SEQ ID NO: 25)
MQAKPQIPKDKSKVAGYIEIPDADIKEPVYPGPATPEQLNRGVSFAEENESLDDQNISIAG
HTFIDRPNYQFTNLKAAKKGSMVYFKVGNETRKYKMTSIRDVKPTDVEVLDEQKGKD
KQLTLITCDDYNEKTGVWETRKIFVATEVKLEHHHHHH Clone 4.2 (FIG. 3B, FIG. 4A, Table 1)
(SEQ ID NO: 26)
MQAKPQIPKDKSKVAGYIEIPDADIKEPVYPGPATPEQLNRGVSFAEENESLDDQNISIAG
HTFIDRPNYQFTNLKAAKKGSMVYFKVGNETRKYKMTSIRNVKPTDVEVLDEQKGKD
KQLTLITCDDYNEETGVWETRKIFVATEVKLEHHHHHH Clone 4.3 (FIG. 3B, FIG. 4A, Table 1)
(SEQ ID NO: 27)
MQAKPQIPKDKSKVAGYIEIPDADIKEPVYPGPATSEQLNRGVSFAEENESLDDQNISIAG
HTFIDRPNYQFTNLKAAKKGSMVYFKVGNETRKYKMTSIRDVKPTAVEVLDEQKGKD
KQLTLITCDDYNEKTGVWEKRKIFVATEVKLEHHHHHH P94S/D160N/D165A/K196T (Table 1)
(SEQ ID NO: 28)
MQAKPQIPKDKSKVAGYIEIPDADIKEPVYPGPATSEQLNRGVSFAEENESLDDQNISIAG
HTFIDRPNYQFTNLKAAKKGSMVYFKVGNETRKYKMTSIRNVKPTAVEVLDEQKGKD
KQLTLITCDDYNEKTGVWETRKIFVATEVKLEHHHHHH P94S/D160N/K196T (Table 1, FIG. 5)
(SEQ ID NO: 29)
MQAKPQIPKDKSKVAGYIEIPDADIKEPVYPGPATSEQLNRGVSFAEENESLDDQNISIAG
HTFIDRPNYQFTNLKAAKKGSMVYFKVGNETRKYKMTSIRNVKPTDVEVLDEQKGKD
KQLTLITCDDYNEKTGVWETRKIFVATEVKLEHHHHHH P94S/D160N/D165A (Table 1)
(SEQ ID NO: 30)
MQAKPQIPKDKSKVAGYIEIPDADIKEPVYPGPATSEQLNRGVSFAEENESLDDQNISIAG
HTFIDRPNYQFTNLKAAKKGSMVYFKVGNETRKYKMTSIRNVKPTAVEVLDEQKGKD
KQLTLITCDDYNEKTGVWEKRKIFVATEVKLEHHHHHH P94R/D160N/D165A/K190E/K196T (Table 1)
(SEQ ID NO: 31)
MQAKPQIPKDKSKVAGYIEIPDADIKEPVYPGPATREQLNRGVSFAEENESLDDQNISIAG
HTFIDRPNYQFTNLKAAKKGSMVYFKVGNETRKYKMTSIRNVKPTAVEVLDEQKGKD
KQLTLITCDDYNEETGVWETRKIFVATEVKLEHHHHHH Effective Molarity of Surface-Conjugated Substrate Relative to Yeast-Displayed Sortase Yeast displaying clones 4.2 and 4.3 were conjugated with GGGK-CoA (SEQ ID NO: 35) as described in the Materials and Methods section. The resulting cells were incubated with 1 μM Biotin-LPETGG (SEQ ID NO: 33) in TBS with 5 mM CaCl$_2$, and aliquots were removed at various time points and immediately diluted 1:20 into ice-cold PBS containing 6 μM TEV S219V, 5 mM AAEK2 (an inhibitor of S. aureus sortase A (2)), 1 mM berberine chloride (an inhibitor of S. aureus sortase A (Kim S H, et al. (2004) Inhibition of the bacterial surface protein anchoring transpeptidase sortase by isoquinoline alkaloids. Biosci Biotechnol Biochem 68(2):421-424)), and 5 mM of non-biotinylated GGG.

After incubation on ice for fifteen minutes, the samples were pelleted and resuspended in ice-cold PBS containing 6 µM TEV S219V, 5 mM AAEK2, 5 mM GGG for one hour. Following staining of the cells with streptavidin-phycoerythrin (for reaction extent) and AlexaFluor488-conjugated anti-hemagglutinin antibody (for display), the phycoerythrin mean fluorescence intensity (PE MFI) of the AlexaFluor488-positive cells were recorded with a BD Fortessa flow cytometer. When plotted versus time (t), the PE MFI (for reaction extent) for the 488/PE-double positive population of each sample were fit to the Poisson equation representing the proportion of sites converted for a reaction operating at constant velocity v, $f_{\infty}(1-e^{-v*(t+theta)})+f_0$. The scaling factor $f_{\infty}$ is taken to represent the fluorescence intensity of a fully labeled cell and is determined by allowing reactions to run for two hours and fixing this as the endpoint. The minimum fluorescence intensity for a library member, $f_0$, is fixed from the PE MFI of 488-negative cells within the population. The velocity of the reaction, v, and the time correction factor, theta, were both determined by nonlinear regression of the data to the fit curve using the program Mathematica. The velocity data were then transformed into estimates for the effective molarity of displayed enzymes for [GGG] by the use of the previously determined Michaelis-Menten relations for clones 4.2 and 4.3, $[GGG]=K_{m,GGG}*K_{m,LPETG}*v+K_{m,GGG}*[LPETG]*v/(k_{cat}*[LPETG]-K_{m,LPETG}*v-[LPETG]*v)$ [GGG] estimates were made for two technical replicates each of the 4.2 and 4.3 sortase mutants, and the overall estimate of [GGG] was found to be 0.95±0.11 mM; the LPETG sequence of the equation corresponds to SEQ ID NO: 32).

Results

The evolution strategy provided herein was validated using model screens for *Staphylococcus aureus* sortase A-catalyzed transpeptidation activity, resulting in enrichment factors of 6,000-fold after a single round of screening. The strategy provided herein was applied to evolve sortase A for improved catalytic activity. After eight rounds of screening, we isolated variants of sortase A with up to a 140-fold increase in LPETG-coupling (SEQ ID NO: 32) activity compared with the starting wild type enzyme. An evolved sortase variant enabled much more efficient labeling of LPETG-tagged (SEQ ID NO: 32) human CD154 expressed on the surface of HeLa cells compared with wild type sortase.

Design and Implementation of a General System for the Evolution of Bond-Forming Enzymes.

The enzyme evolution system is overviewed in FIG. 1. Yeast cells display the enzyme library extracellularly as a fusion to the Aga2p cell surface mating factor, which is covalently bound to the Aga1p mating factor with a reactive handle that enables covalent attachment of substrate A to cells. We chose the S6 peptide (3) as the reactive handle to link substrate A to cells using Sfp phosphopantetheinyl transferase from *Bacillus subtilis*. Substrate B linked to an affinity handle (e.g., biotin, represented by the gray circle in FIG. 1) is added to the substrate A-conjugated yeast display enzyme library. Because of the high effective molarity of substrate A with respect to each cell's displayed library member, both of which are immobilized on the cell surface, active library members will predominantly catalyze the pseudointramolecular A-B bond formation between affinity handle-linked substrate B and substrate A molecules on their own host cell. The intermolecular coupling of substrate B with substrate A molecules attached to other cells is entropically much less favorable, and therefore yeast cells displaying inactive enzymes should remain predominantly uncoupled to the affinity handle.

Following incubation with substrate B for the desired reaction time, cells are stained with a fluorescent molecule that binds the affinity handle [e.g., streptavidin-phycoerythrin (streptavidin-PE)]. The most fluorescent cells, which encode the most active catalysts, are isolated by FACS. Up to $10^8$ cells can be sorted in a 2-h period using modern FACS equipment. After sorting and growth amplification, the recovered cells can be enriched through additional FACS steps, or DNA encoding active library members can be harvested and subjected to point mutagenesis or recombination before entering the next round of evolution.

Figure 6:
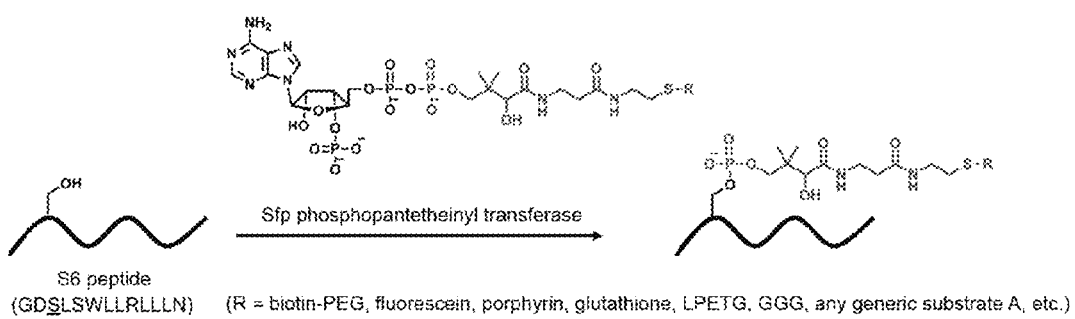
FIG. 6. Sfp-catalyzed transfer of phosphopantetheinyl derivatives (blue) onto a specific serine residue (underlined) within the S6 peptide sequence (SEQ ID NO: 53).

We used a chemoenzymatic approach to link substrate A to cells rather than a nonspecific chemical conjugation strategy to more reproducibly array the substrate on the cell surface and to avoid reagents that might alter the activity of library members. The *B. subtilis* Sfp phosphopantetheinyl transferase catalyzes the transfer of phosphopantetheine from coenzyme A (CoA) onto a specific serine side chain within an acyl carrier protein or peptide carrier protein. We chose Sfp to mediate substrate attachment because of its broad small-molecule substrate tolerance (3, 21) and its ability to efficiently conjugate phosphopantetheine derivatives to the 12-residue S6 peptide (22) (FIG. 6). We speculated that the small size of the S6 peptide would allow it to be well tolerated in the context of the Aga1p mating factor. Functionalized CoA derivatives can be readily prepared by reacting the free thiol of commercially available CoA (3, 21) with a commercially available maleimide-containing bifunctional crosslinker, followed by substrate A bearing a compatible functional group.

Figure 7:
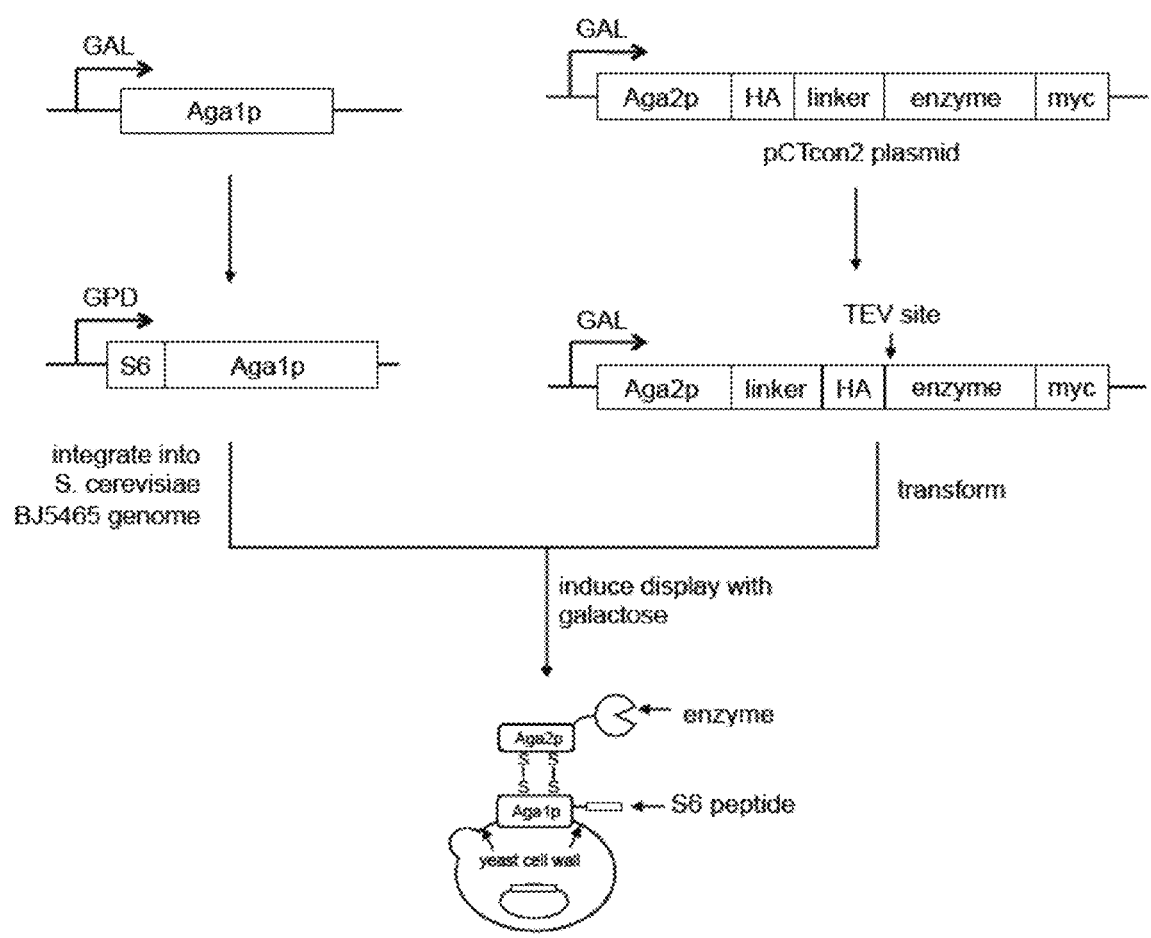
FIG. 7. Engineering a *Saccharomyces cerevisiae* strain that simultaneously displays the S6 peptide sequence and the sortase library on its cell surface. The S6-Aga1p construct is cloned under the control of the constitutive glyceraldehyde-3-phosphate dehydrogenase (GPD) promoter and integrated into the genome of *S. cerevisiae* BJ5465 to yield strain ICY200. Through several cloning steps, a TEV recognition site is inserted between the HA tag and enzyme gene of the Aga2p fusion construct. Yeast display of sortases is induced upon the addition of galactose to the media.

To integrate Sfp-catalyzed bioconjugation with yeast display required engineering a yeast display vector and yeast strain (FIG. 7). To create a handle for substrate attachment at the cell surface, we fused the S6 peptide onto the N-terminus of Aga1p and integrated this construct under the control of the strong, constitutive GPD promoter in the genome of *Saccharomyces cerevisiae* strain BJ5465 (19). We modified the Aga2p expression construct by inserting the recognition site for tobacco etch virus (TEV) protease between the hemagglutinin (HA) tag and the coding sequence of the protein of interest. Following incubation of the substrate A-conjugated yeast library with substrate B, TEV protease digestion removes all library members from the surface, including any undesired enzymes that bind or react directly with substrate B but do not catalyze A-B bond formation, thus removing a potential source of undesired background. The HA tag remains on the cell surface and enables staining for enzyme display level using an anti-HA antibody. The ability to efficiently cleave enzymes from the yeast cell surface also facilitates enzyme characterization in a cell-free context.

Validation of the Yeast Display System.

Sortase A (srtA) is a sequence-specific transpeptidase found in *Staphylococcus aureus* and other Gram-positive bacteria. The *S. aureus* enzyme recognizes an LPXTG (SEQ ID NO: 51) site (X represents any amino acid), cleaves the scissile amide bond between threonine and glycine using a nucleophilic cysteine (C184), and resolves the resulting acyl-enzyme intermediate with oligoglycine-linked molecules to generate the fusion of the LPXT- and oligoglycine-linked peptides or proteins. Sortase A-catalyzed transpeptidation has emerged as a powerful tool for bioconjugation because of the enzyme's high specificity for the LPXTG (SEQ ID NO: 51) motif and its extremely broad substrate tolerance outside of the recognition elements described above. Because the LPXTG (SEQ ID NO: 51) and oligoglycine motifs can be flanked by virtually any biomolecule, sortase has been used to label proteins, generate nucleic acid-protein conjugates, and immobilize proteins onto solid supports (23). A significant limitation of srtA is the large quantities of the enzyme or long reaction times that are needed to overcome its poor reaction kinetics ($k_{cat}/K_{m\,LPETG}$=200 M$^{-1}$ s$^{-1}$; Table 1). The evolution of a more active S. aureus srtA would therefore significantly enhance the utility and scope of this bond-forming reaction.

Figure 8:
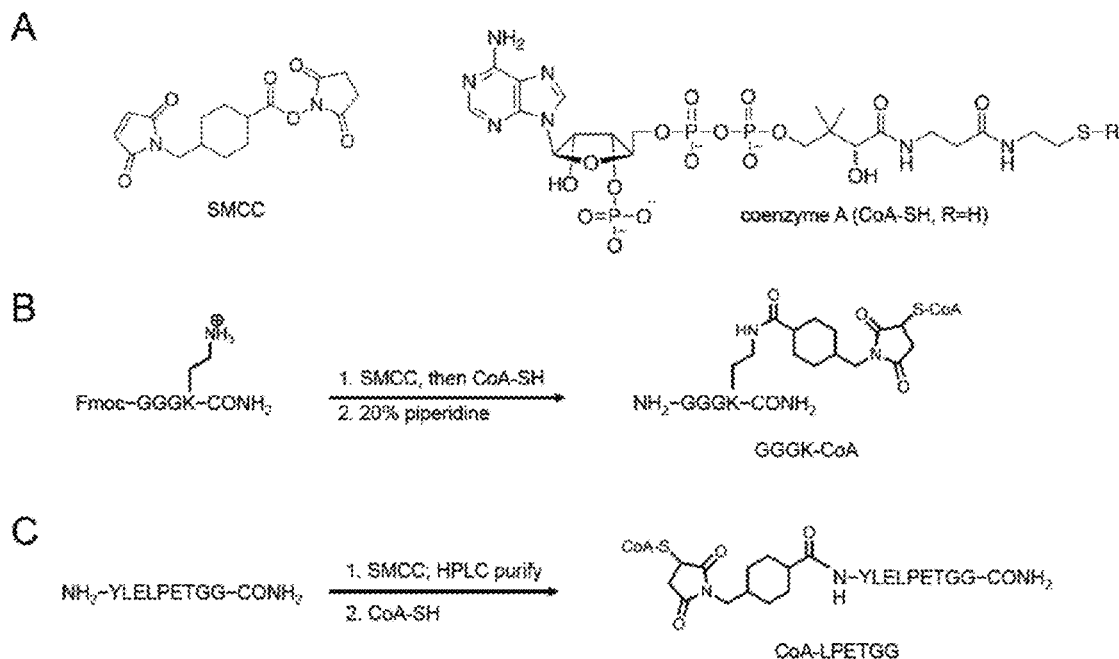
FIG. 8. Synthesis of coenzyme A-conjugated sortase substrates. (A) Chemical structures of the SMCC crosslinker and coenzyme A (CoA). (B) Synthesis strategy for GGGK-CoA (SEQ ID NO: 35). (C) Synthesis strategy for CoA-LPETGG (SEQ ID NO: 33). Also shown are the sequences of SEQ ID NOs: 35 and 50.

We first examined if yeast-displayed sortases in our system could catalyze the reaction between surface-immobilized LPETGG (SEQ ID NO: 33) and exogenous biotinylated triglycine peptide (GGGYK-biotin) (SEQ ID NO: 37). To conjugate cells to the LPETGG (SEQ ID NO: 33) substrate, we incubated yeast displaying wild type srtA and the S6 peptide with Sfp and CoA-linked LPETGG (CoA-LPETGG; FIG. 8) (SEQ ID NO: 33). The sortase-catalyzed reactions were initiated with the addition of GGGYK-biotin (SEQ ID NO: 37) and 5 mM CaCl$_2$. After washing, the cells were stained with streptavidin-PE and an AlexaFluor488-conjugated anti-HA antibody to analyze the extent of reaction and enzyme display level, respectively, by flow cytometry. When yeast cells displaying wild type sortase A (WT srtA-yeast) were analyzed, the majority of the cells exhibited high levels of PE fluorescence, indicating substantial conjugation with GGGYK-biotin (FIG. 2A) (SEQ ID NO: 37). In contrast, wild type srtA-yeast not conjugated to LPETGG (SEQ ID NO: 33), or LPETGG-conjugated (SEQ ID NO: 33) yeast cells displaying the inactive C184A sortase mutant, exhibited only background levels of PE fluorescence after incubation with GGGYK-biotin (SEQ ID NO: 37), confirming that biotinylation was dependent both on sortase activity and on the presence of both substrates (FIG. 2A).

Figure 9:
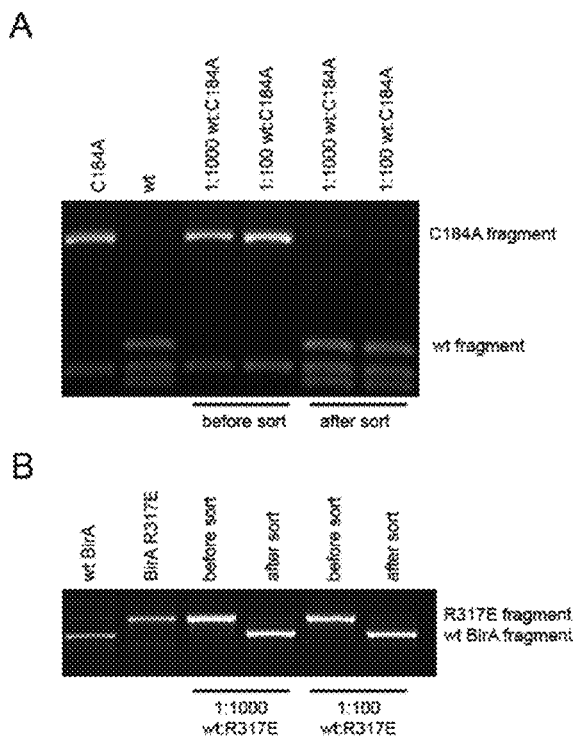
FIG. 9. Additional model screening results. (A) The indicated wt:C184A srtA-yeast mixtures were modified with GGGK-CoA (SEQ ID NO: 35), incubated with 50 µM biotin-LPETGG (SEQ ID NO: 33) for 15 minutes, and sorted as described in FIG. 2. Analysis of the gene compositions before and after sorting by HindIII digestions reveals an enrichment factor of ~3,500-15,500 after a single round of sorting. (B) Yeast simultaneously displaying the AviTag sequence and wild type *E. coli* biotin ligase (BirA) or its less active R317E mutant (Chapman-Smith A, Mulhern T D, Whelan F, Cronan J E, Jr., & Wallace J C (2001) The C-terminal domain of biotin protein ligase from *E. coli* is required for catalytic activity. Protein Science 10(12):2608-2617) were mixed in 1:1000 and 1:100 BirA:R317E ratios. The mixtures were incubated with unmodified streptavidin to silence the biotinylation signal that arises from BirA-catalyzed biotinylation of the AviTag within the yeast secretory pathway during induction. The cells were treated with 1 µM biotin, 5 mM $MgCl_2$, and 0.2 mM ATP at room temperature for one hour. Following streptavidin-PE staining, the cells were subjected to FACS and the cells that exhibit the top 0.07% and 0.55% PE fluorescence intensities for the 1:1000 and 1:100 screens, respectively, were collected. Analysis of gene compositions before and after sorting by HindIII digestions reveals an enrichment factor of ~3,500-15,500 after one single round of sorting.

To verify that enzymes displayed on the yeast cell surface catalyze pseudointramolecular reactions with substrate molecules immobilized on the same cell, we performed one round of model screening on mixtures of wild type srtA-yeast and srtA C184A-yeast. Yeast cells were mixed in 1:100 and 1:1; 000 ratios of wild type: C184A sortases. Each mixture of cells was coupled with CoA-LPETGG (SEQ ID NO: 33) using Sfp, then incubated with 50 µM GGGYK-biotin (SEQ ID NO: 37) for 15 min. Because srtA binds weakly to GGG ($K_m$=140 µM; Table 1), washing with nonbiotinylated GGG was sufficient to remove any background signal, and TEV digestion was not performed after the reaction. After fluorophore staining, cells exhibiting both AlexaFluor488 and PE fluorescence were isolated by FACS (FIG. 2B) and amplified by culturing to saturation. The plasmid DNA encoding survivors was harvested, and the compositions of the recovered genes were analyzed by restriction digestion with HindIII following PCR amplification. The wild type srtA gene is distinguishable from C184A by the presence of an additional HindIII site (FIG. 2C). In both model FACS sort experiments, we observed ≥6;000-fold enrichment of the wild type gene from both mixtures that were predominantly the inactive C184A mutant (FIG. 2C). Similarly high enrichment factors were also observed in model sortase screens in which GGG-modified cells were reacted with biotinylated LPETGG (SEQ ID NO: 33) peptide, and in model biotin ligase (BirA) screens in which cells displaying a biotinylation substrate peptide and wild type BirA were enriched in the presence of a large excess of cells displaying a less active BirA mutant (FIG. 9). These results show that this system can strongly enrich yeast displaying active bond-forming enzymes from mixtures containing predominantly yeast displaying inactive or less active enzyme variants.

Directed Evolution of Sortase a Enzymes with Improved Catalytic Activity.

Next, we sought to evolve S. aureus srtA for improved activity using the enzyme evolution strategy validated above. We focused on improving the poor LPXTG (SEQ ID NO: 51) substrate recognition of srtA ($K_m$=7.6 mM; Table 1), which limits the usefulness of sortase-catalyzed bioconjugation by requiring the use of high concentrations of enzyme (>30 µM) or long reaction times to compensate for poor reaction kinetics at the micromolar concentrations of LPXTG (SEQ ID NO: 51) substrate that are typically used. To direct evolutionary pressure to improve LPXTG (SEQ ID NO: 51) recognition, we formatted the screen such that the triglycine substrate is immobilized on the cell surface along with the enzyme library, and the biotinylated LPETG (SEQ ID NO: 32) peptide is added exogenously. This format enables evolutionary pressure for improved LPETG (SEQ ID NO: 32) recognition to be increased simply by lowering the concentration of LPETG (SEQ ID NO: 32) peptide provided during the sortase-catalyzed bond-forming reaction.

We randomly mutated the wild type S. aureus srtA gene using PCR with mutagenic dNTP analogs (24) and cloned the resulting genes into the modified yeast display vector using gap repair homologous recombination to yield a library of 7.8×10$^7$ transformants (round 0, R0). Each library member contained an average of two nonsilent mutations. The library was subjected to four rounds of enrichment for sortase activity without any additional diversification between rounds. In each round, we subjected control samples—cells displaying wild type srtA or an improved mutant, or the cells isolated from the previous round—to identical reaction conditions and screening protocols to precisely define FACS gates that captured cells with PE fluorescence corresponding to improved sortase activity (FIG. 10). We applied increasing evolutionary pressure for improved LPETG (SEQ ID NO: 32) recognition by decreasing the concentration of biotinylated LPETG (SEQ ID NO: 32) substrate 10-fold with each successive round, starting from 100 µM in the first round and ending with 100 nM in the fourth round (FIG. 11). We also increased evolutionary pressure for overall catalytic activity by accepting a smaller percentage of the most PE-fluorescent cells with each successive round, ranging from 1.4% in R1 to 0.15% in R4, and by shortening the reaction time in R4 from 60 to 15 min.

To preclude the evolution of specificity for a particular LPETG-containing (SEQ ID NO: 32) sequence, we alternated using biotin-LPETGS (SEQ ID NO: 36) (R1 and R3) and biotin-LPETGG (SEQ ID NO: 33) (R2 and R4) peptides. After the fourth round of enrichment, surviving genes were subjected to in vitro homologous recombination using the NExT procedure (25) and recloned into yeast to yield a recombined and diversified library of 6.9×10$^7$ transformants. The shuffled library (R4Shuf) was subjected to four additional rounds of sorting (resulting in R5, R6, R7, and R8), with the concentration of biotinylated LPETG (SEQ ID NO: 32) peptide dropping from 100 to 10 nM in R8 (FIG. 11).

Figure 12:
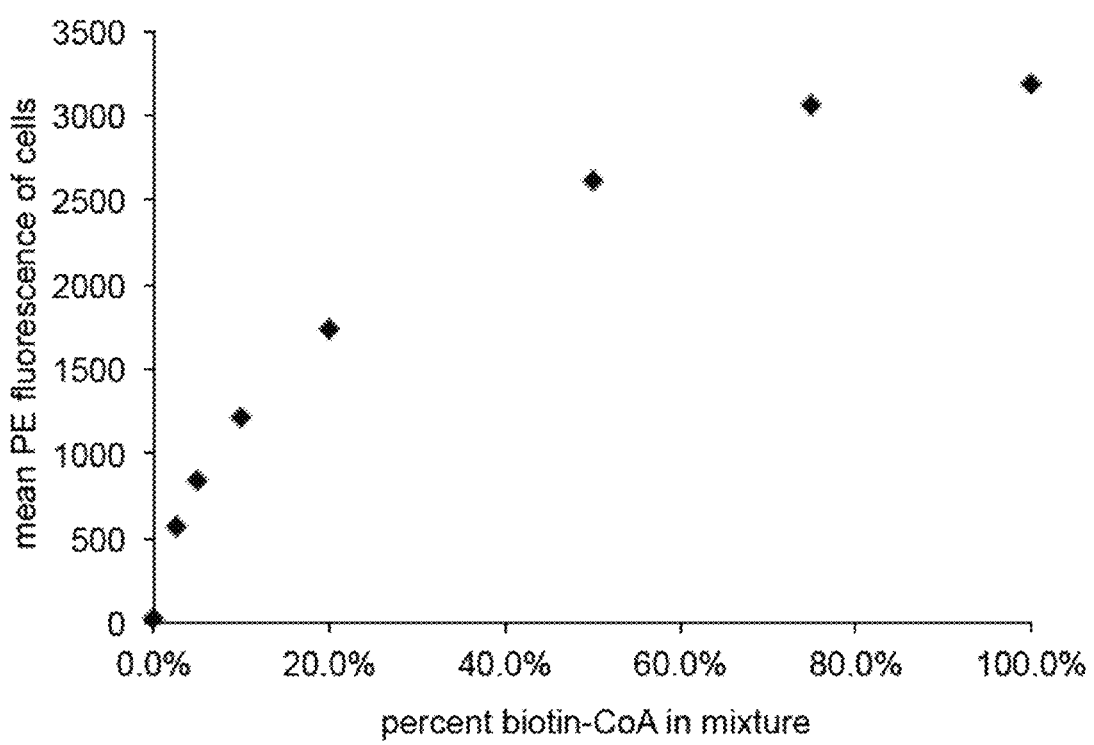
FIG. 12. The relative amount of biotinylated CoA adduct in the supernatant is reflected by cell surface fluorescence after Sfp-catalyzed conjugation to yeast cells and streptavidin-PE staining. Biotin-CoA was mixed with GGGK-CoA (SEQ ID NO: 35) in various molar ratios. A suspension of ICY200 cells at a density of $2.5 \times 10^7$ cells/mL was incubated with 6 µM Sfp and 5 µM total concentration of CoA conjugate. The fluorescence of the cells after streptavidin staining was measured using flow cytometry.

We developed an assay to rapidly compare the activity of yeast displayed sortase mutants. Yeast cells were incubated with TEV protease to release the enzymes from the cell surface into the surrounding supernatant. The reaction in the supernatant was initiated by the addition of the two peptide substrates, CoA-LPETGG (SEQ ID NO: 33) and GGGYK-biotin (SEQ ID NO: 37). After 30 min of reaction, Sfp was added to the same reaction mixture to attach the biotinylated adduct and unreacted CoA-LPETGG (SEQ ID NO: 33) onto the cell surface. We verified that the level of cell-surface fluorescence after streptavidin-PE staining is a direct reflection of the relative amount of biotinylated product in solution (FIG. 12).

Figure 3:
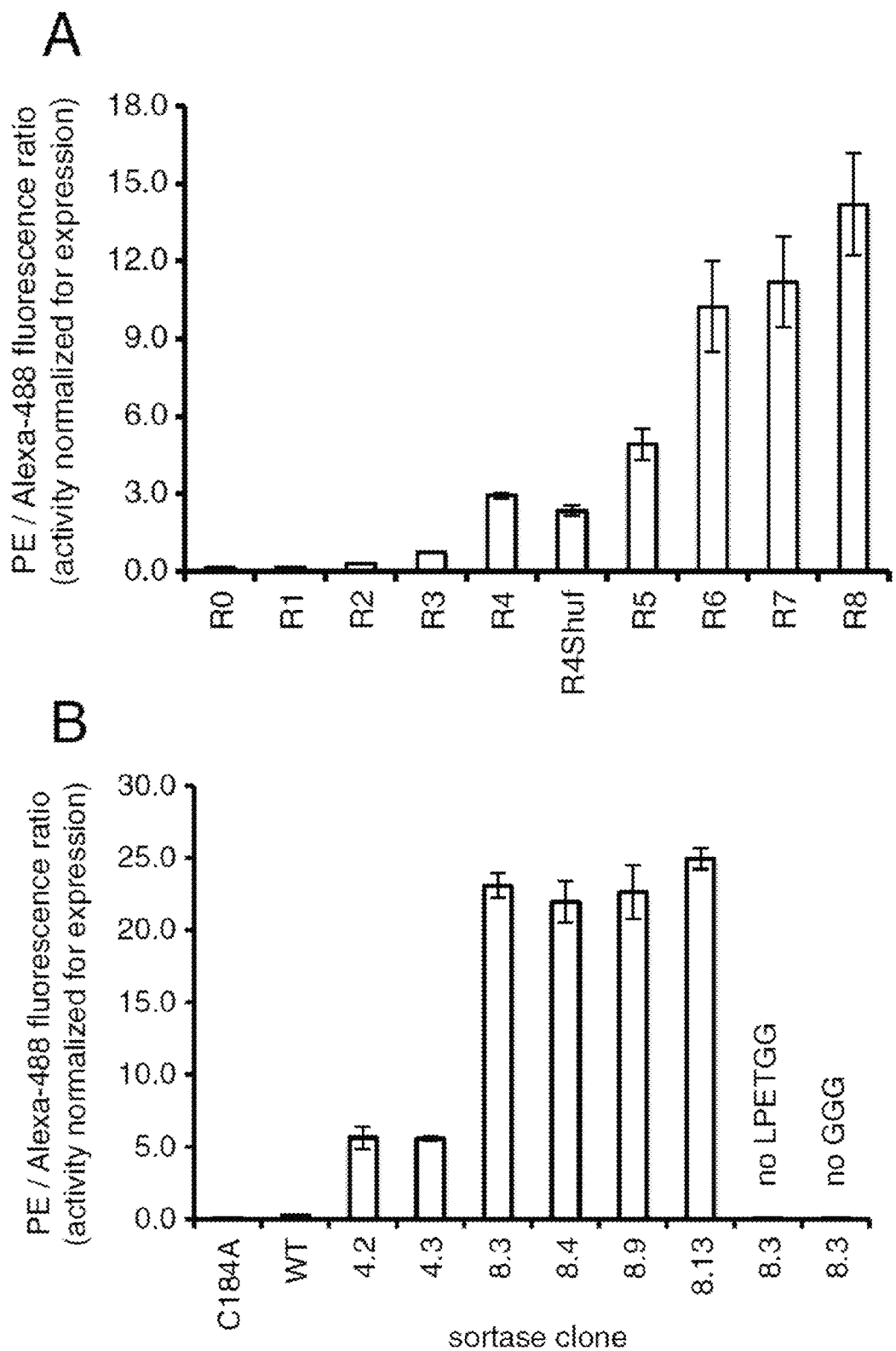
FIG. 3. Activity assays of mutant sortases. (A) Yeast pools recovered from the sorts were treated with TEV protease, and the cleaved enzymes were assayed for their ability to catalyze coupling between 5 µM CoA-LPETGG (SEQ ID NO: 33) and 25 µM GGGYK-biotin (SEQ ID NO: 37). (B) Yeast cells expressing select individual clones were treated as described in the Examples section. Error bars represent the standard deviation of three independent experiments.

We evaluated the mean activity of the yeast pools recovered after each round of sorting using this assay. Over the course of the selections, we observed a steady increase in the extent of product formation catalyzed by the recovered sortase mutants. By the last round (R8) the activity signal was approximately 130-fold greater than that of the initial, unselected library (R0), and approximately 40-fold greater than that of wild type srtA (FIGS. 3 A and B). These observations suggested that the system had evolved sortase variants with substantially improved activities.

TABLE 1

Kinetic characterization of mutant sortases

| | $k_{cat}$, s$^{-1}$ | $K_{m\ LPETG}$, mM | $k_{cat}/K_{m\ LPETG}$, M$^{-1}$ s$^{-1}$ | $K_m$ GGG-COOH, µM |
|---|---|---|---|---|
| WT | 1.5 ± 0.2 | 7.6 ± 0.5 | 200 ± 30 | 140 ± 30 |
| D160N/K190E/K196T (clone 4.2) | 3.7 ± 0.6 | 1.6 ± 0.4 | 2,400 ± 700 | 1,200 ± 200 |
| P94S/D165A (clone 4.3) | 2.9 ± 0.0 | 1.1 ± 0.1 | 2,600 ± 100 | 1,700 ± 400 |
| P94S/D160N/D165A/K196T | 4.8 ± 0.8 | 0.17 ± 0.03 | 28,000 ± 7,000 | 4,800 ± 700 |
| P94S/D160N/K196T | 4.8 ± 0.6 | 0.56 ± 0.07 | 8,600 ± 1,500 | 1,830 ± 330 |
| P94S/D160N/D165A | 3.8 ± 0.2 | 0.51 ± 0.38 | 7,500 ± 300 | 1,750 ± 250 |
| P94R/D160N/D165A/K190E/K196T | 5.4 ± 0.4 | 0.23 ± 0.02 | 23,000 ± 3,000 | 2,900 ± 200 |
| P94S | 1.6 ± 0.1 | 2.5 ± 0.6 | 600 ± 200 | 650 ± 150 |
| D160N | 2.3 ± 0.2 | 3.7 ± 0.5 | 600 ± 100 | 330 ± 20 |
| D165A | 2.4 ± 0.3 | 3.6 ± 1.0 | 700 ± 200 | 1,000 ± 480 |
| K196T | 1.2 ± 0.1 | 3.3 ± 0.8 | 400 ± 100 | 200 ± 70 |

Kinetic parameters $k_{cat}$ and $K_m$ were obtained from fitting initial reaction rates at 22.5° C. to the Michaelis-Menten equation. Errors represent the standard deviation of three independent experiments.

Characterization of Evolved Sortase Mutants.

We used the above assay to evaluate the activity of individual clones from R4 and R8 together with wild type srtA and the inactive C184A mutant (FIG. 3B). All tested mutants from R4 exhibited improved activity relative to wild type, with the two most active mutants, 4.2 and 4.3, showing approximately 20-fold more activity than wild type srtA. Mutants isolated from R8 exhibited even greater gains in activity, including four mutants that were ≥100-fold more active than wild type srtA under the assay conditions (FIG. 3B).

Figure 4:
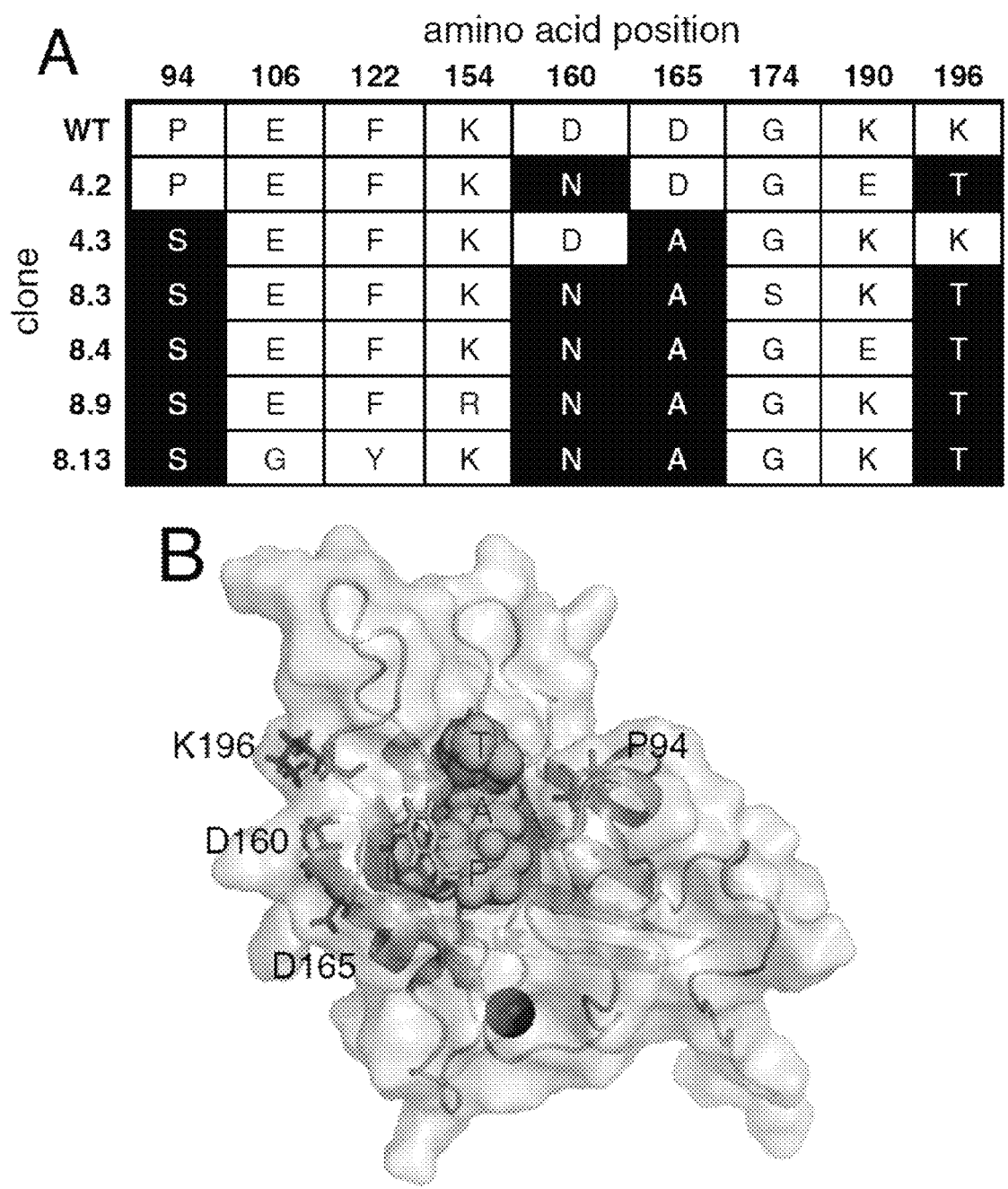
FIG. 4. Mutations in evolved sortases. (A) Highly enriched mutations are highlighted in black; other mutations are shown in blue. (B) Mapping evolved mutations on the solution structure of wild type *S. aureus* sortase A covalently bound to its Cbz-LPAT (SEQ ID NO: 39) substrate. The calcium ion is shown in blue, the LPAT (SEQ ID NO: 39) peptide is colored cyan with red labels, and the side chains of amino acids that are mutated are in orange. The N-terminal Cbz group is shown in stick form in cyan.
Figure 5:
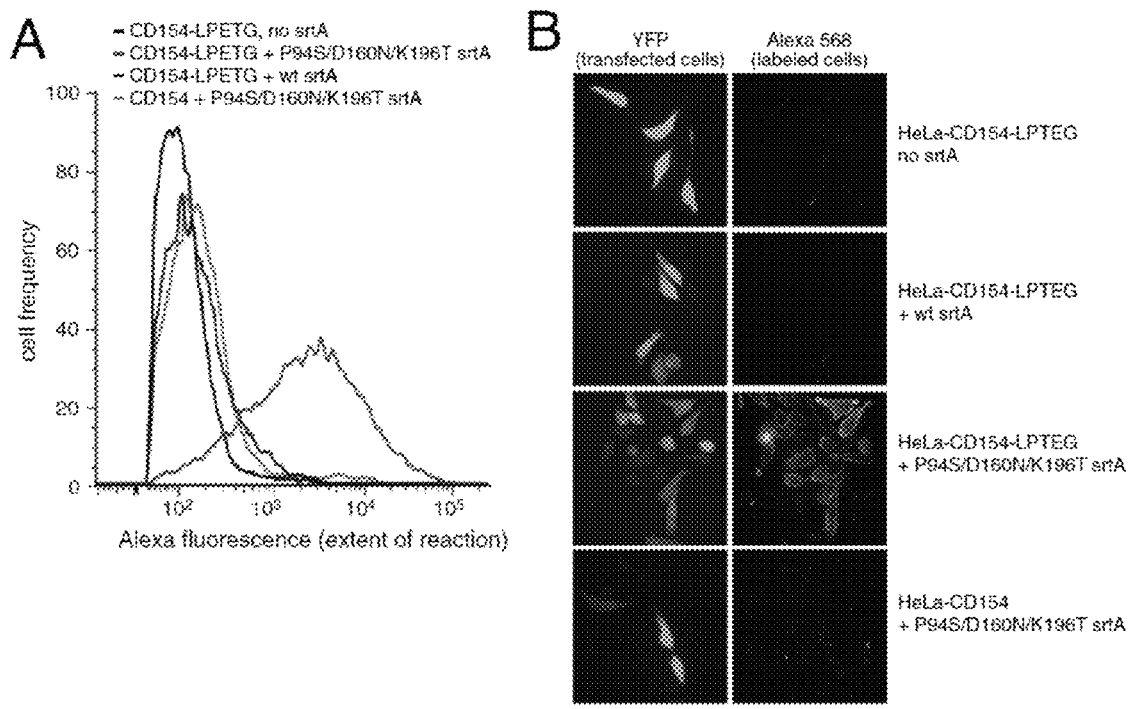
FIG. 5. Cell-surface labeling with wild type and mutant sortases. Live HeLa cells expressing human CD154 conjugated at its extracellular C terminus to LPETG (SEQ ID NO: 32) were incubated with 1 mM GGGYK-biotin (SEQ ID NO: 37) and no sortase A (srtA), 100 µM wild type srtA, or 100 µM P94S/D160N/K196T srtA. The cells were stained with Alexa-Fluor-conjugated streptavidin. (A) Flow cytometry analysis comparing cell labeling with wild type sortase (blue) and the mutant sortase (red). Negative control reactions omitting sortase (black) or LPETG (SEQ ID NO:32) (green) are shown. (B) Live cell confocal fluorescence microscopy images of cells. The yellow fluorescent protein (YFP, transfection marker) and Alexa (cell labeling) channels are shown.

Sequences of evolved sortase genes revealed the predominance of P94S or P94R, D160N, D165A, and K196T mutations among R8 clones (FIG. 4A and FIG. 13B). Of the 16 unique sequences we isolated from R8, nine contained all four mutations. Thirteen of the 16 unique sequences contained at least three of the mutations, and all sequences contained at least two of the four mutations. All of these mutations also appeared in clones isolated from R4, but no clone from R4 contained more than two of the mutations, suggesting that recombination following R4 enabled combinations of mutations that persisted in rounds 4-8. Indeed, the highly enriched tetramutant combination appears to have arisen from recombination of two mutations each from clones 4.2 and 4.3, the two most active mutants isolated from R4. Gene shuffling was therefore an important component of the evolutionary strategy to generate genes encoding the most active sortases tested.

Figure 14:
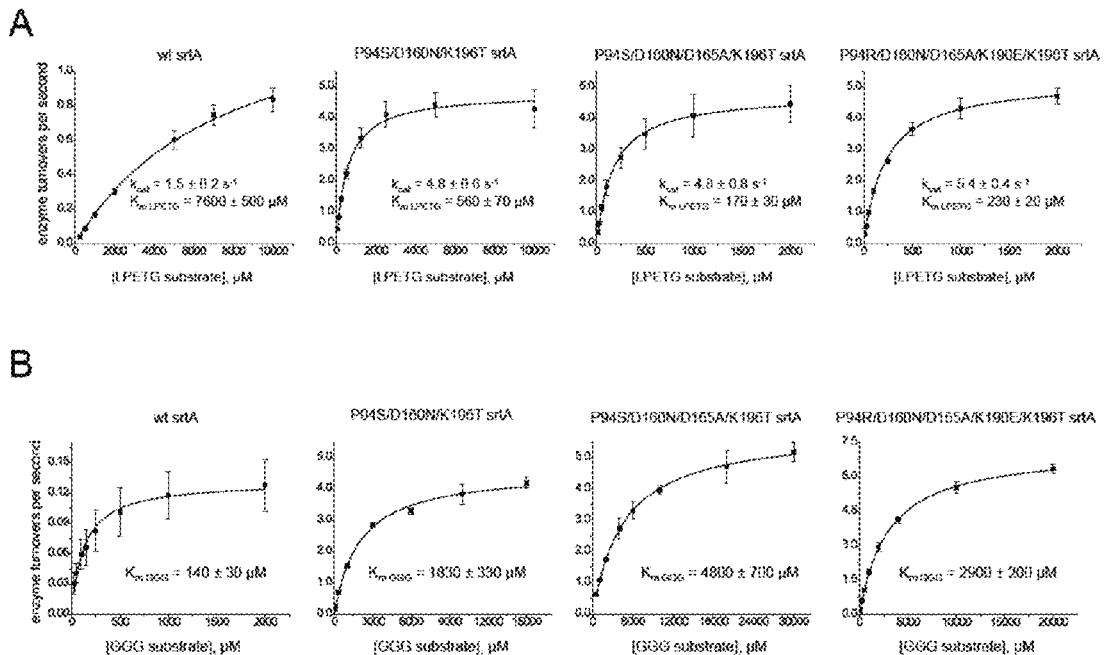
FIG. 14. Representative kinetic measurements of the sortase-catalyzed reaction between Abz-LPETGK(Dnp)-$CONH_2$ (SEQ ID NO: 48) and GGG-COOH to yield Abz-LPETGGG (SEQ ID NO: 34). (A) Michaelis-Menten curves to determine $k_{cat}$ and $K_{m\ LPETG}$ (SEQ ID NO: 32). (B) Michaelis-Menten curves to determine $K_{m\ GGG}$. For both (A) and (B), the overall reaction velocity is represented as turnovers per second (product concentration/enzyme concentration). In every experiment, the enzyme concentration was <1% of the substrate concentration and >1% of the substrate was converted to product, ensuring that multiple turnover kinetics were measured.
Figure 15:
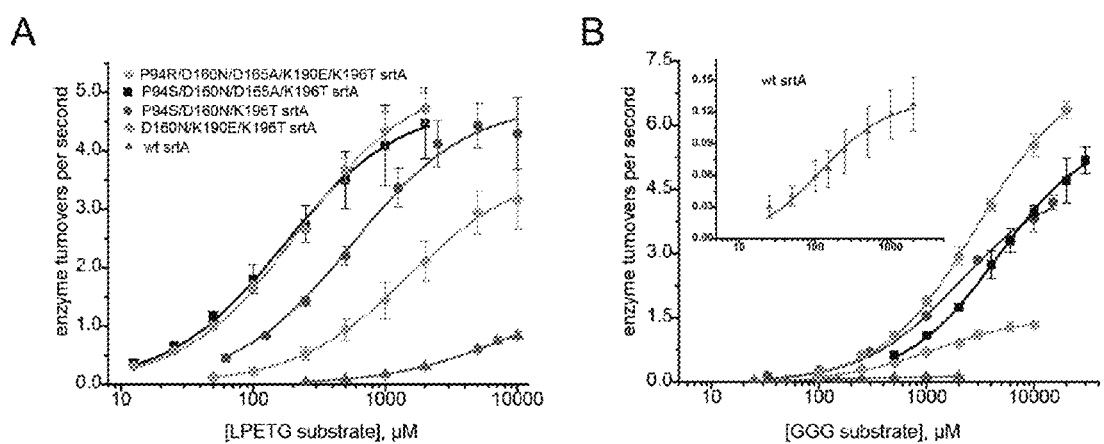
FIG. 15. Comparison of the kinetic parameters of four evolved sortases. (A) Plots of reaction velocity (turnovers per second) vs. LPETG (SEQ ID NO: 32) peptide substrate concentration, with [GGG] fixed at 9 mM. (B) Plots of reaction velocity vs. GGG concentration, with [LPETG peptide] (SEQ ID NO: 32) fixed at 1 mM. Due to its poor kinetics under the assay conditions, the plot for wt srtA is shown in the inset.

None of these four mutations have been reported in previous mutational studies studying the sortase active site and the molecular basis of LPETG (SEQ ID NO: 32) substrate recognition (26, 27). To gain insight into how these mutations improve catalysis, we expressed and purified each sortase single mutant, clones 4.2 and 4.3, and the tetramutant from Escherichia coli, and we measured the saturation kinetics of wild type srtA and the mutants using an established HPLC assay (28). The observed kinetic parameters for the wild type enzyme closely match those previously reported (26, 28). Each single mutation in isolation contributed a small beneficial effect on turnover ($k_{cat}$) and more significant beneficial effects on LPETG (SEQ ID NO: 32) substrate recognition, lowering the $K_{m\ LPETG}$ up to threefold (Table 1). The effects of the mutations in combination were largely additive. Compared to wild type, 4.2 and 4.3 exhibited a 2.0-2.6-fold improvement in $k_{cat}$ and a 5-7-fold reduction in $K_{m\ LPETG}$, resulting in an approximately 15-fold enhancement in catalytic efficiency at using the LPETG (SEQ ID NO: 32) substrate (Table 1). Combining all four mutations yielded a sortase with a 140-fold improvement in its ability to convert LPETG (SEQ ID NO: 32) ($k_{cat}/K_{m\ LPETG}$). This large gain in catalytic efficiency is achieved primarily through 45-fold improved LPETG (SEQ ID NO: 32) recognition accompanied by a 3-fold gain in $k_{cat}$ (Table 1; FIGS. 14 and 15).

The effects of the individual mutations on LPETG (SEQ ID NO: 32) substrate recognition can be rationalized in light of the reported solution structure of wild type S. aureus srtA covalently bound to an LPAT (SEQ ID NO: 39) peptide substrate (29). The mutated residues are all located at the surface of the enzyme, near the LPAT-binding groove (SEQ ID NO: 39) (FIG. 4B). P94 lies at the N terminus of helix 1, and K196 lies at the C terminus of the β7/β8 loop. Both D160 and D165 lie in the region connecting β6 and β7 that participates in LPETG (SEQ ID NO: 32) substrate binding. D165 lies at the N terminus of a 310 helix that is formed only upon LPAT (SEQ ID NO: 39) binding and makes contacts with the leucine residue of LPAT (SEQ ID NO: 39). The localization of the mutations within loops that line the LPAT (SEQ ID NO: 39) binding groove suggests that they may be improving binding by altering the conformation of these important loops.

The evolved sortase mutants exhibit decreased GGG substrate binding (Table 1; FIGS. 14 and 15). Compared to wild type, we measured a 30-fold increase in $K_{m\ GGG}$ for the sortase A tetramutant. P94S, and D165A had larger detrimental effects on $K_{m\ GGG}$ than D160N and K196T. These results are consistent with mapping of the GGG-binding region proposed by NMR amide backbone chemical shift data. The chemical shifts of the visible amide hydrogen resonances for residues 92-97 and 165 were among the most perturbed upon binding of a Gly3 peptide (29). Because of the absence of a high-resolution structure of the srtA-Gly3 complex at this time, it is difficult to rationalize in more detail the basis of altered $K_{m\ GGG}$ among evolved mutants.

To recover some of the ability to bind the GGG substrate, we reverted A165 of the tetramutant back to the original aspartic acid residue found in wild type because our results indicated that the D165A mutation was most detrimental for GGG recognition. Compared to the tetramutant, this P94S/D160N/K196T triple mutant exhibited a 2.6-fold improvement in $K_m$ GGG, accompanied by a threefold increase in $K_{M\,LPETG}$ and no change in $k_{cat}$ (Table 1; FIGS. 14 and 15). We also subjected the R8 yeast pool to one additional round of screening (R9), immobilizing LPETGG (SEQ ID NO: 33) on the cell surface before reaction with 100 nM GGGYK-biotin (SEQ ID NO: 37). The P94S/D160N/K196T reversion mutant was recovered in two out of the 24 sequenced clones from R9, but a different triple mutant (P94S/D160N/D165A) dominated the R9 population after screening, representing 14/24 sequenced clones (FIG. 13C). Compared to the tetramutant, the $K_{m\,GGG}$ of this mutant improved by 2.7-fold, whereas the $k_{cat}$ and $K_{M\,LPETG}$ were not altered by more than a factor of 3-fold (Table 1).

Figure 16:
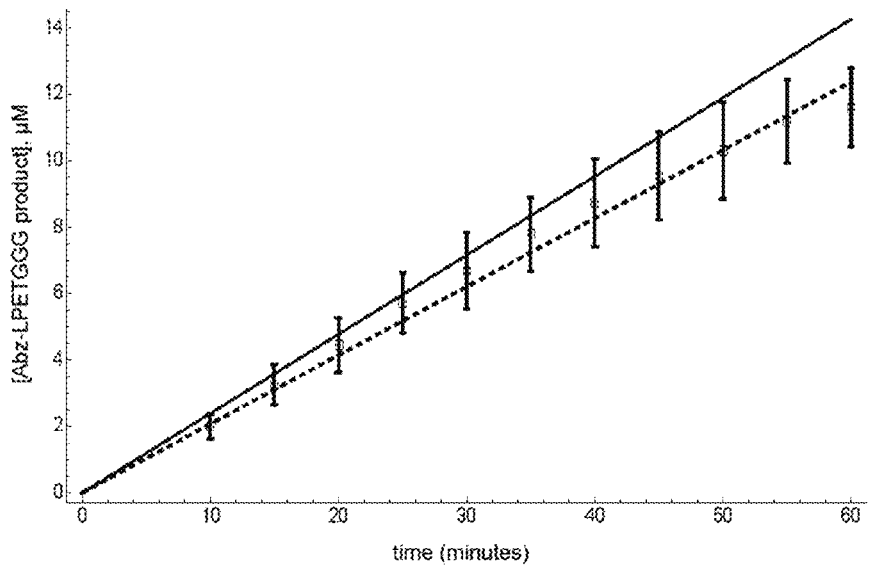
FIG. 16. Time course of turnovers by the evolved P94R/D160N/D165A/K190E/K196T sortase. P94R/D160N/D165A/K190E/K196T srtA (914 pM) was incubated with 9 mM GGG and 1 mM Abz-LPETGK(Dnp) (SEQ ID NO: 48) substrate in 500 µL of reaction buffer. At 5-minute intervals, 40-µL aliquots were removed, quenched, and analyzed by HPLC as described in the Examples section. Each µM of product generated over the course of this experiment corresponds to approximately 1,092 turnover events. Averaged data and standard deviation from triplicate experiments are shown as open squares and bars, respectively. Fit lines were generated by Mathematica according to the integrated Michaelis Menten equation, [Product]=[Substrate]$_0$-$K_m$ ProductLog[Exp[([Substrate]$_0$-$k_{cat}$*time*[Enzyme])/$K_m$]*[Substrate]$_0$/$K_m$], where [Substrate]$_0$=1 mM and [Enzyme]= 914 pM. The expected product concentration from previously determined kinetic parameters is shown (black line) while a fit line to the data is shown (dashed). These data show an r2 correlation of 0.983 with kinetic parameters $k_{cat}$=4.7±0.6 s-1 and $K_{m\ LPETG}$=245±5 µM, compared with the parameters of $k_{cat}$=5.4±0.4 s-1 and $K_{m\ LPETG}$=230±20 µM determined by endpoint analysis (Table 1, FIGS. 16, 17). The difference in observed $k_{cat}$ is not statistically significant by Students' t test to p>0.95.

We also performed mutagenesis and enrichment to identify additional mutations that improve GGG recognition in the tetramutant context. We combined four R8 clones as templates for additional diversification by PCR, and subjected the resulting yeast library (R8mut) to two rounds of screening, immobilizing LPETGG (SEQ ID NO: 33) on the cell surface before reaction with 100-1,000 nM GGGYK-biotin (SEQ ID NO: 37). After two rounds of enrichment, the K190E mutation originally observed in clone 4.2 was found in 56% of the unique sequenced clones in R10mut, and 33% of the clones possessed P94R in place of P94S (FIG. 13D). The other three mutations of the tetramutant motif were found intact in 89% of the unique R10mut clones. We constructed the P94R/D160N/D165A/K190E/K196T pentamutant and assayed its activity. Compared to the tetramutant, the $K_{m\,GGG}$ of this mutant improved by 1.8-fold, whereas the $k_{cat}$ and $K_{M\,LPETG}$ were not altered by more than a factor of 1.3-fold. Compared with wild type srtA, this pentamutant has a 120-fold higher $k_{cat}/K_{M\,LPETG}$ and a 20-fold higher $K_{m\,GGG}$ (Table 1; FIGS. 14 and 15). To validate our enzyme kinetics measurements, we followed product formation over 1 h and observed turnover numbers of greater than 10,000 per hour. The resulting data (FIG. 16) yielded $k_{cat}$ and $K_{M\,LPETG}$ values that closely agree with our kinetics measurements (Table 1). These results indicate that relatives of the evolved tetramutant can exhibit partially restored GGG binding and therefore provide alternative enzymes for applications in which the GGG-linked substrate is available only in limited quantities.

Cell-Surface Labeling with an Evolved Sortase.

The improved activities of the evolved sortases may enhance their utility in bioconjugation applications such as the site-specific labeling of LPETG-tagged (SEQ ID NO: 21) proteins expressed on the surface of living cells. In these applications, the effective concentration of the LPETG (SEQ ID NO: 21) peptide is typically limited to micromolar or lower levels by endogenous expression levels, and therefore the high $K_{M\,LPETG}$ of wild type srtA ($K_{M\,LPETG}$=7.6 mM; Table 1) necessitates the use of a large excess of coupling partner and enzyme to drive the reaction to a reasonable yield. Because it is typically straightforward to synthesize milligram quantities of short oligoglycine-linked probes using solid-phase peptide chemistry, we hypothesized that the much higher $k_{cat}/K_{M\,LPETG}$ of the evolved sortases might enable them to mediate cell-surfacing reactions that would be inefficient using the wild type enzyme.

Figure 17:
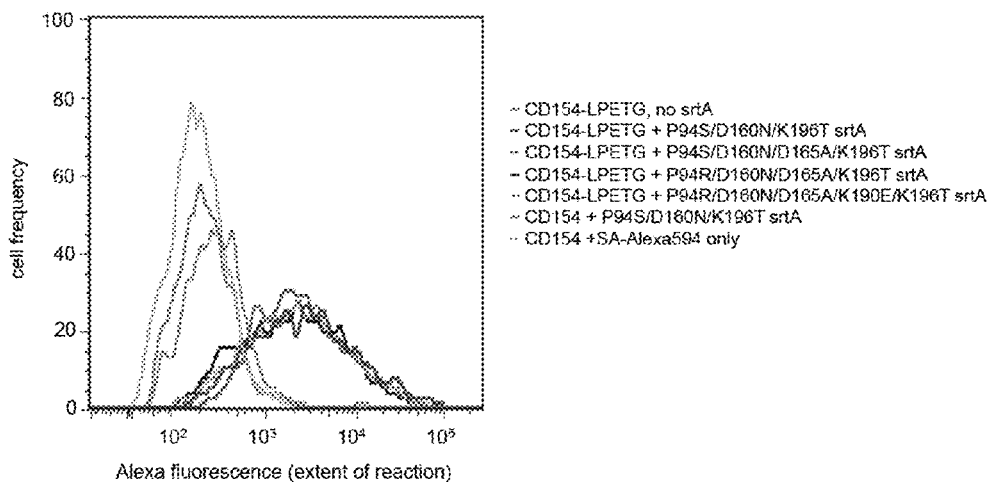
FIG. 17. Cell-surface labeling with four evolved sortases. Live HeLa cells expressing human CD154 conjugated at its extracellular C-terminus to LPETG (SEQ ID NO: 32) were incubated with 0.5 mM GGGYK-biotin (SEQ ID NO: 37) and no sortase A (no srtA) or 100 µM of the mutant sortase A shown in the legend. The cells were stained with AlexaFluor594-conjugated streptavidin (SA-Alexa594) before flow cytometry analysis. Negative control reactions omitting sortase (green) or LPETG (SEQ ID NO: 32) (gray) are shown. Untreated cells stained with SA-594 (cyan) are also shown.

We expressed human CD 154 tagged with the LPETG (SEQ ID NO: 32) sequence at its C terminus on the surface of HeLa cells and compared the labeling of the live cells with GGGYK-biotin (SEQ ID NO: 37) using wild type srtA and the evolved P94S/D160N/K196T mutant. After staining with a streptavidin-AlexaFluor594 conjugate, flow cytometry analysis revealed that the evolved sortase yielded ≥30-fold higher median fluorescence than the wild type enzyme (FIG. 5A). Although we used conditions similar to those used to label HEK293 cells using wild type srtA for fluorescence microscopy (4), over four independent replicates, the wild type enzyme did not result in fluorescence more than 2.8-fold higher than the background fluorescence of cells incubated in the absence of enzyme (FIG. 5A). Consistent with the flow cytometry data, live-cell fluorescence microscopy confirmed very weak labeling by wild type srtA and much more efficient labeling by the evolved sortase mutant (FIG. 5B). Cells expressing CD154 without the LPETG (SEQ ID NO: 32) tag were not labeled to a significant extent by the evolved sortase, indicating that the site-specificity of the enzyme has not been significantly compromised. Under the conditions tested, the evolved sortase triple, tetra-, and pentamutants all exhibit comparable and efficient cell-surface labeling, despite their differences in $K_{m\,GGG}$ (FIG. 17). Collectively, our results suggest that the sortase variants evolved using the enzyme evolution system developed in this work are substantially more effective than the wild type enzyme at labeling LPETG-tagged (SEQ ID NO: 32) proteins on the surface of live mammalian cells.

Directed Evolution of Sortase a Enzymes with Altered Substrate Specificity.

In an effort to develop S. Aureus Sortase A derivatives of altered substrate specificity, we took advantage of the single turnover nature of the selection described herein. By co-incubating yeast displaying a Sortase A variant with both biotinylated LPESG (SEQ ID NO: 38) and a large excess of unbiotinylated LPETG (SEQ ID NO: 32), we successfully enriched for enzymes with reduced affinity for LPETG (SEQ ID NO: 32), and increased affinity for LPESG (SEQ ID NO: 38). Beginning from a naïve library of >10$^7$ variants of the pentamutant identified previously, we performed serial selections for the ability to react with LPESG (SEQ ID NO: 38) in the presence of competitive LPETG (SEQ ID NO: 32) (FIGS. 19-22). After four rounds of FACS sorting, we sequenced the remaining clones, observing complete convergence to a single variant, identified as Sortase 4S.4 and consisting of the 15 mutations P86L, P94R, N98S, A104T, A118T, F122S, D124G, N127S, K134R, D160N, D165A K173E, K177E, K190E, and K196T relative to wild type S. Aureus Sortase A. Further selections attempted to revert as many of these mutations as possible, leading ultimately to the optimized variant 4S.12.2, consisting of mutations P94R, N98S, A104T, A118T, F122S, D124G, K134R, D160N, D165A, K173E, K177E, K190E, and K196T. On characterization, both variants showed completely abrogated activity against LPETG (SEQ ID NO: 32), and activity against LPESG (SEQ ID NO: 38) comparable to the starting type pentamutant.

Discussion

Yeast display, Sfp-catalyzed bioconjugation, and cell sorting were integrated into a general directed evolution strategy for enzymes that catalyze bond-forming reactions. The system was validated through model selections enriching for S. aureus sortase A-catalyzed transpeptidation activity, attaining enrichment factors greater than 6,000 after a single round of sorting. The system was applied to evolve sortase A for improved catalytic activity. After eight rounds of sorting with one intermediate gene shuffling step, sortase A variants were isolated that contained four mutations that together resulted in a 140-fold increase in LPETG-coupling (SEQ ID NO: 32) activity compared with the wild type enzyme. An evolved sortase enabled much more efficient labeling of LPETG-tagged (SEQ ID NO: 32) human CD154 expressed on the surface of HeLa cells compared with wild type sortase.

Figure 18:
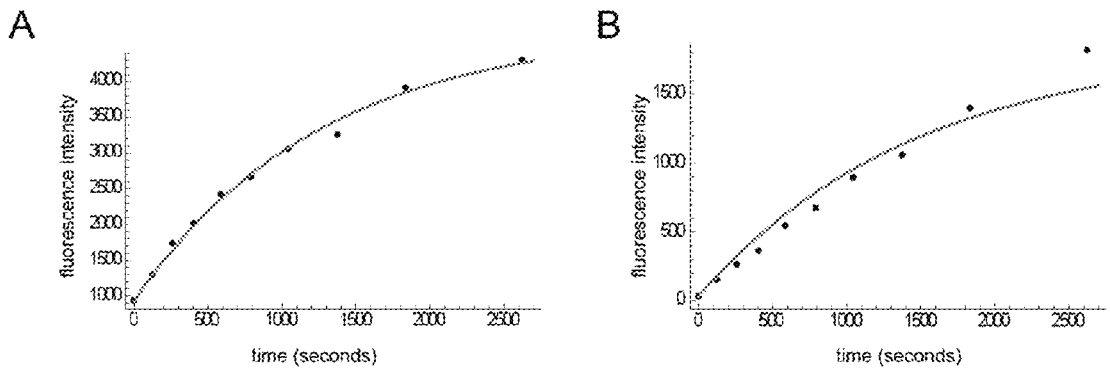
FIG. 18. Cell-surface reaction time courses to estimate substrate effective molarity. Yeast displaying clones 4.2 and 4.3 were first labeled with GGGK-CoA (SEQ ID NO: 35) and then reacted with 1 µM biotin-LPETGG (SEQ ID NO: 33) as described in the Examples section. Representative reaction progress curves for clone 4.2 (A) and 4.3 (B). The data was fit according to the equation described in the Examples section. In this case, the 4.2 data show an r2 correlation of 0.999 with a cell surface GGG effective molarity estimate of 1.007 mM and a theta estimate of 156 s, while the 4.3 data show an r2 correlation of 0.982 with a GGG effective molarity estimate of 0.967 mM and a theta estimate of 0 s.
Figure 19:
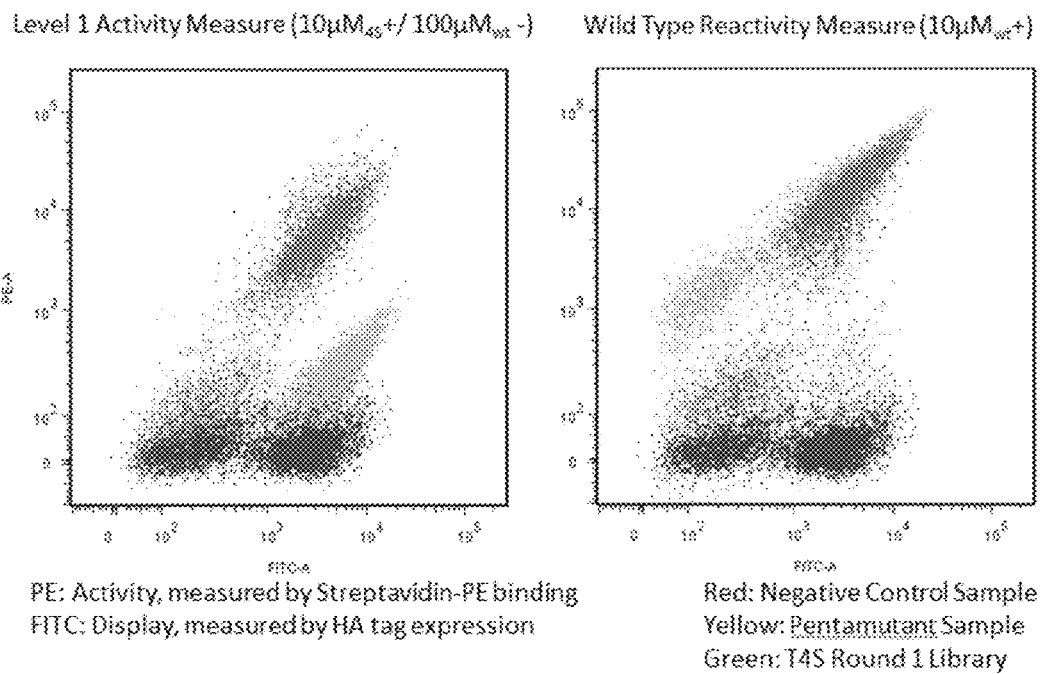
FIGS. 19-22. Reactivity profiles of a naïve library of SrtA mutants. Beginning from a library generated via random mutagenesis (as described herein), the pentamutant Sortase A (P94R/D160N/D165A/K190E/K196T) was subjected to four rounds of flow sorting under conditions of increasing stringency. In each round, biotinylated LPESG (SEQ ID NO: 38) was reacted in the presence of at least a 10-fold excess of unbiotinylated LPETG (SEQ ID NO: 32) and subjected to the selection described herein (left panel, each figure). Surviving library members were regrown and reinduced, then challenged with 10 μM Biotinyl-LPETG (SEQ ID NO: 32) and their reactivity measured (right panel, each figure). Over the course of four rounds of selection, virtually all LPETG (SEQ ID NO: 32) reactivity was abolished, while competitive LPESG (SEQ ID NO: 38) reactivity rose to significant levels.
Figure 20:
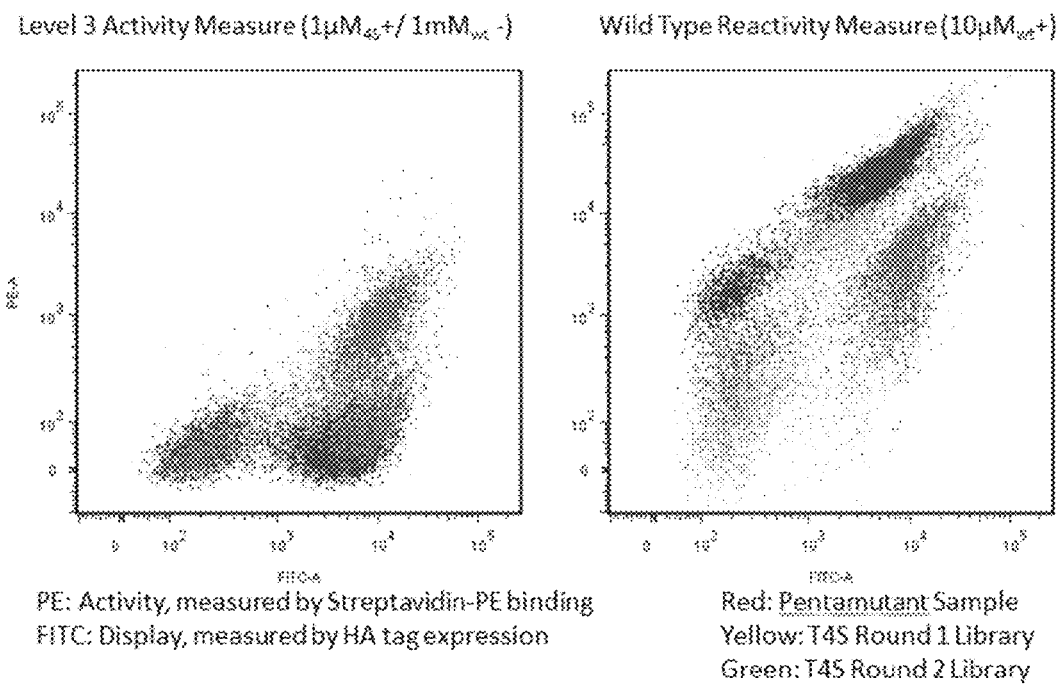
Figure 21:
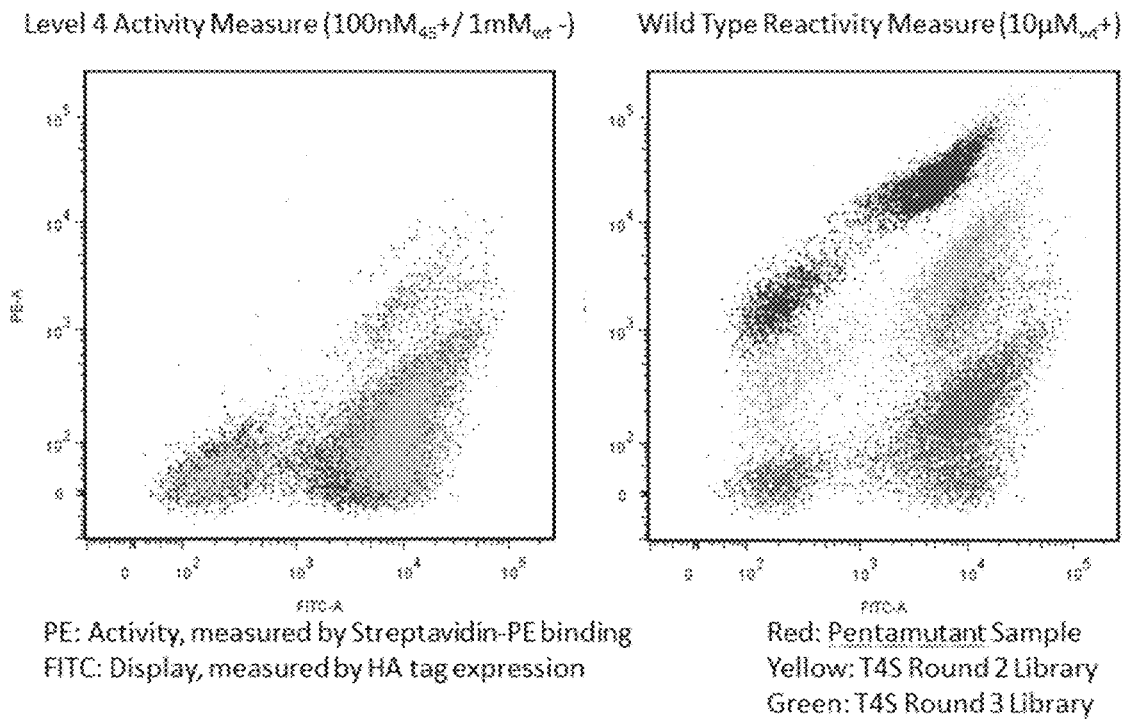
Figure 22:
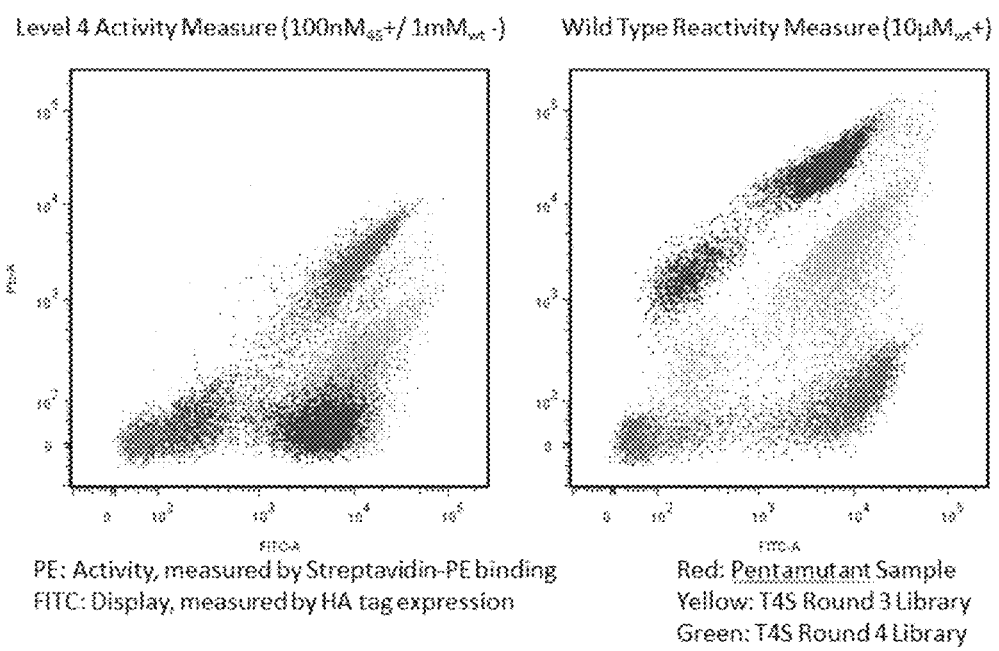
Figure 23:
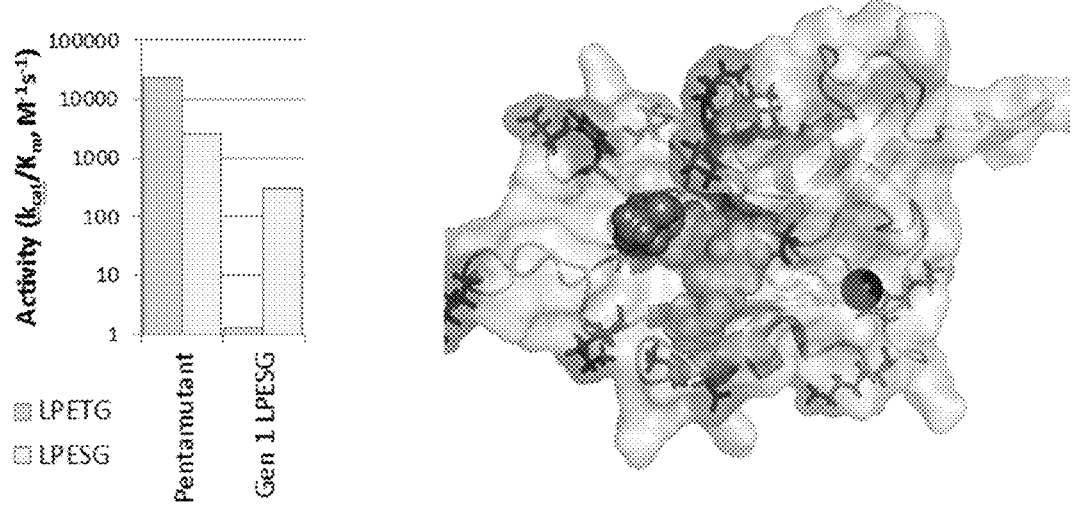
FIG. 23. The single clone identified from round 4 of the selection described in FIGS. 19-22 was subcloned and tested for activity on either LPETG (SEQ ID NO: 32) or LPESG (SEQ ID NO: 38) through an HPLC-based substrate cleavage assay. Measuring the $K_{cat}$ and $K_m$ of the enzyme for each of these substrates, the novel Sortase 4S.4 was found to have remarkably altered substrate specificity (>4000-fold, as determined by $K_{cat}/K_m$).

The kinetic properties of the mutant sortases accurately reflected the screening strategy. The 50-fold decrease in $K_{M\,LPETG}$ of the tetramutant compared to wild type is consistent with lowering the concentration of free biotinylated LPETG (SEQ ID NO: 32) peptide during the reaction in successive rounds. Meanwhile, this screening format ensured that a high effective molarity of GGG was presented to each enzyme candidate over eight rounds of enrichment, which was estimated to be approximately 950 μM (FIG. 18). GGG recognition among evolved sortases drifted during evolution. The threefold increase in $k_{cat}$ of the tetramutant compared to that of the wild type enzyme may have resulted from screening pressures arising from shortening the reaction time in later rounds. Larger increases in $k_{cat}$ may require modified selection or screening strategies that explicitly couple survival with multiple turnover kinetics, perhaps by integrating our system with in vitro compartmentalization.

Despite the widespread use of yeast display in the evolution of binding interactions (18), sortase A is only the third enzyme to be evolved using yeast display, in addition to horseradish peroxidase (30, 31) and an esterase catalytic antibody (32). The results described herein highlight the advantageous features of yeast display for enzyme evolution, including quality control mechanisms within the secretory pathway that ensure display of properly folded proteins and compatibility with FACS (18). As an alternative to yeast or other cells as the vehicle for display, M13 phage simultaneously displaying an Sfp peptide substrate and an enzyme library may also be used (33). As the methodology disclosed herein does not rely on any particular screenable or selectable property of the substrates or product, it is in principle compatible with any bond-forming enzyme that can be expressed in a cell, e.g., in yeast, including glycosylated proteins that are likely incompatible with phage and mRNA display, provided that linkage of the substrates to CoA and to the affinity handle is possible and tolerated by the enzyme or its evolved variants. In cases in which the enzyme accepts only one of these modifications, product-specific antibodies in principle could be used to detect bond formation. Furthermore, integrating the yeast display system provided herein with the multicolor capabilities of FACS enables the evolution of enzyme substrate specificity.

REFERENCES

1. Savile C K, et al. (2010) Biocatalytic asymmetric synthesis of chiral amines from ketones applied to sitagliptin manufacture. Science 329:305-309.
2. Uttamapinant C, et al. (2010) A fluorophore ligase for site-specific protein labeling inside living cells. Proc Natl Acad Sci USA 107:10914-10919.
3. Yin J, et al. (2005) Genetically encoded short peptide tag for versatile protein labeling by Sfp phosphopantetheinyl transferase. Proc Natl Acad Sci USA 102:15815-15820.
4. Popp M W, Antos J M, Grotenbreg G M, Spooner E, Ploegh H L (2007) Sortagging: A versatile method for protein labeling. Nat Chem Biol 3:707-708.
5. Walsh G (2006) Biopharmaceutical benchmarks 2006. Nat Biotechnol 24:769-776.
6. Vellard M (2003) The enzyme as drug: Application of enzymes as pharmaceuticals. Curr Opin Biotechnol 14:444-450.
7. Chemy J R, Fidantsef A L (2003) Directed evolution of industrial enzymes: An update. Curr Opin Biotechnol 14:438-443.
8. Bershtein S, Tawfik D S (2008) Advances in laboratory evolution of enzymes. Curr Opin Chem Biol 12:151-158.
9. Bloom J D, et al. (2005) Evolving strategies for enzyme engineering. Curr Opin Struct Biol 15:447-452.
10. Turner N J (2003) Directed evolution of enzymes for applied biocatalysis. Trends Biotechnol 21:474-478.
11. Neuenschwander M, Butz M, Heintz C, Kast P, Hilvert D (2007) A simple selection strategy for evolving highly efficient enzymes. Nat Biotechnol 25:1145-1147.
12. van Sint Fiet S, van Beilen J B, Witholt B (2006) Selection of biocatalysts for chemical synthesis. Proc Natl Acad Sci USA 103:1693-1698.
13. Kelly B T, Baret J C, Taly V, Griffiths A D (2007) Miniaturizing chemistry and biology in microdroplets. Chem Commun (Camb) 1773-1788.
14. Lin H, Tao H, Cornish V W (2004) Directed evolution of a glycosynthase via chemical complementation. J Am Chem Soc 126:15051-15059.
15. Leconte A M, Chen L, Romesberg F E (2005) Polymerase evolution: Efforts toward expansion of the genetic code. J Am Chem Soc 127:12470-12471.
16. Seelig B, Szostak J W (2007) Selection and evolution of enzymes from a partially randomized non-catalytic scaffold. Nature 448:828-831.
17. Olsen M J, et al. (2000) Function-based isolation of novel enzymes from a large library. Nat Biotechnol 18:1071-1074.
18. Gai S A, Wittrup K D (2007) Yeast surface display for protein engineering and characterization. Curr Opin Struct Biol 17:467-473.
19. Boder E T, Wittrup K D (1997) Yeast surface display for screening combinatorial polypeptide libraries. Nat Biotechnol 15:553-557.
20. Varadarajan N, Rodriguez S, Hwang B Y, Georgiou G, Iverson B L (2008) Highly active and selective endopeptidases with programmed substrate specificities. Nat Chem Biol 4:290-294.
21. Yin J, Liu F, Li X, Walsh C T (2004) Labeling proteins with small molecules by site-specific posttranslational modification. J Am Chem Soc 126:7754-7755.
22. Zhou Z, et al. (2007) Genetically encoded short peptide tags for orthogonal protein labeling by Sfp and AcpS phosphopantetheinyl transferases. ACS Chem Biol 2:337-346.
23. Tsukiji S, Nagamune T (2009) Sortase-mediated ligation: A gift from Gram-positive bacteria to protein engineering. Chembiochem 10:787-798.
24. Zaccolo M, Williams D M, Brown D M, Gherardi E (1996) An approach to random mutagenesis of DNA using mixtures of triphosphate derivatives of nucleoside analogues. J Mol Biol 255:589-603.
25. Muller K M, et al. (2005) Nucleotide exchange and excision technology (NExT) DNA shuffling: A robust method for DNA fragmentation and directed evolution. Nucleic Acids Res 33:e117.
26. Bentley M L, Lamb E C, McCafferty D G (2008) Mutagenesis studies of substrate recognition and catalysis in the sortase A transpeptidase from *Staphylococcus aureus*. J Biol Chem 283:14762-14771.
27. Frankel B A, Tong Y, Bentley M L, Fitzgerald M C, McCafferty D G (2007) Mutational analysis of active site residues in the *Staphylococcus aureus* transpeptidase SrtA. Biochemistry 46:7269-7278.
28. Kruger R G, Dostal P, McCafferty D G (2004) Development of a high-performance liquid chromatography assay and revision of kinetic parameters for the *Staphylococcus aureus* sortase transpeptidase SrtA. Anal Biochem 326:42-48.

29. Suree N, et al. (2009) The structure of the *Staphylococcus aureus* sortase-substrate complex reveals how the universally conserved LPXTG sorting signal is recognized. J Biol Chem 284:24465-24477.
30. Agresti J J, et al. (2010) Ultrahigh-throughput screening in drop-based microfluidics for directed evolution. Proc Natl Acad Sci USA 107:4004-4009.
31. Antipov E, Cho A E, Wittrup K D, Klibanov A M (2008) Highly L and D enantioselective variants of horseradish peroxidase discovered by an ultrahigh-throughput selection method. Proc Natl Acad Sci USA 105:17694-17699.
32. Yang G, Withers S G (2009) Ultrahigh-throughput FACS-based screening for directed enzyme evolution. Chembiochem 10:2704-2715.
33. Sunbul M, Marshall N J, Zou Y, Zhang K, Yin J (2009) Catalytic turnover-based phage selection for engineering the substrate specificity of Sfp phosphopantetheinyl transferase. J Mol Biol 387:883-898.
34. Jiang L, et al. (2008) De novo computational design of retro-aldol enzymes. Science 319:1387-1391.
35. Rothlisberger D, et al. (2008) Kemp elimination catalysts by computational enzyme design. Nature 453:190-195.
36. Siegel J B, et al. (2010) Computational design of an enzyme catalyst for a stereoselective bimolecular Diels-Alder reaction. Science 329:309-313.

All publications, patents and sequence database entries mentioned herein, including those items listed in the Summary, Brief Description of the Drawings, Detailed Description, and Examples sections, are hereby incorporated by reference in their entirety as if each individual publication or patent was specifically and individually indicated to be incorporated by reference. In case of conflict, the present application, including any definitions herein, will control.

Equivalents and Scope

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A sortase comprising an amino acid sequence that is at least 90% identical to the amino acid sequence of *Staphylococcus aureus* (*S. aureus*) Sortase A as provided as SEQ ID NO: 1 or to amino acid residues 1-150 of SEQ ID NO: 21, wherein the amino acid sequence of the sortase comprises two or more mutations selected from the group consisting of P94S, P94R, E106G, F122Y, K154R, D160N, D165A, G174S, K190E, and K196T.

2. The sortase of claim 1, wherein the sortase comprises an amino acid sequence that is at least 95% identical to SEQ ID NO: 1 or to amino acid residues 1-150 of SEQ ID NO: 21.

3. The sortase of claim 1, wherein the amino acid sequence of the sortase comprises at least three mutations selected from the group consisting of P94S, P94R, E106G, F122Y, K154R, D160N, D165A, G174S, K190E, and K196T.

4. The sortase of claim 1, wherein the sortase comprises a P94S or P94R mutation, a D160N mutation, a D165A mutation, a K190E mutation, and a K196T mutation.

5. The sortase of claim 1, wherein the sortase comprises a P94S or P94R mutation, a D160N mutation, and a K196T mutation.

6. The sortase of claim 1, wherein the sortase comprises a P94S or P94R mutation, a D160N mutation, and a D165A mutation.

7. The sortase of claim 1, wherein the sortase comprises a P94S or P94R mutation, a D160N mutation, a D165A mutation, and a K196T mutation.

8. The sortase of claim 1, wherein the sortase exhibits a $k_{cat}$ that is at least 1.5-fold greater than the $k_{cat}$ of the Sortase A having the amino acid sequence provided as SEQ ID NO: 1 or amino acid residues 1-150 of SEQ ID NO: 21.

9. The sortase of claim 1, wherein the sortase exhibits a $K_M$ for a substrate comprising the amino acid sequence LPETG (SEQ ID NO: 32) that is at least 2-fold-less than the $K_M$ of the Sortase A having the amino acid sequence provided as SEQ ID NO: 1 or amino acid residues 1-150 of SEQ ID NO: 21.

10. The sortase of claim 1, wherein the sortase exhibits a $K_M$ for a substrate comprising the amino acid sequence GGG that is not more than 2-fold greater than the $K_M$ of the Sortase A having the amino acid sequence provided as SEQ ID NO: 1 or amino acid residues 1-150 of SEQ ID NO: 21.

11. The sortase of claim 1, wherein the sortase exhibits a ratio of $K_{cat}/K_M$ for a substrate comprising the amino acid sequence LPETG (SEQ ID NO: 32) that is least 2-fold greater than the $K_{cat}/K_M$ ratio of the Sortase A having the amino acid sequence provided as SEQ ID NO: 1 or amino acid residues 1-150 of SEQ ID NO: 21.

12. A sortase catalyzing transpeptidation of substrates other than LPETG (SEQ ID NO: 32), the sortase comprising an amino acid sequence that is at least 90% identical to the amino acid sequence of S. aureus Sortase A as provided as SEQ ID NO: 1 or to amino acid residues 1-150 of SEQ ID NO: 21,
wherein the amino acid sequence comprises two or more mutations selected from the group consisting of P86L, P94R, N98S, A104T, A118T, F122S, D124G, N127S, K134R, D160N, D165A K173E, K177E, K190E, and K196T.

13. The sortase of claim 12, wherein the substrate comprises the amino acid sequence LPXS, LAXT, MPXT, LAXS, NPXT, NAXT, NAXS, LPXP, or LPXTA (SEQ ID NO: 40), wherein each occurrence of X represents independently any amino acid residue.

14. The sortase of claim 12, wherein the substrate comprises the amino acid sequence LPESG (SEQ ID NO: 38).

15. A method for transpeptidation, the method comprising contacting the sortase of claim 1 with a substrate comprising an LPETG (SEQ ID NO: 32) sequence and with a substrate comprising a GGG sequence under conditions suitable for sortase-mediated transpeptidation.

16. The method of claim 15, wherein the LPETG (SEQ ID NO: 32) substrate and/or the GGG substrate are on the surface of a cell.

17. The method of claim 16, wherein the cell expresses a surface marker protein that is C-terminally fused to an LPETG (SEQ ID NO: 32) sequence.

18. The method of claim 16, wherein the cell expresses a surface marker protein that is N-terminally fused to a GGG sequence.

19. The method of claim 15, wherein the LPETG (SEQ ID NO: 32) substrate and/or the GGG substrate are polypeptides or proteins, and wherein the method results in the generation of a protein fusion.

20. The method of claim 15, wherein the LPETG (SEQ ID NO: 32) substrate or the GGG substrate comprises a non-protein structure.

21. The sortase of claim 1, wherein the sortase comprises an amino acid sequence that is at least 98% identical to SEQ ID NO: 1 or to amino acid residues 1-150 of SEQ ID NO: 21.

22. The sortase of claim 1, wherein the sortase comprises an amino acid sequence that is at least 99% identical to SEQ ID NO: 1 or to amino acid residues 1-150 of SEQ ID NO: 21.

23. The sortase of claim 1, wherein the amino acid sequence of the sortase comprises at least four mutations selected from the group consisting of P94S, P94R, E106G, F122Y, F154R, D160N, D165A, G174S, K190E, and K196T.

24. The sortase of claim 1, wherein the sortase exhibits a $K_M$ for a substrate comprising the amino acid sequence LPETG (SEQ ID NO: 32) that is at least 5-fold less than the $K_M$ of the Sortase A having the amino acid sequence provided as SEQ ID NO: 1 or amino acid residues 1-150 of SEQ ID NO: 21.

25. The sortase of claim 1, wherein the sortase exhibits a $K_M$ for a substrate comprising the amino acid sequence LPETG (SEQ ID NO: 32) that is at least 10-fold less than the $K_M$ of the Sortase A having the amino acid sequence provided as SEQ ID NO: 1 or of the Sortase A having the amino acid sequence provided by amino acid residues 1-150 of SEQ ID NO: 21.

26. The sortase of claim 1, wherein the sortase exhibits a $K_M$ for a substrate comprising the amino acid sequence GGG that is not more than 5-fold greater than the $K_M$ of the Sortase A having the amino acid sequence provided as SEQ ID NO: 1 or amino acid residues 1-150 of SEQ ID NO: 21.

27. The sortase of claim 1, wherein the sortase exhibits a $K_M$ for a substrate comprising the amino acid sequence GGG that is not more than 10-fold greater than the $K_M$ of the Sortase A having the amino acid sequence provided as SEQ ID NO: 1 or amino acid residues 1-150 of SEQ ID NO: 21.

28. The sortase of claim 1, wherein the sortase exhibits a ratio of $K_{cat}/K_M$ for a substrate comprising the amino acid sequence LPETG (SEQ ID NO: 32) that is least 5-fold greater than the $K_{cat}/K_M$ ratio of the Sortase A having the amino acid sequence provided as SEQ ID NO: 1 or amino acid residues 1-150 of SEQ ID NO: 21.

29. The sortase of claim 1, wherein the sortase exhibits a ratio of $K_{cat}/K_M$ for a substrate comprising the amino acid sequence LPETG (SEQ ID NO: 32) that is least 10-fold greater than the $K_{cat}/K_M$ ratio of the Sortase A having the amino acid sequence provided as SEQ ID NO: 1 or amino acid residues 1-150 of SEQ ID NO: 21.

30. The sortase of claim 1, wherein the sortase exhibits a ratio of $K_{cat}/K_m$ for a substrate comprising the amino acid sequence LPETG (SEQ ID NO: 32) that is least 50-fold greater than the $K_{cat}/K_M$ ratio of the Sortase A having the amino acid sequence provided as SEQ ID NO: 1 or amino acid residues 1-150 of SEQ ID NO: 21.

31. The sortase of claim 1, wherein the sortase has an amino acid sequence provided by a sequence selected from the group consisting of SEQ ID NOs: 17, 18, 19, 20, 26, 27, 28, 29, 30, and 31.

32. The method of claim 20, wherein the LPETG substrate (SEQ ID NO: 32) or the GGG substrate comprises a detectable label, a small molecule, a nucleic acid, or a polysaccharide.

* * * * *